(12) United States Patent
Davis et al.

(10) Patent No.: US 7,045,302 B2
(45) Date of Patent: May 16, 2006

(54) EXPRESSED LIGAND-VASCULAR INTERCELLULAR SIGNALING MOLECULE

(75) Inventors: Samuel Davis, New York, NY (US); George D. Yancopoulos, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 79 days.

(21) Appl. No.: 11/073,120

(22) Filed: Mar. 4, 2005

(65) Prior Publication Data

US 2005/0186665 A1    Aug. 25, 2005

Related U.S. Application Data

(60) Continuation of application No. 10/928,911, filed on Aug. 27, 2004, which is a division of application No. 10/225,060, filed on Aug. 21, 2002, now Pat. No. 6,825,008, which is a division of application No. 09/709,188, filed on Nov. 9, 2000, now Pat. No. 6,441,137, which is a division of application No. 08/740,223, filed on Oct. 25, 1996, now Pat. No. 6,265,564.

(60) Provisional application No. 60/022,999, filed on Aug. 2, 1996.

(51) Int. Cl.
*A61K 39/00* (2006.01)
*C07K 16/00* (2006.01)
*G01N 33/35* (2006.01)

(52) U.S. Cl. .................. 435/7.1; 424/192.1; 424/193.1; 424/185.1; 530/391.1

(58) Field of Classification Search ............. 530/391.1, 530/391.3, 391.7; 435/7.1; 424/185.1, 192.1, 424/193.1
See application file for complete search history.

(56) References Cited

U.S. PATENT DOCUMENTS 6,265,564 B1    7/2001   Davis et al.

FOREIGN PATENT DOCUMENTS

WO    WO96/11269    4/1996
WO    WO96/31598    10/1996

OTHER PUBLICATIONS

Science, Maisonpierre, P.C., et al., (1997) "Angiopoietin-2, a Natural Antagonist for Tie2 that Disrupts in vivo Angiogenesis", 277:55-60.

*Primary Examiner*—Christina Chan
*Assistant Examiner*—Maher Haddad
(74) *Attorney, Agent, or Firm*—Valeta Gregg, Esq.; Ying-Zi Yang

(57) ABSTRACT

The present invention provides for a modified TIE-2 ligand 2 which has been altered by addition, deletion or substitution of one or more amino acids, or by way of tagging, with for example, the Fc portion of human IgG-1, but which retains its ability to bind the TIE-2 receptor.

4 Claims, 1 Drawing Sheet

US 7,045,302 B2

EXPRESSED LIGAND-VASCULAR INTERCELLULAR SIGNALING MOLECULE

CROSS-REFERENCE TO RELATED APPLICATIONS

This application is a continuation of U.S. Ser. No. 10/928,911 filed Aug. 27, 2004 which is a divisional of U.S. Ser. No. 10/225,060 filed Aug. 21, 2002, now U.S. Pat. No. 6,825,008, which is a divisional of U.S. Ser. No. 09/709,188, filed Nov. 9, 2000, now U.S. Pat. No. 6,441,137, which is a divisional of U.S. Ser. No. 08/740,223, filed Oct. 25, 1996, now U.S. Pat. No. 6,265,564, which claims the priority of U.S. Provisional application 60/022,999 filed Aug. 2, 1996. The disclosures of these publications are hereby incorporated by reference in their entireties into this application.

FIELD OF THE INVENTION

The present invention is directed to a novel modified TIE-2 ligand that binds the TIE-2 receptor, as well as to methods of making and using the modified ligand. The invention further provides a nucleic acid sequence encoding the modified ligand, and methods for the generation of nucleic acid encoding the modified ligand and the gene product.

SUMMARY OF THE INVENTION

The present invention provides for a composition comprising a modified TIE-2 ligand substantially free of other proteins. As used herein, modified TIE-2 ligand refers to a ligand of the TIE family of ligands, whose representatives comprise ligands TL1, TL2, TL3 and TL4, which has been altered by addition, deletion or substitution of one or more amino acids, or by way of tagging, with for example, the Fc portion of human IgG-1, but which retains its ability to bind the TIE-2 receptor. Modified TIE-2 ligand also includes a chimeric TIE-2 ligand comprising at least a portion of a first TIE-2 ligand and a portion of a second TIE-2 ligand which is different from the first, for example, TL1 followed by TL2. The invention envisions other combinations using additional TIE-2 ligand family members. For example, other combinations for creating a chimeric TIE-2 ligand are possible, including but not limited to those combinations wherein the first ligand is selected from the group consisting of TL1, TL2, TL3 and TL4, and the second ligand, different from the first ligand, is selected from the group consisting of TL1, TL2, TL3 and TL4.

The invention also provides for an isolated nucleic acid molecule encoding a modified TIE-2 ligand of the invention. The isolated nucleic acid may be DNA, cDNA or RNA. Also provided are vectors comprising an isolated nucleic acid molecule encoding a modified TIE-2 ligand, host-vector systems for the production in a suitable host cell of a polypeptide having the biological activity of a modified TIE-2 ligand. The suitable host cell may be bacterial, yeast, insect or mammalian. Also provided are methods of producing a polypeptide having the biological activity of a modified TIE-2 ligand which comprises growing cells of the host-vector system under conditions permitting production of the polypeptide and recovering the polypeptide so produced.

The invention herein described of an isolated nucleic acid molecule encoding a modified TIE-2 ligand further provides for the development of the ligand as a therapeutic for the treatment of patients suffering from disorders involving cells, tissues or organs which express the TIE-2 receptor. The present invention also provides for an antibody which specifically binds such a therapeutic molecule, including monoclonal or polyclonal antibodies, and methods of using such an antibody.

The present invention also provides for an antibody which specifically binds a modified TIE-2 ligand of the invention. Thus, the invention further provides for therapeutic compositions comprising an antibody which specifically binds a modified TIE-2 ligand, in a pharmaceutically acceptable vehicle. The invention also provides for a method of blocking blood vessel growth in a mammal by administering an effective amount of a therapeutic composition comprising an antibody which specifically binds a receptor activating modified TIE-2 ligand as described herein, in a pharmaceutically acceptable vehicle.

The invention further provides for therapeutic compositions comprising a modified TIE-2 ligand as described herein, in a pharmaceutically acceptable vehicle. The invention also provides for a method of promoting neovascularization in a patient by administering an effective amount of a therapeutic composition comprising a receptor activating modified TIE-2 ligand of the invention, in a pharmaceutically acceptable vehicle. In one embodiment, the method may be used to promote wound healing. In another embodiment, the method may be used to treat ischemia. In yet another embodiment, a receptor activating modified TIE-2 ligand as described herein is used, alone or in combination with other hematopoietic factors, to promote the proliferation or differentiation of hematopoietic stem cells, B cells or megakaryocytic cells.

Alternatively, the invention provides that a modified TIE-2 ligand may be conjugated to a cytotoxic agent and a therapeutic composition prepared therefrom. The invention further provides for a receptorbody which specifically binds a modified TIE-2 ligand. The invention further provides for therapeutic compositions comprising a receptorbody which specifically binds a modified TIE-2 ligand in a pharmaceutically acceptable vehicle. Further provided are methods of blocking blood vessel growth in a mammal by administering an effective amount of a therapeutic composition comprising a receptorbody which specifically binds a modified TIE-2 ligand in a pharmaceutically acceptable vehicle.

The invention also provides for a TIE-2 receptor antagonist as well as a method of inhibiting TIE-2 biological activity in a mammal comprising administering to the mammal an effective amount of a TIE-2 antagonist. According to the invention, the antagonist may be a modified TIE-2 ligand as described herein which binds to, but does not activate, the TIE-2 receptor.

DETAILED DESCRIPTION OF THE INVENTION

Figure 1:
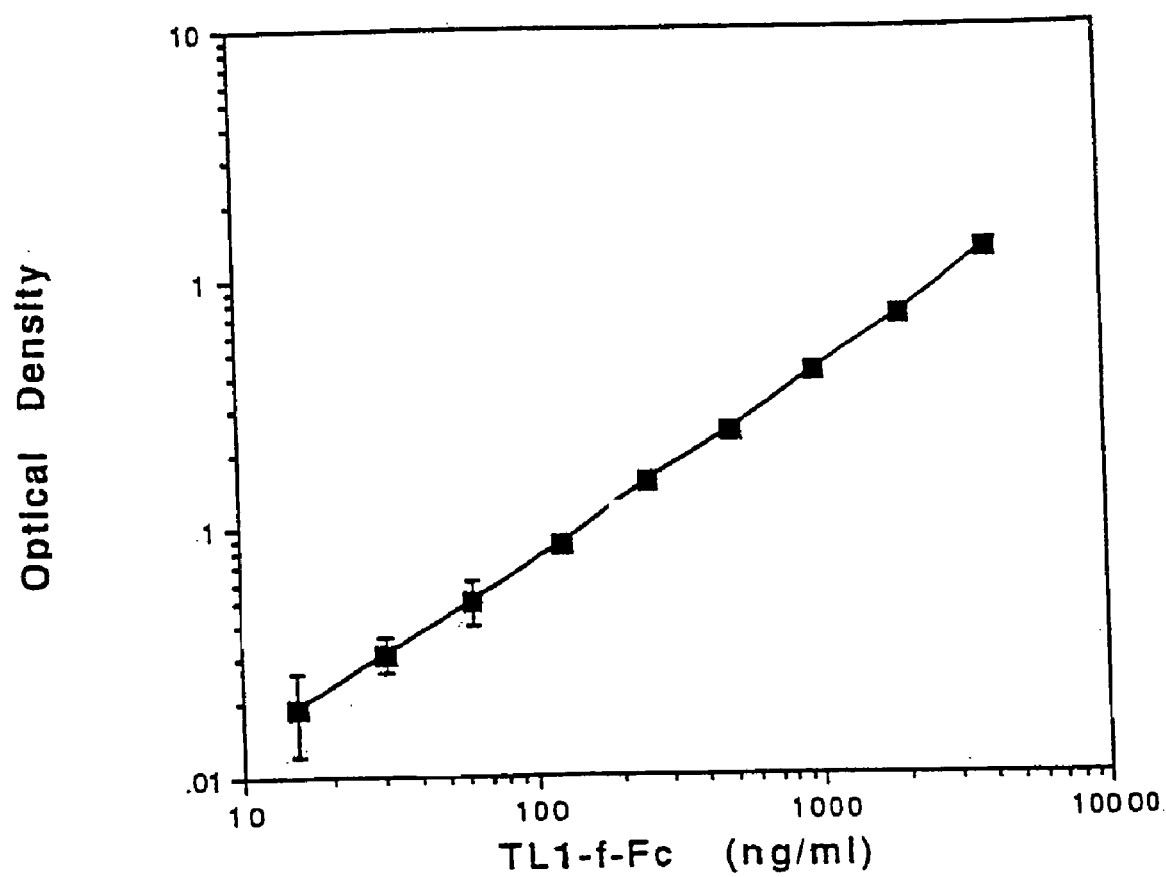
FIG. 1 shows a typical curve of TIE2 ligand 1 ligandbody comprising the fibrinogen domain (FD) of TL1 bound to the Fc domain of IgG (TL1-FD-Fc) binding to immobilized TIE2 ectodomain in a quantitative cell-free binding assay.

As described in greater detail below, applicants have created novel modified TIE-2 ligands that bind the TIE-2 receptor. The present invention provides for a composition comprising a modified TIE-2 ligand substantially free of other proteins. As used herein, modified TIE-2 ligand refers to a ligand of the TIE family of ligands, whose representatives comprise ligands TL1, TL2, TL3 and TL4 as described herein, which has been altered by addition, deletion or substitution of one or more amino acids, or by way of tagging, with for example, the Fc portion of human IgG-1, but which retains its ability to bind the TIE-2 receptor. Modified TIE-2 ligand also includes a chimeric TIE-2 ligand comprising at least a portion of a first TIE-2 ligand and a portion of a second TIE-2 ligand which is different from the first. By way of non-limiting example, the first TIE-2 ligand is TL1 and the second TIE-2 ligand is TL2. The invention envisions other combinations using additional TIE-2 ligand family members. For example, other combinations for creating a chimeric TIE-2 ligand are possible, including but not limited to those combinations wherein the first ligand is selected from the group consisting of TL1, TL2, TL3 and TL4, and the second ligand, different from the first ligand, is selected from the group consisting of TL1, TL2, TL3 and TL4.

The invention also provides for an isolated nucleic acid molecule encoding the modified TIE-2 ligands of the invention.

The present invention comprises the modified TIE-2 ligands and their amino acid sequences, as well as functionally equivalent variants thereof, as well as proteins or peptides comprising substitutions, deletions or insertional mutants of the described sequences, which bind TIE-2 receptor and act as agonists or antagonists thereof. Such variants include those in which amino acid residues are substituted for residues within the sequence resulting in a silent change. For example, one or more amino acid residues within the sequence can be substituted by another amino acid(s) of a similar polarity which acts as a functional equivalent, resulting in a silent alteration. Substitutes for an amino acid within the sequence may be selected from other members of the class to which the amino acid belongs. For example, the class of nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Also included within the scope of the invention are proteins or fragments or derivatives thereof which exhibit the same or similar biological activity as the modified TIE-2 ligands described herein, and derivatives which are differentially modified during or after translation, e.g., by glycosylation, proteolytic cleavage, linkage to an antibody molecule or other cellular ligand, etc. Functionally equivalent molecules also include molecules that contain modifications, including N-terminal modifications, which result from expression in a particular recombinant host, such as, for example, N-terminal methylation which occurs in certain bacterial (e.g. *E. coli*) expression systems.

The present invention also encompasses the nucleotide sequences that encode the proteins described herein as modified TIE-2 ligands, as well as host cells, including yeast, bacteria, viruses, and mammalian cells, which are genetically engineered to produce the proteins, by e.g. transfection, transduction, infection, electroporation, or microinjection of nucleic acid encoding the modified TIE-2 ligands described herein in a suitable expression vector. The present invention also encompasses introduction of the nucleic acid encoding modified TIE-2 ligands through gene therapy techniques such as is described, for example, in Finkel et al. (1995) FASEB J. 9:843–851; Guzman et al. (1994) PNAS (USA) 91:10732–10736.

The present invention encompasses DNA and RNA sequences that hybridize to a modified TIE-2 ligand encoding nucleotide sequence, under conditions of moderate stringency, as defined in, for example, Sambrook et al. (1989) Molecular Cloning: A Laboratory Manual, 2 ed. Vol. 1, pp. 101–104, Cold Spring Harbor Laboratory Press. Thus, a nucleic acid molecule contemplated by the invention includes one having a nucleotide sequence deduced from an amino acid sequence of a modified TIE-2 ligand prepared as described herein, as well as a molecule having a sequence of nucleotides that hybridizes to such a nucleotide sequence, and also a nucleotide sequence which is degenerate of the above sequences as a result of the genetic code, but which encodes a ligand that binds TIE-2 receptor and which has an amino acid sequence and other primary, secondary and tertiary characteristics that are sufficiently duplicative of a modified TIE-2 ligand described herein so as to confer on the molecule the same biological activity as the modified TIE-2 ligand described herein.

The present invention provides for an isolated nucleic acid molecule encoding a modified TIE-2 ligand that binds and activates TIE-2 receptor comprising a nucleotide sequence encoding TIE-2 ligand 1 wherein the portion of the nucleotide sequence that encodes the N-terminal domain of TIE-2 ligand 1 is replaced by a nucleotide sequence that encodes the N-terminal domain of TIE-2 ligand 2. The invention also provides for such a nucleic acid molecule, with a further modification such that the portion of the nucleotide sequence that encodes the coiled-coil domain of TIE-2 ligand 1 is replaced by a nucleotide sequence that encodes the coiled-coil domain of TIE-2 ligand 2.

The present invention also provides for an isolated nucleic acid molecule encoding a modified TIE-2 ligand that binds and activates TIE-2 receptor comprising a nucleotide sequence encoding TIE-2 ligand 1 wherein the portion of the nucleotide sequence that encodes the N-terminal domain of TIE-2 ligand 1 is replaced by a nucleotide sequence that encodes the N-terminal domain of TIE-2 ligand 2 and which is further modified to encode a different amino acid instead of the cysteine residue encoded by nucleotides 784–786 of SEQ ID NO:25. A serine residue is preferably substituted for the cysteine residue. In another embodiment, the nucleic acid molecule is further modified to encode a different amino acid instead of the arginine residue encoded by nucleotides 199–201 SEQ ID NO:25. A serine residue is preferably substituted for the arginine residue.

The present invention also provides for an isolated nucleic acid molecule encoding a modified TIE-2 ligand that binds and activates TIE-2 receptor comprising a nucleotide sequence encoding TIE-2 ligand 1 which is modified to encode a different amino acid instead of the cysteine residue at amino acid position 245. A serine residue is preferably substituted for the cysteine residue.

The invention further provides for an isolated nucleic acid molecule encoding a modified TIE-2 ligand that binds but does not activate TIE-2 receptor comprising a nucleotide sequence encoding TIE-2 ligand 1 wherein the portion of the nucleotide sequence that encodes the N-terminal domain of TIE-2 ligand 1 is deleted. The invention also provides for such a nucleic acid molecule further modified so that the portion of the nucleotide sequence that encodes the coiled-coil domain of TIE-2 ligand 1 is deleted and the portion encoding the fibrinogen-like domain is fused in-frame to a nucleotide sequence encoding a human immunoglobulin gamma-1 constant region (IgG1 Fc).

The invention further provides for an isolated nucleic acid molecule encoding a modified TIE-2 ligand that binds but does not activate TIE-2 receptor comprising a nucleotide sequence encoding TIE-2 ligand 2 wherein the portion of the nucleotide sequence that encodes the N-terminal domain of TIE-2 ligand 2 is deleted. The invention also provides for such a nucleic acid molecule further modified so that the portion of the nucleotide sequence that encodes the coiled-coil domain of TIE-2 ligand 2 is deleted and the portion encoding the fibrinogen-like domain is fused in-frame to a nucleotide sequence encoding a human immunoglobulin gamma-1 constant region (IgG1 Fc).

The invention further provides for an isolated nucleic acid molecule encoding a modified TIE-2 ligand that binds but does not activate TIE-2 receptor comprising a nucleotide sequence encoding TIE-2 ligand 1 wherein the portion of the nucleotide sequence that encodes the fibrinogen-like domain of TIE-2 ligand 1 is replaced by a nucleotide sequence that encodes the fibrinogen-like domain of TIE-2 ligand 2. The invention also provides for such a nucleic acid molecule further modified so that the portion of the nucleotide sequence that encodes the coiled-coil domain of TIE-2 ligand 1 is replaced by a nucleotide sequence that encodes the coiled-coil domain of TIE-2 ligand 2.

The present invention also provides for a chimeric TIE-2 ligand comprising at least a portion of a first TIE-2 ligand and a portion of a second TIE-2 ligand which is different from the first, wherein the first and second TIE-2 ligands are selected from the group consisting of TIE-2 Ligand-1, TIE-2 Ligand-2, TIE Ligand-3 and TIE Ligand-4. Preferably, the chimeric TIE ligand comprises at least a portion of TIE-2 Ligand-1 and a portion of TIE-2 Ligand-2. Nucleic acid molecules encoding a chimeric TIE ligand are shown in SEQ ID NOs:19, 21, 23 and 25.

Any of the methods known to one skilled in the art for the insertion of DNA fragments into a vector may be used to construct expression vectors encoding a modified TIE-2 ligand using appropriate transcriptional/translational control signals and the protein coding sequences. These methods may include in vitro recombinant DNA and synthetic techniques and in vivo recombinations (genetic recombination). Expression of a nucleic acid sequence encoding a modified TIE-2 ligand or peptide fragments thereof may be regulated by a second nucleic acid sequence which is operably linked to the a modified TIE-2 ligand encoding sequence such that the modified TIE-2 ligand protein or peptide is expressed in a host transformed with the recombinant DNA molecule. The invention further encompasses the production of antisense compounds which are capable of specifically hybridizing with a sequence of RNA encoding a modified TIE-2 ligand to modulate its expression (see U.S. Pat. No. 5,166, 195).

Thus, according to the invention, expression vectors capable of being replicated in a bacterial or eukaryotic host comprising a nucleic acid encoding a modified TIE-2 ligand as described herein, are used to transfect a host and thereby direct expression of such nucleic acid to produce a modified TIE-2 ligand, which may then be recovered in a biologically active form. As used herein, a biologically active form includes a form capable of binding to TIE receptor and causing a biological response such as a differentiated function or influencing the phenotype of the cell expressing the receptor. Such biologically active forms could, for example, induce phosphorylation of the tyrosine kinase domain of TIE receptor. Alternatively, the biological activity may be an effect as an antagonist to the TIE receptor. In alternative embodiments, the active form of a modified TIE-2 ligand is one that can recognize TIE receptor and thereby act as a targeting agent for the receptor for use in both diagnostics and therapeutics. In accordance with such embodiments, the active form need not confer upon any TIE expressing cell any change in phenotype.

In additional embodiments of the invention, a modified TIE-2 ligand encoding gene may be used to inactivate or "knock out" an endogenous gene by homologous recombination, and thereby create a TIE ligand deficient cell, tissue, or animal. For example, and not by way of limitation, the recombinant TIE ligand-4 encoding gene may be engineered to contain an insertional mutation, for example the neo gene, which would inactivate the native TIE ligand-4 encoding gene. Such a construct, under the control of a suitable promoter, may be introduced into a cell, such as an embryonic stem cell, by a technique such as transfection, transduction, or injection. Cells containing the construct may then be selected by G418 resistance. Cells which lack an intact TIE ligand-4 encoding gene may then be identified, e.g. by Southern blotting, PCR detection, Northern blotting or assay of expression. Cells lacking an intact TIE ligand-4 encoding gene may then be fused to early embryo cells to generate transgenic animals deficient in such ligand. Such an animal may be used to define specific in vivo processes, normally dependent upon the ligand.

The present invention also provides for the utilization of a modified TIE-2 ligand which activates the TIE-2 receptor as described herein, to support the survival and/or growth and/or migration and/or differentiation of TIE-2 receptor expressing cells. Thus, the ligand may be used as a supplement to support, for example, endothelial cells in culture.

In addition, the invention further contemplates compositions wherein the TIE ligand is the receptor binding domain of a TIE-2 ligand described herein. For example, TIE-2 ligand 1 contains a "coiled coil" domain (beginning at the 5' end and extending to the nucleotide at about position 1160 of SEQ ID NO:1 and about position 1157 of SEQ ID NO:3) and a fibrinogen-like domain (which is encoded by the nucleotide sequence of SEQ ID NO;1 beginning at about position 1161 and about position 1158 of SEQ ID NO:3). The fibrinogen-like domain of TIE-2 ligand 2 is believed to begin on or around the same amino acid sequence as in ligand 1 (FRDCA) which is encoded by nucleotides beginning around 1197 of SEQ ID NO:5. The fibrinogen-like domain of TIE ligand-3 is believed to begin on or around the amino acid sequence which is encoded by nucleotides beginning around position 929 of SEQ ID NO:9. Multimerization of the coiled coil domains during production of the ligand hampers purification. Applicants have discovered, however, that the fibrinogen-like domain comprises the TIE-2 receptor binding domain. The monomeric forms of the fibrinogen-like domain do not, however, appear to bind the receptor. Studies utilizing myc-tagged fibrinogen-like domain, which has been "clustered" using anti-myc antibodies, do bind the TIE-2 receptor (Methods of production of clustered ligands and ligandbodies are described in Davis, et al. (1994) Science 266:816–819). Based on these finding, applicants produced "ligandbodies" which comprise the fibrinogen-like domain of the TIE-2 ligands coupled to the Fc domain of IgG ("fFc's"). These ligandbodies, which form dimers, efficiently bind the TIE-2 receptor. Accordingly, the present invention contemplates the production of modified TIE ligandbodies which may be used as targeting agents, in diagnostics or in therapeutic applications, such as targeting agents for tumors and/or associated vasculature wherein a TIE antagonist is indicated.

The invention herein further provides for the development of the ligand, a fragment or derivative thereof, or another molecule which is a receptor agonist or antagonist, as a therapeutic for the treatment of patients suffering from disorders involving cells, tissues or organs which express the TIE receptor. Such molecules may be used in a method of treatment of the human or animal body, or in a method of diagnosis.

Because TIE receptor has been identified in association with endothelial cells and, as demonstrated herein, blocking of TIE-2 ligand 1 appears to prevent vascularization, applicants expect that a modified TIE-2 ligand described herein may be useful for the induction of vascularization in diseases or disorders where such vascularization is indicated. Such diseases or disorders would include wound healing, ischaemia and diabetes. The ligands may be tested in animal models and used therapeutically as described for other agents, such as vascular endothelial growth factor (VEGF), another endothelial cell-specific factor that is angiogenic (Ferrara et al. U.S. Pat. No. 5,332,671). The Ferrara reference, as well as other studies, describe in vitro and in vivo studies that may be used to demonstrate the effect of an angiogenic factor in enhancing blood flow to ischemic myocardium, enhancing wound healing, and in other therapeutic settings wherein neoangiogenesis is desired [see Sudo et al. European Patent Application 0 550 296 A2; Banai et al. (1994) Circulation 89:2183–2189;Unger et al. (1994) Am. J. Physiol. 266:H1588–H1595; Lazarous et al. (1995) Circulation 91:145–153). According to the invention, a modified TIE-2 ligand may be used alone or in combination with one or more additional pharmaceutically active compounds such as, for example, VEGF or basic fibroblast growth factor (bFGF), as well as cytokines, neurotrophins, etc.

Conversely, antagonists of the TIE receptor, such as modified TIE-2 ligands which bind but do not activate the receptor as described herein, receptorbodies, and TIE-2 ligand 2, would be useful to prevent or attenuate vascularization, thus preventing or attenuating, for example, tumor growth. These agents may be used alone or in combination with other compositions, such as anti-VEGF antibodies, that have been shown to be useful in treating conditions in which the therapeutic intent is to block angiogenesis. Applicants expect that a modified TIE-2 ligand described herein may also be used in combination with agents, such as cytokine antagonists such as IL-6 antagonists, that are known to block inflammation.

For example, applicants have determined that TIE ligands are expressed in cells within, or closely associated with, tumors. For example, TIE-2 ligand 2 appears to be tightly associated with tumor endothelial cells. Accordingly, it and other TIE antagonists may also be useful in preventing or attenuating, for example, tumor growth. In addition, TIE ligands or ligandbodies may be useful for the delivery of toxins to a receptor bearing cell. Alternatively, other molecules, such as growth factors, cytokines or nutrients, may be delivered to a TIE receptor bearing cell via TIE ligands or ligandbodies. TIE ligands or ligandbodies such as modified TIE-2 ligand described herein may also be used as diagnostic reagents for TIE receptor, to detect the receptor in vivo or in vitro. Where the TIE receptor is associated with a disease state, TIE ligands or ligandbodies such as a modified TIE-2 ligand may be useful as diagnostic reagents for detecting the disease by, for example, tissue staining or whole body imaging. Such reagents include radioisotopes, flurochromes, dyes, enzymes and biotin. Such diagnostics or targeting agents may be prepared as described in Alitalo, et al. WO 95/26364 and Burrows et al. (1993) PNAS (USA) 90:8996–9000, which is incorporated herein in its entirety.

In other embodiments, the TIE ligands, a receptor activating modified TIE-2 ligand described herein are used as hematopoietic factors. A variety of hematopoietic factors and their receptors are involved in the proliferation and/or differentiation and/or migration of the various cells types contained within blood. Because the TIE receptors are expressed in early hematopoietic cells, the TIE ligands are expected to play a comparable role in the proliferation or differentiation or migration of these cells. Thus, for example, TIE containing compositions may be prepared, assayed, examined in in vitro and in vivo biological systems and used therapeutically as described in any of the following: U.S. Pat. No. 4,810,643, Lee et al. (1985) Proc. Natl. Acad. Sci. USA 82:4360–4364; Wong et al. (1985) Science 228:810–814; Yokota et al. (1984) Proc. Natl. Acad. Sci (USA) 81:1070; WO 9105795; and WO 95/19985. Accordingly, receptor activating modified TIE-2 ligand may be used to diagnose or treat conditions in which normal hematopoiesis is suppressed, including, but not limited to anemia, thrombocytopenia, leukopenia and granulocytopenia. In a preferred embodiment, receptor activating modified TIE-2 ligand may be used to stimulate differentiation of blood cell precursors in situations where a patient has a disease, such as acquired immune deficiency syndrome (AIDS) which has caused a reduction in normal blood cell levels, or in clinical settings in which enhancement of hematopoietic populations is desired, such as in conjunction with bone marrow transplant, or in the treatment of aplasia or myelosuppression caused by radiation, chemical treatment or chemotherapy.

The receptor activating modified TIE-2 ligands of the present invention may be used alone, or in combination with another pharmaceutically active agent such as, for example, cytokines, neurotrophins, interleukins, etc. In a preferred embodiment, the ligands may be used in conjunction with any of a number of the above referenced factors which are known to induce stem cell or other hematopoietic precursor proliferation, or factors acting on later cells in the hematopoietic pathway, including, but not limited to, hemopoietic maturation factor, thrombopoietin, stem cell factor, erythropoietin, G-CSF, GM-CSF, etc.

In an alternative embodiment, TIE receptor antagonists are used to diagnose or treat patients in which the desired result is inhibition of a hematopoietic pathway, such as for the treatment of myeloproliferative or other proliferative disorders of blood forming organs such as thrombocythemias, polycythemias and leukemias. In such embodiments, treatment may comprise use of a therapeutically effective amount of the a modified TIE-2 ligand, TIE antibody, TIE receptorbody, a conjugate of a modified TIE-2 ligand, or a ligandbody or fFC as described herein.

The present invention also provides for pharmaceutical compositions comprising a modified TIE-2 ligand or ligandbodies described herein, peptide fragments thereof, or derivatives in a pharmacologically acceptable vehicle. The modified TIE-2 ligand proteins, peptide fragments, or derivatives may be administered systemically or locally. Any appropriate mode of administration known in the art may be used, including, but not limited to, intravenous, intrathecal, intraarterial, intranasal, oral, subcutaneous, intraperitoneal, or by local injection or surgical implant. Sustained release formulations are also provided for.

The present invention also provides for an antibody which specifically binds such a therapeutic molecule. The invention also provides for a method of using such a monoclonal or polyclonal antibody to measure the amount of the therapeutic molecule in a sample taken from a patient for purposes of monitoring the course of therapy.

The invention further provides for a therapeutic composition comprising a modified TIE-2 ligand or ligandbody and a cytotoxic agent conjugated thereto. In one embodiment, the cytotoxic agent may be a radioisotope or toxin.

The invention further provides for a receptorbody which specifically binds a modified TIE-2 ligand, as well as a therapeutic composition comprising the receptorbody in a pharmaceutically acceptable vehicle, and a method of blocking blood vessel growth in a human comprising administering an effective amount of the therapeutic composition.

The invention also provides for a therapeutic composition comprising a receptor activating modified TIE-2 ligand or ligandbody in a pharmaceutically acceptable vehicle, as well as a method of promoting neovascularization in a patient comprising administering to the patient an effective amount of the therapeutic composition.

EXAMPLE 1

Identification of the ABAE Cell Line as Reporter Cells for the TIE-2 Receptor

Adult BAE cells are registered in the European Cell Culture Repository, under ECACC#92010601. (See PNAS 75:2621 (1978)). Northern (RNA) analyses revealed moderate levels of tie-2 transcripts in the ABAE (Adult Bovine Arterial Endothelial) cell line, consistent with in situ hybridization results that demonstrated almost exclusive localization of tie-2 RNAs to vascular endothelial cells. We therefore examined ABAE cell lysates for the presence of TIE-2 protein, as well as the extent to which this TIE-2 protein is tyrosine-phosphorylated under normal versus serum-deprived growth conditions. ABAE cell lysates were harvested and subjected to immunoprecipitation, followed by Western blot analyses of immunoprecipitated proteins with TIE-2 specific and phosphotyrosine-specific antisera. Omission or inclusion of TIE-2 peptides as specific blocking molecules during TIE-2 immunoprecipitation allowed unambiguous identification of TIE-2 as a moderately detectable protein of ~150 kD whose steady-state phosphotyrosine levels diminish to near undetectable levels by prior serum-starvation of the cells.

Culture of ABAE cells and harvest of cell lysates was done as follows. Low-passage-number ABAE cells were plated as a monolayer at a density of $2\times10^6$ cells/150 mm plastic petri plate (Falcon) and cultured in Dulbecco's modified Eagle's medium (DMEM) containing 10% bovine calf serum (10% BCS), 2 mM L-glutamine (Q) and 1% each of penicillin and streptomycin (P-S) in an atmosphere of 5% $CO_2$. Prior to harvest of cell lysates, cells were serum-starved for 24 hours in DMEM/Q/P-S, followed by aspiration of the medium and rinsing of the plates with ice-cold phosphate buffered saline (PBS) supplemented with sodium orthovanadate, sodium fluoride and sodium benzamidine. Cells were lysed in a small volume of this rinse buffer that had been supplemented with 1% NP40 detergent and the protease inhibitors PMSF and aprotinin. Insoluble debris was removed from the cell lysates by centrifugation at $14,000\times G$ for 10 minutes, at 4° C. and the supernatants were subjected to immunoprecipitation with antisera specific for TIE-2 receptor, with or without the presence of blocking peptides added to ~20 mg/ml lysate. Immunoprecipitated proteins were resolved by PAGE (7.5% Laemmli gel), and then electro-transferred to PVDF membrane and incubated either with various TIE-2- or phosphotyrosine-specific antisera. TIE-2 protein was visualized by incubation of the membrane with HRP-linked secondary antisera followed by treatment with ECL reagent (Amersham).

EXAMPLE 2

Cloning and Expression of the TIE-2 Receptorbody for Affinity-based Study of TIE-2 Ligand Interactions An expression construct was created that would yield a secreted protein consisting of the entire extracellular portion of the rat TIE-2 receptor fused to the human immunoglobulin gamma-1 constant region (IgG1 Fc). This fusion protein is called a TIE-2 "receptorbody" (RB), and would be normally expected to exist as a dimer in solution based on formation of disulfide linkages between individual IgG1 Fc tails. The Fc portion of the TIE-2 RB was prepared as follows. A DNA fragment encoding the Fc portion of human IgG1 that spans from the hinge region to the carboxy-terminus of the protein, was amplified from human placental cDNA by PCR with oligonucleotides corresponding to the published sequence of human IgG1; the resulting DNA fragment was cloned in a plasmid vector. Appropriate DNA restriction fragments from a plasmid encoding the full-length TIE-2 receptor and from the human IgG1 Fc plasmid were ligated on either side of a short PCR-derived fragment that was designed so as to fuse, in-frame, the TIE-2 and human IgG1 Fc protein-coding sequences. Thus, the resulting TIE-2 ectodomain-Fc fusion protein precisely substituted the IgG1 Fc in place of the region spanning the TIE-2 transmembrane and cytoplasmic domains. An alternative method of preparing RBs is described in Goodwin, et. al. Cell 73:447–456 (1993).

Milligram quantities of TIE-2 RB were obtained by cloning the TIE-2 RB DNA fragment into the pVL1393 baculovirus vector and subsequently infecting the *Spodoptera frugiperda* SF-21AE insect cell line. Alternatively, the cell line SF-9 (ATCC Accession No. CRL-1711) or the cell line BTI-TN-5b1-4 may be used. DNA encoding the TIE-2 RB was cloned as an Eco RI-NotI fragment into the baculovirus transfer plasmid pVL393. Plasmid DNA purified by cesium chloride density gradient centrifugation was recombined into viral DNA by mixing 3 mg of plasmid DNA with 0.5 mg of Baculo-Gold DNA (Pharminigen), followed by introduction into-liposomes using 30 mg Lipofectin (GIBCO-BRL). DNA-liposome mixtures were added to SF-21AE cells ($2\times10^6$ cells/60 mm dish) in TMN-FH medium (Modified Grace's Insect Cell Medium (GIBCO-BRL) for 5 hours at 27° C., followed by incubation at 27° C. for 5 days in TMN-FH medium supplemented with 5% fetal calf serum. Tissue culture medium was harvested for plaque purification of recombinant viruses, which was carried out using methods previously described (O'Reilly et al. (1992) *Baculovirus Expression Vectors—A Laboratory Manual*. 1992, New York: W. H. Freeman) except that the agarose overlay contained 125 mg/mL X-gal (5-bromo-4-chloro-3-indolyl-b-D-galactopyranoside; GIBCO-BRL). After 5 days of incubation at 27° C., non-recombinant plaques were scored by positive chromogenic reaction to the X-gal substrate, and their positions marked. Recombinant plaques were then visualized by addition of a second overlay containing 100 mg/mL MTT. Putative recombinant virus plaques were picked by plug aspiration, and purified by multiple rounds of plaque isolation to assure homogeneity. Virus stocks were generated by serial, low-multiplicity passage of plaque-purified virus. Low passage stocks of one virus clone (vTIE-2 receptorbody) were produced.

SF-21AE cells were cultured in serum free medium (SF-900 II, Gibco BRL) containing 1× antibiotic/antimycotic solution (Gibco BRL) and 25 mg/L Gentamycin (Gibco BRL). Pluronic F-68 was added as a surfactant to a final concentration of 1 g/L. Cultures (4 L) were raised in a bioreactor (Artisan Cell Station System) for at least three days prior to infection. Cells were grown at 27° C., with gassing to 50% dissolved oxygen, at a gas flow rate of 80 mL/min (aeration at a sparge ring). Agitation was by means of a marine impeller at a rate of 100 rpm. Cells were harvested in mid-logarithmic growth phase (~2×10$^6$ cells/mL), concentrated by centrifugation, and infected with 5 plaque forming units of vTIE-2 receptorbody per cell. Cells and inoculum were brought to 400 mL with fresh medium, and virus was adsorbed for 2 hours at 27° C. in a spinner flask. The culture was then resuspended in a final volume of 8 L with fresh serum-free medium, and the cells incubated in the bioreactor using the previously described conditions.

Culture medium from vTIE-2 receptorbody-infected SF21AE cells were collected by centrifugation (500×g, 10 minutes) at 72 hours post-infection. Cell supernatants were brought to pH 8 with NaOH. EDTA was added to a final concentration of 10 mM and the supernatant pH was readjusted to 8. Supernatants were filtered (0.45 mm, Millipore) and loaded on a protein A column (protein A sepharose 4 fast flow or HiTrap protein A; Pharmacia). The column was washed with PBS containing 0.5 M NaCl until the absorbance at 280 nm decreased to baseline. The column was washed in PBS and eluted with 0.5 M acetic acid. Column fractions were immediately neutralized by eluting into tubes containing 1 M Tris pH 9. The peak fractions containing the TIE-2 receptorbody were pooled and dialyzed versus PBS.

EXAMPLE 3

TIE-2 has Critical Role in Development of the Vasculature

Insight into the function of TIE-2 was gained by introduction of "excess" soluble TIE-2 receptorbody (TIE-2 RB) into a developing system. The potential ability of TIE-2 RB to bind, and thereby neutralize, available TIE-2 ligand could result in an observable disruption of normal vascular development and characterization of the ligand. To examine whether TIE-2 RB could be used to disrupt vascular development in early chick embryos, small pieces of a biologically resorbable foam were soaked with TIE-2 RB and inserted immediately beneath the chorioallantoic membrane at positions just lateral to the primitive embryo.

Early chicken embryos develop atop the yolk from a small disk of cells that is covered by the chorioallantoic membrane (CAM). The endothelial cells that will come to line the vasculature in the embryo arise from both extra- and intra-embryonic cell sources. Extra-embryonically-derived endothelial cells, which provide the major source of endothelial cells in the embryo, originate from accretions of mesenchyme that are situated laterally around the embryo-proper, just underneath the CAM. As these mesenchyme cells mature, they give rise to a common progenitor of both the endothelial and hematopoietic cell lineages, termed the hemangioblast. In turn, the hemangioblast gives rise to a mixed population of angioblasts (the endothelial cell progenitor) and hematoblasts (the pluripotential hematopoietic precursor). Formation of rudiments of the circulatory system begins when endothelial cell progeny segregate to form a one-cell-thick vesicle that surrounds the primitive blood cells. Proliferation and migration of these cellular components eventually produces a vast network of blood-filled microvessels under the CAM that will ultimately invade the embryo to join with limited, intra-embryonically-derived vascular elements.

Newly fertilized chicken eggs obtained from Spafas, Inc. (Boston, Mass.) were incubated at 99.5° F., 55% relative humidity. At about 24 hrs. of development, the egg shell was wiped down with 70% ethanol and a dentist's drill was used to make a 1.5 cm. hole in the blunt apex of each egg. The shell membrane was removed to reveal an air space directly above the embryo. Small rectangular pieces of sterile Gelfoam (Upjohn) were cut with a scalpel and soaked in equal concentrations of either TIE2- or EHK-1 receptorbody. EHK-1 receptorbody was made as set forth in Example 2 using the EHK-1 extracellular domain instead of the TIE-2 extracellular domain (Maisonpierre et al. (1993) Oncogene 8:3277–3288. Each Gelfoam piece absorbed approximately 6 mg of protein in 30 ml. Sterile watchmakers forceps were used to make a small tear in the CAM at a position several millimeters lateral to the primitive embryo. The majority of the piece of RB-soaked Gelfoam was inserted under the CAM and the egg shell was sealed over with a piece of adhesive tape. Other similarly-staged eggs were treated in parallel with RB of the unrelated, neuronally expressed receptor tyrosine kinase, EHK-1 (Maisonpierre et al. (1993) supra. Development was allowed to proceed for 4 days and then the embryos were examined by visual inspection. Embryos were removed by carefully breaking the shells in dishes of warmed PBS and carefully cutting away the embryo with surrounding CAM. Of 12 eggs treated with each RB, 6 TIE-2 RB and 5 EHK-1 RB treated embryos had developed beyond the stage observed at the start of the experiment. A dramatic difference was seen between these developed embryos. Those treated with EHK-1 RB appeared to have developed relatively normally. Four out of five EHK-1 embryos were viable as judged by the presence of a beating heart. Furthermore, the extra-embryonic vasculature, which is visually obvious due to the presence of red blood cells, was profuse and extended several centimeters laterally under the CAM. By contrast, those treated with TIE-2 RB were severely stunted, ranging from 2–5 mm. in diameter, as compared with more than 10 mm in diameter for the EHK-1 RB embryos. All of the TIE-2 RB treated embryos were dead and their CAMs were devoid of blood vessels. The ability of TIE-2 RB to block vascular development in the chicken demonstrates that TIE-2 ligand is necessary for development of the vasculature.

EXAMPLE 4

Identification of a TIE-2-Specific Binding Activity in Conditioned Medium from the ras Oncogene-transformed C2C12 Mouse Myoblast Cell Line Screening of ten-fold-concentrated cell-conditioned media (10× CCM) from various cell lines for the presence of soluble, TIE-2-specific binding activity (BIAcore) revealed binding activity in serum-free medium from oncogenic-ras-transformed C2C12 cells (C2C12-ras), RAT 2-ras (which is a ras transformed fibroblast cell line), human glioblastoma T98G and the human neuroblastoma cell line known as SHEP-1.

The C2C12-ras 10× CCM originated from a stably transfected line of C2C12 myoblasts that was oncogenically transformed by transfection with the T-24 mutant of H-ras by standard calcium phosphate-based methods. An SV40 based neomycin-resistance expression plasmid was physically linked with the ras expression plasmid in order to permit selection of transfected clones. Resulting G418-resistant ras-C2C12 cells were routinely maintained as a monolayer on plastic dishes in DMEM/glutamine/penicillin-streptomycin supplemented with 10% fetal calf serum (FCS). Serum-free C2C12-ras 10× CCM was made by plating the cells at 60% confluence in a serum free defined media for 12 hours (Zhan et al. (1986) Mol. Cell. Biol. 6: 3541–3544; Zhan et al. (1987) Oncogene 1: 369–376). The medium was discarded and replaced with fresh DMEM/Q/P-S for 24 hours. This medium was harvested and cells were re-fed fresh DMEM/Q/P-S, which was also harvested after a further 24 hours. These CCM were supplemented with the protease inhibitors PMSF (1 mM) and aprotinin (10 mg/ml), and ten-fold concentrated on sterile size-exclusion membranes (Amicon). TIE-2-binding activity could be neutralized by incubation of the medium with an excess of TIE-2 RB, but not by incubation with EHK-1 RB, prior to BIAcore analysis.

Binding activity of the 10× CCM was measured using biosensor technology (BIAcore) which monitors biomolecular interactions in real-time via surface plasmon resonance. Purified TIE-2 RB was covalently coupled through primary amines to the carboxymethyl dextran layer of a CM5 research grade sensor chip (Pharmacia Biosensor). The sensor chip surface was activated using a mixture of N-hydroxysuccinimide (NHS) and N-ethyl-N'-(3-dimethylaminopropyl)carbodiimide (EDC), followed by immobilization of TIE-2 RB (25 mg/mL, pH 4.5) and deactivation of unreacted sites with 1.0 M ethanolamine (pH 8.5). A negative control surface of the EHK-1 receptorbody was prepared in a similar manner.

The running buffer used in the system was HBS (10 mM Hepes, 3.4 mM EDTA, 150 mM NaCl, 0.005% P20 surfactant, pH 7.4). The 10× CCM samples were centrifuged for 15 min at 4° C. and further clarified using a sterile, low protein-binding 0.45 mm filter (Millipore; Bedford, Mass.). Dextran (2 mg/ml) and P20 surfactant (0.005%) were added to each CCM sample. Aliquots of 40 mL were injected across the immobilized surface (either TIE-2 or EHK-1) at a flow rate of 5 mL/min and the receptor binding was monitored for 8 min. The binding activity (resonance units, RU) was measured as the difference between a baseline value determined 30 s prior to the sample injection and a measurement taken at 30 s post-injection. Regeneration of the surface was accomplished with one 12-mL pulse of 3 M $MgCl_2$.

The instrument noise level is 20 RU; therefore, any binding activity with a signal above 20 RU may be interpreted as a real interaction with the receptor. For C2C12-ras conditioned media, the binding activities were in the range 60–90 RU for the TIE-2 RB immobilized surface. For the same samples assayed on a EHK-1 RB immobilized surface, the measured activities were less than 35 RU. Specific binding to the TIE-2 receptorbody was evaluated by incubating the samples with an excess of either soluble TIE-2 or EHK-1 RB prior to assaying the binding activity. The addition of soluble EHK-1 RB had no effect on the TIE-2 binding activity of any of the samples, while in the presence of soluble TIE-2 binding to the surface is two-thirds less than that measured in the absence of TIE-2. A repeat assay using >50× concentrated C2C12-ras CCM resulted in a four-fold enhancement over background of the TIE-2 specific binding signal.

EXAMPLE 5

C2C12-ras CCM Induces Tyrosine Phosphorylation of the TIE-2 Receptor

C2C12-ras 10× CCM was examined for its ability to induce tyrosine phosphorylation of TIE-2 in ABAE cells. Serum-starved ABAE cells were briefly incubated with C2C12-ras CCM, lysed and subjected to immunoprecipitation and Western analyses as described above. Stimulation of serum-starved ABAE cells with serum-free C2C12-ras 10× CCM was done as follows. The medium of ABAE cells starved as described above was removed and replaced with either defined medium or 10× CCM that had been pre-warmed to 37° C. After 10 minutes, the media were removed and the cells were twice rinsed on ice with an excess of chilled PBS supplemented with orthovanadate/NaF/benzamidine. Cell lysis and TIE-2-specific immunoprecipitation was done as described above.

ABAE cells incubated for 10 minutes with defined medium showed no induction of TIE-2 tyrosine phosphorylation, whereas incubation with C2C12-ras CCM stimulated at least a 100× increase in TIE-2 phosphorylation. This activity was almost totally depleted by pre-incubation of the C2C12-ras 10× CCM for 90 minutes at room temperature with 13 mg of TIE-2 RB coupled to protein G-Sepharose beads. Medium incubated with protein G Sepharose alone was not depleted of this phosphorylating activity.

EXAMPLE 6

Expression Cloning of TIE-2 Ligand

COS-7 cells were cultured in Dulbecco's modified Eagle's medium (DMEM) containing 10% fetal bovine serum (FBS), 1% each of penicillin and streptomycin (P/S) and 2 mM glutamine in an atmosphere of 5% $CO_2$. The mouse myoblast C2C12 ras cell line was cultured in Eagle's minimal essential medium (EMEM) with 10% FBS, (P/S) and 2 mM glutamine. Full length mouse TIE-2 ligand cDNA clones were obtained by screening a C2C12 ras cDNA library in the pJFE14 vector expressed in COS cells. This vector is a modified version of the vector $pSR_a$ (Takebe et al. 1988, Mol. Cell. Biol. 8:466–472). The library was created using the two BSTX1 restriction sites in the pJFE14 vector.

COS-7 cells were transiently transfected with either the pJFE14 library or control vector by the DEAE-dextran transfection protocol. Briefly, COS-7 cells were plated at a density of $1.0 \times 10^6$ cells/100 mm plate 24 hours prior to transfection. For transfection, the cells were cultured in serum-free DMEM containing 400 μg/ml of DEAE-dextran, 1 μM chloroquine, and 2 mM glutamine, and 1 μg of the appropriate DNA for 3–4 hours at 37° C. in an atmosphere of 5% $CO_2$. The transfection media was aspirated and replaced with PBS with 10% DMSO for 2–3 min. Following this DMSO "shock", the COS-7 cells were placed into DMEM with 10% FBS, 1% each of penicillin and streptomycin, and 2 mM glutamine for 48 hours.

Because the TIE-2 ligand is secreted it was necessary to permeabilize the cells to detect binding of the receptorbody probe to the ligand. Two days after transfection the cells were rinsed with PBS and then incubated with PBS containing 1.8% formaldehyde for 15–30 min. at room temperature. Cells were then washed with PBS and incubated for 15 min. with PBS containing 0.1% Triton X-100 and 10% Bovine Calf Serum to permeabilize the cells and block non-specific binding sites.

The screening was conducted by direct localization of staining using a TIE-2 receptorbody (RB), which consisted of the extracellular domain of TIE-2 fused to the IgG1 constant region. This receptorbody was prepared as set forth in Example 2. A 100 mm dish of transfected, fixed and permeabilized COS cells was probed by incubating them for 30 min with TIE-2 RB. The cells were then washed twice with PBS and incubated for an additional 30 min with PBS/10% Bovine Calf Serum/anti-human IgG-alkaline phosphatase conjugate. After three PBS washes, cells were incubated in alkaline-phosphatase substrate for 30–60 min. The dish was then inspected microscopically for the presence of stained cells. For each stained cell, a small area of cells including the stained cell was scraped from the dish using a plastic pipette tip and plasmid DNA was then rescued and used to electroporate bacterial cells. Single bacterial colonies resulting from the electroporation were picked and plasmid DNA prepared from these colonies was used to transfect COS-7 cells which were probed for TIE-2 ligand expression as evidenced by binding to TIE-2 receptorbodies. This allowed identification of single clones coding for TIE-2 ligand. Confirmation of TIE-2 ligand expression was obtained by phosphorylation of the TIE-2 receptor using the method set forth in Example 5. A plasmid clone encoding the TIE-2 ligand was deposited with the ATCC on Oct. 7, 1994 and designated as "pJFE14 encoding TIE-2 ligand" under ATCC Accession No. 75910.

EXAMPLE 7

Isolation and Sequencing of Full Length cDNA Clone Encoding Human TIE-2 Ligand

A human fetal lung cDNA library in lambda gt-10 was obtained from Clontech Laboratories, Inc. (Palo Alto, Calif.). Plaques were plated at a density of $1.25 \times 10^6/20 \times 20$ cm plate, and replica filters taken following standard procedures (Sambrook, et al. supra).

Isolation of human tie-2 ligand clones was carried out as follows. A 2.2 kb XhoI fragment from the deposited tie-2 ligand clone (ATCC NO. 75910—see Example 6 above) was labeled by random priming to a specific activity of approximately $5 \times 10^8$ cpm/ng. Hybridization was carried out at 65° C. in hybridization solution containing 0.5 mg/ml salmon sperm DNA. The filters were washed at 65° C. in 2×SSC, 0.1% SDS and exposed to Kodak XAR-5 film overnight at −70° C. Positive phage were plaque purified. High titre phage lysates of pure phage were used for isolation of DNA via a Qiagen column using standard techniques (Qiagen, Inc., Chatsworth, Calif., 1995 catalog, pp 36). Phage DNA was digested with EcoRI to release the cloned cDNA fragment for subsequent subcloning. A lambda phage vector containing human tie-2 ligand DNA was deposited with the ATCC on Oct. 26, 1994 under the designation lgt10 encoding htie-2 ligand 1 (ATCC Accession No. 75928). Phage DNA may be subjected directly to DNA sequence analysis by the dideoxy chain termination method (Sanger, et al., 1977, Proc. Natl. Acad. Sci. U.S.A. 74: 5463–5467).

Subcloning of the human tie-2 ligand DNA into a mammalian expression vector may be accomplished as follows. The clone lgt10 encoding htie-2 ligand 1 contains an EcoRI site located 490 base pairs downstream from the start of the coding sequence for the human TIE-2 ligand. The coding region may be excised using unique restriction sites upstream and downstream of the initiator and stop codons respectively. For example, an SpeI site, located 70 bp 5' to the initiator codon, and a Bpu1102i (also known as BlpI) site, located 265 bp 3' to the stop codon, may be used to excise the complete coding region. This may then be subcloned into the pJFE14 cloning vector, using the XbaI (compatible to the SpeI overhang) and the PstI sites (the PstI and Bpu1102i sites are both made blunt ended).

The coding region from the clone lgt10 encoding htie-2 ligand 1 was sequenced using the ABI 373A DNA sequencer and Taq Dideoxy Terminator Cycle Sequencing Kit (Applied Biosystems, Inc., Foster City, Calif.). The nucleotide and deduced amino acid sequence of human TIE-2 ligand from the clone lgt10 encoding htie-2 ligand 1 is shown in SEQ ID NOs:1–2.

In addition, full length human tie-2 ligand cDNA clones were obtained by screening a human glioblastoma T98G cDNA library in the pJFE14 vector. Clones encoding human TIE-2 ligand were identified by DNA hybridization using a 2.2 kb XhoI fragment from the deposited tie-2 ligand clone (ATCC NO. 75910) as a probe (see Example 6 above). The coding region was sequenced using the ABI 373A DNA sequencer and Taq Dideoxy Terminator Cycle Sequencing Kit (Applied Biosystems, Inc., Foster City, Calif.). This sequence was nearly identical to that of clone lgt10 encoding htie-2 ligand 1. As shown in SEQ ID NO:1, the clone lgt10 encoding htie-2 ligand 1 contains an additional glycine residue which is encoded by nucleotides 1114–1116. The coding sequence of the T98G clone does not contain this glycine residue but otherwise is identical to the coding sequence of the clone lgt10 encoding htie-2 ligand 1. SEQ ID NOs:3–4sets forth the nucleotide and deduced amino acid sequence of human TIE-2 ligand from the T98G clone.

EXAMPLE 8

Isolation and Sequencing of Human TIE-2 Ligand

A human fetal lung cDNA library in lambda gt-10 was obtained from Clontech Laboratories, Inc. (Palo Alto, Calif.). Plaques were plated at a density of $1.25 \times 10^6/20 \times 20$ cm plate, and replica filters taken following standard procedures. Duplicate filters were screened at low stringency (2×SSC, 55° C.) with probes made to the human TIE-2 ligand 1 sequence. One of the duplicate filters was probed with a 5' probe, encoding amino acids 25–265 of human TIE-2 ligand 1 (SEQ ID NO:1). The second duplicate filter was probed with a 3' probe, encoding amino acids 282–498 of human TIE-2 ligand 1 SEQ ID NO:1. Both probes were hybridized at 55° C. in hybridization solution containing 0.5 mg/ml salmon sperm DNA. Filters were washed in 2×SSC at 55° C. and exposed overnight to X-ray film. In addition, duplicate filters were also hybridized at normal stringency (2×SSC, 65° C.) to the full length coding probe of mouse TIE-2 ligand 1 (F3-15, XhoI insert). Three positive clones were picked that fulfilled the following criteria: i. hybridization had not been seen to the full length (mouse) probe at normal stringency, and ii. hybridization was seen at low stringency to both 5' and 3' probes. EcoRI digestion of phage DNA obtained from these clones indicated two independent clones with insert sizes of approximately 2.2 kb and approximately 1.8 kb. The 2.2 kb EcoRI insert was subcloned into the EcoRI sites of both pBluescript KS (Stratagene) and a mammalian expression vector suitable for use in COS cells. Two orientations were identified for the mammalian expression vector. The 2.2 kb insert in pBluescript KS was deposited with the ATCC on Dec. 9, 1994 and designated as pBluescript KS encoding human TIE 2 ligand 2. The start site of the TIE-2 ligand 2 coding sequence is approximately 355 base pairs downstream of the pBluescript EcoRI site.

COS-7 cells were transiently transfected with either the expression vector or control vector by the DEAE-dextran transfection protocol. Briefly, COS-7 cells were plated at a density of $1.0 \times 10^6$ cells/100 mm plate 24 hours prior to transfection. For transfection, the cells were cultured in serum-free DMEM containing 400 μg/ml of DEAE-dextran, 1 μM chloroquine, and 2 mM glutamine, and 1 μg of the appropriate DNA for 3–4 hours at 37° C. in an atmosphere of 5% $CO_2$. The transfection media was aspirated and replaced with phosphate-buffered saline with 10% DMSO for 2–3 min. Following this DMSO "shock", the COS-7 cells were placed into DMEM with 10% FBS, 1% each of penicillin and streptomycin, and 2 mM glutamine for 48 hours.

Because the TIE-2 ligand is secreted it was necessary to permeabilize the cells to detect binding of the receptorbody probe to the ligand. Transfected COS-7 cells were plated at a density of $1.0 \times 10^6$ cells/100 mm plate. The cells were rinsed with PBS and then incubated with PBS containing 1.8% formaldehyde for 15–30 min. at room temperature. Cells were then washed with PBS and incubated for 15 min. with PBS containing 0.1% Triton X-100 and 10% Bovine Calf Serum to permeabilize the cells and block non-specific binding sites.

The screening was conducted by direct localization of staining using a TIE-2 receptorbody, which consisted of the extracellular domain of TIE-2 fused to the IgG1 constant region. This receptorbody was prepared as set forth in Example 2. Transfected COS cells were probed by incubating them for 30 min with TIE-2 receptorbody. The cells were then washed twice with PBS, fixed with methanol, and then incubated for an additional 30 min with PBS/10% Bovine Calf Serum/anti-human IgG-alkaline phosphatase conjugate. After three PBS washes, cells were incubated in alkaline-phosphatase substrate for 30–60 min. The dish was then inspected microscopically for the presence of stained cells. Cells expressing one orientation of the clone, but not the other orientation, were seen to bind the TIE-2 receptorbody.

The coding region from the clone pBluescript KS encoding human TIE-2 ligand 2 was sequenced using the ABI 373A DNA sequencer and Taq Dideoxy Terminator Cycle Sequencing Kit (Applied Biosystems, Inc., Foster City, Calif.). The nucleotide and deduced amino acid sequence of human TIE-2 ligand from the clone pBluescript KS encoding human TIE-2 ligand 2 (SEQ ID NO:5).

EXAMPLE 9

TIE2 Ligand 1 is a Receptor Antagonist

Conditioned media from COS cells expressing either TIE-2 ligand 2 (TL2) or TIE-2 ligand 1 (TL1) were compared for their ability to activate TIE-2 receptors naturally present in human endothelial cell lines. Lipofectamine reagent (GIBCO-BRL, Inc.) and recommended protocols were used to transfect COS-7 cells with either the pJFE14 expression vector alone, pJFE14 vector containing the human TIE-2 ligand 1 cDNA, or with a pMT21 expression vector (Kaufman (1985) Proc. Natl. Acad. Sci. USA 82: 689–693) containing the human TIE-2 ligand 2 cDNA. COS media containing secreted ligands were harvested after three days and concentrated 20-fold by diafiltration (DIAFLO ultrafiltration membranes, Amicon, Inc.). The quantity of active TIE-2 ligand 1 and TIE-2 ligand 2 present in these media was determined and expressed as the amount (in resonance units, R.U.) of TIE-2 receptor specific binding activity measured by a BIAcore binding assay.

Northern (RNA) analyses revealed significant levels of TIE-2 transcripts in HAEC (Human Aortic Endothelial Cell) human primary endothelial cells (Clonetics, Inc.). Therefore, these cells were used to examine whether TIE-2 receptor is tyrosine-phosphorylated when exposed to COS media containing the TIE-2 ligands. HAEC cells were maintained in a complete endothelial cell growth medium (Clonetics, Inc.) that contained 5% fetal bovine serum, soluble bovine brain extract, 10 ng/ml human EGF, 1 mg/ml hydrocortisone, 50 mg/ml gentamicin and 50 ng/ml amphotericin-B. Assessment of whether TL1 and TL2 could activate TIE-2 receptor in the HAEC cells was done as follows. Semi-confluent HAEC cells were serum-starved for two hours in high-glucose Dulbecco's MEM with added L-glutamine and penicillin-streptomycin at 37° C. followed by replacement of the starvation medium with ligand-containing conditioned COS media for 7 minutes at 37° C. in a 5% CO2 incubator. The cells were subsequently lysed and TIE-2 receptor protein was recovered by immunoprecipitation of the lysates with TIE-2 peptide antiserum, followed by Western blotting with antiphosphotyrosine antiserum, exactly as described in Example 1. Phosphotyrosine levels on the TIE-2 receptor (TIE-2-R) were induced by treatment of HEAC cells with TIE-2 ligand 1 but not by TIE-2 ligand 2 conditioned COS media. MOCK is conditioned media from COS transfected with JFE14 empty vector.

Evidence that both TL1 and TL2 specifically bind to the TIE-2 receptor was demonstrated by using a BIAcore to assay the TIE-2 receptor specific binding activities in transfected COS media and by immunostaining of TL1- and TL2-expressing COS cells with TIE-2 receptorbodies.

Because TL2 did not activate the TIE-2 receptor, applicants set out to determine whether TL2 might be capable of serving as an antagonist of TL1 activity. HAEC phosphorylation assays were performed in which cells were first incubated with an "excess" of TL2, followed by addition of dilute TL1. It was reasoned that prior occupancy of TIE-2 receptor due to high levels of TL2 might prevent subsequent stimulation of the receptor following exposure to TL1 present at a limiting concentration.

Semi-confluent HAEC cells were serum-starved as described above and then incubated for 3 min., at 37° C. with 1–2 ml. of 20× COS/JFE14-TL2 conditioned medium. Control plates were treated with 20× COS/JFE14-only medium (MOCK). The plates were removed from the incubator and various dilutions of COS/JFE14-TL1 medium were then added, followed by further incubation of the plates for 5–7 min. at 37° C. Cells were subsequently rinsed, lysed and TIE-2-specific tyrosine phosphorylation in the lysates was examined by receptor immunoprecipitation and Western blotting, as described above. TL1 dilutions were made using 20× COS/JFE14-TL1 medium diluted to 2×, 0.5×, 0.1×, or 0.02× by addition of 20× COS/JFE14-alone medium. An assay of the initial 20× TL1 and 20× TL2 COS media using BIAcore biosensor technology indicated that they contained similar amounts of TIE-2-specific binding activities, i.e., 445 R.U. and 511 R.U. for TL1 and TL2, respectively. The results of the antiphosphotyrosine Western blot indicate that when compared to prior treatment of HAEC cells with MOCK medium, prior treatment of HAEC cells with excess TIE-2 ligand 2 antagonizes the subsequent ability of dilute TIE-2 ligand 1 to activate the TIE-2 receptor (TIE-2-R).

The ability of TL2 to competitively inhibit TL1 activation of the TIE-2-R was further demonstrated using the human cell hybrid line, EA.hy926. Experiments were performed in which unconcentrated COS cell media containing TL1 were mixed at varying dilutions with either MOCK- or TL2-conditioned media and placed on serum-starved EA.hy926 cell monolayers for 5 minutes at 37° C. The media were then removed, the cells were harvested by lysis and TIE-2-specific tyrosine phosphorylation was examined by Western blots, as described above. Treatment of the EA.hy926 cells with 1× COS-TL1 alone robustly activated the endogenous TIE-2-R in these cells, whereas 1× TL2 COS medium was inactive. However, mixture of TL1 with either MOCK or TL2 demonstrated that TL2 can block the activity of TL1 in a dose-dependent fashion. The ratio of TL2 (or MOCK) was decreased while the amount of TL1 in the mixture was correspondingly increased from 0.1× to 0.3×. At any of these mixture ratios the TL1:TL2 showed a reduced level of TIE-2-R phosphorylation compared to that of the corresponding TL1:MOCK. When the amount TL1 was held steady and the amount of TL2 (or MOCK) was decreased, however, a point was reached at which the TL2 in the sample was too dilute to effectively inhibit TL1 activity. The relative amount of each ligand present in these conditioned COS media could be estimated from their binding units as measured by the BIAcore assay and from Western blots of the COS media with ligand-specific antibodies. Consequently, we can infer that only a few-fold molar excess of TL2 is required to effectively block the activity of TL1 in vitro. This is significant because we have observed distinct examples in vivo (see Example 17) where TL2 mRNAs achieve considerable abundance relative to those of TL1. Thus, TL2 may be serving an important physiological role in effectively blocking signaling by the TIE-2-R at these sites.

Taken together these data confirm that, unlike TL1, TL2 is unable to stimulate endogenously expressed TIE-2-R on endothelial cells. Furthermore, at a few fold molar excess TL2 can block TL1 stimulation of the TIE-2 receptor, indicating that TL2 is a naturally occurring TIE-2 receptor antagonist.

EXAMPLE 10

Identification of TIE2-Specific Binding Activity

Binding activity of 10× CCM from the cell lines C2C12-ras, Rat2 ras, SHEP, and T98G, or COS cell supernatants after transfection with either human TIE-2 ligand 1 (hTL1) or human TIE-2 ligand 2 (hTL2) was measured using biosensor technology (BIAcore) which monitors biomolecular interactions in real-time via surface plasmon resonance (SPR). Purified rat or human TIE-2 RB was covalently coupled through primary amines to the carboxymethyl dextran layer of a CM5 research grade sensor chip). The sensor chip surface was activated using a mixture of N-hydroxysuccinimide (NHS) and N-ethyl-N'-(3-dimethylaminopropyl)carbodiimide (EDC), followed by immobilization of TIE-2 RB (25 mg/mL, pH 4.5) and deactivation of unreacted sites with 1.0 M ethanolamine (pH 8.5). In general, 9000–10000 RU of each receptorbody was coupled to the sensor chip.

The running buffer used in the system was HBS (10 mM Hepes, 150 mM NaCl, 0.005% P20 surfactant, pH 7.4). The samples were centrifuged for 15 min at 4° C. and further clarified using a sterile, low protein-binding 0.45 mm filter. Dextran (2 mg/ml) and P20 surfactant (0.005%) were added to each sample. Aliquots of 40 mL were injected across the immobilized surface (either rat or human TIE-2) at a flow rate of 5 mL/min and the receptor binding was monitored for 8 min. The binding activity (resonance units, RU) was measured as the difference between a baseline value determined 30 s prior to the sample injection and a measurement taken at 30 s post-injection. Regeneration of the surface was accomplished with one 15-mL pulse of 3 M $MgCl_2$.

The CCM samples (C2C12-ras, Rat2-ras, SHEP, T98G) were tested on the rat TIE-2 RB immobilized surface, while the recombinant hTL1 and hTL2 were tested on the human TIE-2 RB immobilized surface. In each case, specific binding to the TIE-2 receptorbody was evaluated by incubating the samples with 25 µg/ml of either soluble TIE-2 (rat or human) RB or trkB RB prior to assaying the binding activity. The addition of soluble trkB RB causes a slight decrease in the TIE-2 binding activity, while the addition of soluble TIE-2 RB significantly reduces the binding activity as compared to that measured in the absence of TIE-2 RB.

EXAMPLE 11

TIE2 RB Blocks Activation of the TIE2 Receptor by TIE2 Ligand 1

The applicants sought to determine whether soluble TIE-2 RB can serve as a competitive inhibitor to block activation of TIE-2 receptor by TIE-2 ligand 1 (TL1). To do this, TL1-containing COS media were preincubated with either TIE-2- or TrkB-RB and then compared for their ability to activate. TIE-2 receptors naturally present in a human endothelial cell line.

Conditioned COS media were generated from COS-7 cells transfected with either the pJFE14 expression vector alone (MOCK), or pJFE14 vector containing the human TIE-2 ligand 1 cDNA (TL1) and harvested as described in Example 9 hereinabove, with the exception that the media were sterile filtered but not concentrated. The quantity of TL1 was determined and expressed as the amount (in resonance units, R.U.) of TIE-2 receptor-specific binding activity measured by BIAcore binding assay.

Northern (RNA) analyses revealed significant levels of tie-2 transcripts in HUVEC (Human Umbilical Vein Endothelial Cell) human primary endothelial cells (Clonetics, Inc.). Therefore, these cells were used to examine whether TIE-2 receptor can be tyrosine-phosphorylated when exposed in the presence of TIE-2- or TrkB-RBs to COS media containing TL1. HUVEC cells were maintained at 37° C., 5% $CO_2$ in a complete endothelial cell growth medium (Clonetics, Inc.) that contained 5% fetal bovine serum, soluble bovine brain extract with 10 mg/ml heparin, 10 ng/ml human EGF, 1 ug/ml hydrocortisone, 50 mg/ml gentamicin and 50 ng/ml amphotericin-B. Assessment of whether TL1 could activate TIE-2 receptor in the HUVEC cells was done as follows. Confluent dishes of HUVEC cells were serum-starved for two-to-four hours in low-glucose Dulbecco's MEM at 37° C., 5% $CO_2$, followed by 10 minute incubation in starvation medium that included 0.1 mM sodium orthovanadate, a potent inhibitor of phosphotyrosine phosphatases. Meanwhile, conditioned COS media were preincubated 30 min. at room temperature with either TIE-2- or TrkB-RB added to 50 mg/ml. The starvation medium was then removed from the HUVEC dishes and incubated with the RB-containing COS media for 7 minutes at 37° C. HUVEC cells were subsequently lysed and TIE-2 receptor protein was recovered by immunoprecipitation with TIE-2 peptide antiserum, followed by Western blotting with an anti-phosphotyrosine antibody, as described in Example 1. Phosphotyrosine levels on the TIE-2 receptor were induced by treatment of HUVEC cells with TIE-2 ligand 1 (TL1) relative to that seen with control medium (MOCK) and this induction is specifically blocked by prior incubation with TIE-2-RB (TIE-2-Fc) but not by incubation with TrkB-RB (TrkB-Fc). These data indicate that soluble TIE-2 RB can serve as a selective inhibitor to block activation of TIE-2 receptor by TIE-2 ligand 1.

EXAMPLE 12

Construction of TIE3 LigandBodies

An expression construct was created that would yield a secreted protein consisting of the entire coding sequence of human TIE-2 ligand 1 (TL1) or TIE-2 ligand 2 (TL2) fused to the human immunoglobulin gamma-1 constant region (IgG1 Fc). These fusion proteins are called TIE-2 "ligandbodies" (TL1-Fc or TL2-Fc). The Fc portion of TL1-Fc and TL2-Fc was prepared as follows. A DNA fragment encoding the Fc portion of human IgG1 that spans from the hinge region to the carboxy-terminus of the protein, was amplified from human placental cDNA by PCR with oligonucleotides corresponding to the published sequence of human IgG1; the resulting DNA fragment was cloned in a plasmid vector. Appropriate DNA restriction fragments from a plasmid encoding full-length TL1 or TL2 and from the human IgG1 Fc plasmid were ligated on either side of a short PCR-derived fragment that was designed so as to fuse, in-frame, TL1 or TL2 with human IgG1 Fc protein-coding sequences.

Milligram quantities of TL2-Fc were obtained by cloning the TL2-Fc DNA fragment into the pVL1393 baculovirus vector and subsequently infecting the *Spodoptera frugiperda* SF-21AE insect cell line. Alternatively, the cell line SF-9 (ATCC Accession No. CRL-1711) or the cell line BTI-TN-5b1-4 may be used. DNA encoding the TL2-Fc was cloned as an Eco RI-NotI fragment into the baculovirus transfer plasmid pVL1393. Plasmid DNA was recombined into viral DNA by mixing 3 mg of plasmid DNA with 0.5 mg of Baculo-Gold DNA (Pharminigen), followed by introduction into liposomes using 30 mg Lipofectin (GIBCO-BRL). DNA-liposome mixtures were added to SF-21AE cells ($2\times10^6$ cells/60 mm dish) in TMN-FH medium (Modified Grace's Insect Cell Medium (GIBCO-BRL) for 5 hours at 27° C., followed by incubation at 27° C. for 5 days in TMN-FH medium supplemented with 5% fetal calf serum. Tissue culture medium was harvested for plaque purification of recombinant viruses, which was carried out using methods previously described except that the agarose overlay contained 125 mg/mL X-gal (5-bromo-4-chloro-3-indolyl-b-D-galactopyranoside; GIBCO-BRL). After 5 days of incubation at 27° C., non-recombinant plaques were scored by positive chromogenic reaction to the X-gal substrate, and their positions marked. Recombinant plaques were then visualized by addition of a second overlay containing 100 mg/mL MTT. Putative recombinant virus plaques were picked by plug aspiration, and purified by multiple rounds of plaque isolation to assure homogeneity. Virus stocks were generated by serial, low-multiplicity passage of plaque-purified virus. Low passage stocks of one virus clone (vTL2-Fc Clone #7) were produced.

SF-21AE cells were cultured in serum-free medium (SF-900 II, Gibco BRL) containing 1× antibiotic/antimycotic solution (Gibco BRL) and 25 mg/L Gentamycin (Gibco BRL). Pluronic F-68 was added as a surfactant to a final concentration of 1 g/L. Cultures (4 L) were raised in a bioreactor (Artisan Cell Station System) for at least three days prior to infection. Cells were grown at 27° C., with gassing to 50% dissolved oxygen, at a gas flow rate of 80 mL/min (aeration at a sparge ring). Agitation was by means of a marine impeller at a rate of 100 rpm. Cells were harvested in mid-logarithmic growth phase (~$2\times10^6$ cells/mL), concentrated by centrifugation, and infected with 5 plaque forming units of vTL2-Fc per cell. Cells and inoculum were brought to 400 mL with fresh medium, and virus was adsorbed for 2 hours at 27° C. in a spinner flask. The culture was then resuspended in a final volume of 8 L with fresh serum-free medium, and the cells incubated in the bioreactor as previously described.

Culture medium from vTL2-Fc-infected SF21AE cells were collected by centrifugation (500× g, 10 minutes) at 72 hours post-infection. Cell supernatants were brought to pH 8 with NaOH. EDTA was added to a final concentration of 10 mM and the supernatant pH was readjusted to 8. Supernatants were filtered (0.45 mm, Millipore) and loaded on a protein A column (protein A sepharose 4 fast flow or HiTrap protein A, both from Pharmacia). The column was washed with PBS containing 0.5 M NaCl until the absorbance at 280 nm decreased to baseline. The column was washed in PBS and eluted with 0.5 M acetic acid. Column fractions were immediately neutralized by eluting into tubes containing 1 M Tris pH 9. The peak fractions containing the TL2-Fc were pooled and dialyzed versus PBS.

EXAMPLE 13

Expression of TIE1, TIE2, TL1, and TL2 in Renal Cell Carcinoma

In situ hybridization experiments were performed on human renal cell carcinoma tumor tissue using TIE-1, TIE-2, TL1, and TL2 cDNA probes. TIE-2, TIE-1, TL1, and TL2 expression were all up-regulated in the tumor vasculature. Ligand expression appeared to be localized to either the vascular endothelial cells (TL2) or very near the vascular endothelial cells in the mesenchyme (TL1). VEGF has been shown to be dramatically up-regulated in this tumor tissue. Brown, et al. Am. J. Pathol. 143:1255–1262 (1993).

EXAMPLE 14

Expression of TIE1, TIE2, TL1, and TL2 in Wound Healing

In situ hybridization experiments were performed on cross-sectional tissue slices obtained from a rat cutaneous wound model using TIE-1, TIE-2, TL1, and TL2 cDNA probes. The wound healing model involves pressing a small cork bore against the skin of a rat and removing a small, cylindrical plug of skin. As healing begins at the base of the wound, a vertical slice of tissue is taken and used for in situ hybridization. In the tested tissue sample, TL1 and TL2 appeared to be slightly up-regulated by four days post-injury. In contrast to the slightly up-regulated expression of TL1 and TL2 in this tissue, VEGF expression, which may precede TL1 and TL2 expression, is dramatically up-regulated.

EXAMPLE 15

Expression of TIE Ligands in Fetal Liver and Thymus

Reverse transcription-PCR (RT-PCR) was performed on mouse E14.5 fetal liver and mouse E17.5 fetal thymus. Agarose gel electrophoresis of the RT-PCR products revealed that in the mouse fetal liver, TIE-2 ligand 1 (TL1)

RNA is enriched in the stromal region, but is absent in c-kit+TER119 hematopoietic precursor cells. In this same tissue, TIE-2 ligand 2 (TL2) RNA is enriched in the stromal cells, but absent in the hematopoietic precursor cells. In the mouse fetal thymus, TL2 is enriched in the stromal cells.

EXAMPLE 16

The TIE Receptor/Ligand System in Angiogenesis

Although the TIE-2/TIE ligand system appears to play an important role in endothelial cell biology, it has not been shown to play a significant, active role in the early to intermediate stages of vascularization (e.g. angioblast or endothelial cell proliferation and migration, tubule formation, and other early stage events in vascular modeling). In contrast to the receptors and factors known to mediate these aspects of vascular development, the temporally late pattern of expression of TIE-2 and TL1 in the course of vascularization suggests that this system plays a distinct role in the latter stages vascular development, including the structural and functional differentiation and stabilization of new blood vessels. The pattern of expression of TIE-2/TL1 also is consistent with a continuing role in the maintenance of the structural integrity and/or physiological characteristics of an established vasculature.

TIE Ligand 2 (TL2) appears to be a competitive inhibitor of TL1. The spatiotemporal characteristics of TL2 expression suggest that this single inhibitory molecule may play multiple, context-dependent roles essential to appropriate vascular development or remodeling (i.e., de-stabilization/de-differentiation of mature endothelial cells allowing the formation of new vessels from existing vasculature, inhibition of inappropriate blood vessel formation, and regression/involution of mature blood vessels).

EXAMPLE 17

Expression of TIE Ligands in the Female Reproductive System

Preliminary observations made in experiments examining the expression of the TIE receptors and ligands in the female reproductive system are consistent with the hypothesis the TL1 plays a role in neovascularization which temporally follows that of VEGF. The pattern of TL2 expression is also consistent with an antagonism of the action of TL1, and a specific role in vascular regression. To verify this, expression of relevant mRNAs can be examined following experimental induction of follicular and luteal development so that their temporal relation to various aspects of neovascularization/vascular regression can be more clearly defined (e.g. in conjunction with endothelial cell staining, vascular fills). Angiogenesis associated with follicular development and corpus luteum formation in staged ovaries of mature, female rats or following induced ovulation in pre-pubertal animals was followed using in situ hybridization. These studies revealed that VEGF, TL1 and TL2 are expressed in a temporally and spatially coordinate fashion with respect to the development and regression of vasculature in the ovary, specifically with respect to the establishment of the vascular system which is generated in the course of the conversion of an ovarian follicle to a corpus luteum (CL).

Briefly, VEGF expression increases in the follicular granule layer prior to its vascularization during the process of luteinization. During the process of CL formation, highest levels of VEGF expression are apparent in the center of the developing CL in the vicinity of luteinizing cells which are not yet vascularized. VEGF levels remain moderately high and are diffusely distributed in the developed CL. In contrast, noticeably enhanced expression of TIE-2 ligand 1 occurs only late in process of CL formation, after a primary vascular plexus has been established. Later, TL1 expression is apparent throughout the CL at which time the definitive capillary network of the CL has been established.

TL2 exhibits a more complex pattern of expression than either VEGF or TL1. In the developing CL, TL2 is expressed at highest levels at the front of the developing capillary plexus-between the central avascular region of the CL where VEGF expression is highest, and the most peripheral portion of the CL where TL1 expression is dominant and where the luteinization process is complete and the vascular system is most mature. TL2 also appears to be expressed at high levels in the follicular layer of large follicles which are undergoing atresia. While TL1 is also apparent in atretic follicles, VEGF is not expressed.

The pattern of expression described above is most consistent with a role for VEGF in the initiation of angiogenesis, with TL1 acting late in this process-for example in modeling and/or stabilization of the definitive vascular network. In contrast, TL2 is present both in areas of active expansion of a newly forming vascular network (during CL formation), and in regions which fail to establish a new vasculature and vascular regression is in progress (atretic follicles). This suggests a more dynamic and complex role for TL2, possibly involving destabilization of existing vasculature (necessary for regression) or developing vasculature (necessary for the dynamic modeling of newly forming vessels).

EXAMPLE 18

Receptorybody Binding and Ligand Binding and Competition Assays

A quantitative cell-free binding assay with two alternate formats has been developed for detecting either TIE-2 receptorbody binding or ligand binding and competition. In the receptorbody binding version of the assay, TIE-2 ligands (purified or partially purified; either TL1 or TL2) are coated onto an ELISA plate. Receptorbody at varying concentrations is then added, which binds to the immobilized ligand in a dose-dependent manner. At the end of 2 hours, excess receptorbody is washed away, then the amount bound to the plate is reported using a specific anti-human Fc antibody which is alkaline phosphatase tagged. Excess reporter antibody is washed away, then the AP reaction is developed using a colored substrate. The assay is quantitated using a spectrophotometer. This assay has been used to evaluate the integrity of TIE-2-IgG after injection into rats and mice. The assay can also be used in this format as a ligand competition assay, in which purified or partially-purified TIE ligands compete with immobilized ligand for receptorbody. In the ligand binding and competition version of the binding assay, TIE-2 ectodomain is coated onto the ELISA plate. The Fc-tagged fibrinogen-like domain fragments of the TIE ligands (TL1-fFc and TL2-fFc) then bind to the ectodomain, and can be detected using the same anti-human Fc antibody as described above. FIG. 1 shows an example of TL1-fFc binding to TIE-2 ectodomain. This version of the assay can also be used to quantitate levels of TL1-fFc in serum or other samples. If untagged ligand (again, either purified or unpurified) is added at the same time as the TL1-fFc, then a competition is set up between tagged ligand fragment and full-length ligand. The full-length ligand can displace the Fc-tagged fragment, and a competition curve is generated.

EXAMPLE 19

EA.hy926 Reporter Cell Line for TIE Ligand Activity

EA.hy926 is a cell hybrid line that was established by fusion of HUVEC with the human lung carcinoma-derived line, A549 (Edgell et al. (1983) Proc. Natl. Acad. Sci. (USA) 80:3734–3737). EA.hy926 cells have been found to express significant levels of TIE-2 receptor protein with low basal phosphotyrosine levels. The density at which EA.hy926 cells are passaged prior to their use for receptor assays, as well as their degree of confluency at the time of assay, can affect TIE-2 receptor abundance and relative inducibility in response to treatment with ligand. By adopting the following regimen for growing these cells the EA.hy926 cell line can be used as a dependable system for assay of TIE-2 ligand activities.

EA.hy926 cells are seeded at $1.5 \times 10^6$ cells in T-75 flasks (Falconware) and re-fed every other day with high-glucose Dulbecco's MEM, 10% fetal bovine serum, L-glutamine, penicillin-streptomycin, and 1× hypoxanthine-aminopterin-thymidine (HAT, Gibco/BRL). After three to four days of growth, the cells are passaged once again at $1.5 \times 10^6$ cells per T-75 flask and cultured an additional three to four days. For phosphorylation assays, cells prepared as described above were serum-starved by replacement of the culture medium with high-glucose DMEM and incubation for 2–3 hours at 37° C. This medium was aspirated from the flask and samples of conditioned media or purified ligand were added to the flask in a total volume of 1.5 ml followed by incubation at 37° C. for 5 minutes. Flasks were removed from the incubator and placed on a bed of ice. The medium was removed and replaced with 1.25 ml Lysis Buffer containing 1% nonidet P-40, 0.5% sodium deoxycholate, 0.1% SDS in 20 mM Tris, pH 7.6, 150 mM NaCl, 50 mM NaF, 1 mM sodium orthovanadate, 5 mM benzamidine, and 1 mM EDTA containing the protease inhibitors PMSF, aprotinin, and leupeptin. After 10 minutes on ice to allow membrane solubilization, plates were scraped and cell lysates were clarified by microcentrifugation at top speed for 10 minutes at 4° C. TIE-2 receptor was immunoprecipitated from the clarified supernatant by incubation in the cold with an anti-TIE-2 polyclonal antiserum and Protein G-conjugated Sepharose beads. The beads were washed three times with cold cell lysis buffer and boiled 5 minutes in Laemmli sample buffer, which was then loaded on 7.5% SDS-polyacrylamide gels. Resolved proteins were electrotransferred to PVDF (Lamblia-P) membrane and then subjected to Western blot analysis using anti-phosphotyrosine antibody and the ECL reagent. Subsequent comparison of total TIE-2 protein levels on the same blots was done by stripping the anti-phosphotyrosine antibody and reincubating with a polyclonal antiserum specific to the ectodomain of TIE-2.

EXAMPLE 20

Isolation and Sequence of Mammalian TIE Ligand 3

TIE ligand-3 (TL3) was cloned from a mouse BAC genomic library (Research Genetics) by hybridizing library duplicates, with either mouse TL1 or mouse TL2 probes corresponding to the entire coding sequence of those genes. Each copy of the library was hybridized using phosphate buffer at 55° C. overnight. After hybridization, the filters were washed using 2×SSC, 0.1% SDS at 60° C., followed by exposure of X ray film to the filters. Strong hybridization signals were identified corresponding to mouse TL1 and mouse TL2. In addition, signals were identified which weakly hybridized to both mouse TL1 and mouse TL2. DNA corresponding to these clones was purified, then digested with restriction enzymes, and two fragments which hybridized to the original probes were subcloned into a bacterial plasmid and sequenced. The sequence of the fragments contained two exons with homology to both mouse TL1 and mouse TL2. Primers specific for these sequences were used as PCR primers to identify tissues containing transcripts corresponding to TL3. A PCR band corresponding to TL3 was identified in a mouse uterus cDNA library in lambda gt-11. (Clontech).

Plaques were plated at a density of $1.25 \times 10^6/20 \times 20$ cm plate and replica filters taken following standard procedures (Sambrook et al. supra). Duplicate filters were screened at "normal" stringency (2×SSC, 65° C.) with a 200 bp PCR radioactive probe made to the mouse TL3 sequence. Hybridization was at 65° C. in a solution containing 0.5 mg/ml salmon sperm DNA. Filters were washed in 2×SSC at 65° C. and exposed for 6 hours to X-ray film. Two positive clones that hybridized in duplicate were picked. EcoRI digestion of phage DNA obtained from these clones indicated two independent clones with insert sizes of approximately 1.2 kb and approximately 2.2 kb. The 2.2kb EcoRI insert was subcloned into the EcoRI site of pBluescript KS (Stratagene). Sequence analysis showed that the longer clone was lacking an initiator methionine and signal peptide but otherwise encoded a probe homologous to both mouse TL1 and mouse TL2.

Two TL3-specific PCR primers were then synthesised as follows: US2: cctctgggctcgccagtttgttagg (SEQ ID NO:29) and US1: ccagctggcagatatcagg (SEQ ID NO:30). The following PCR reactions were performed using expression libraries derived from the mouse cell lines C2C12ras and MG87. In the primary PCR reaction, the specific primer US2 was used in conjunction with vector-specific oligos to allow amplification in either orientation. PCR was in a total volume of 100 ml using 35 cycles of 94° C., 1 min; 42° C. or 48° C. for 1 min; 72° C., 1 min. The secondary PCR reaction included the second specific primer, US1, which is contained within the primary PCR product, in conjunction with the same vector oligos. The secondary reactions were for 30 cycles, using the same temperatures and times as previous. PCR products were gel isolated and submitted for sequence analysis. On the basis of sequences obtained from a total of four independent PCR reactions using two different cDNA libraries, the 5' end of the TL3 sequence was deduced. Northern analysis revealed moderate to low levels of mouse TL3 transcript in mouse placenta. The expression of mouse TL3 consisted of a transcript of approximately 3 kb. The full length TL3 coding sequence is shown in SEQ ID NO:9.

The mouse TL3 sequence may then be used to obtain a human clone containing the coding sequence of human TL3 by hybridizing either a human genomic or cDNA library with a probe corresponding to mouse TL3 as has been described previously, for example, in Example 8 supra.

EXAMPLE 21

Isolation of Human TIE Ligand 4

TIE ligand-4 (TL4) was cloned from a mouse BAC genomic library (BAC HUMAN (II), Genome Systems Inc.) by hybridizing library duplicates, with either a human TL1 radioactive probe corresponding to the entire fibrinogen coding sequence of TL1 (nucleotides 1153 to 1806 SEQ ID NO:1) or a mouse TL3 radioactive probe corresponding to a segment of 186 nucleotides from the fibrinogen region of mouse TL3 (nucleotides 1307 to 1492 SEQ ID NO:9). Each probe was labeled by PCR using exact oligonucleotides and standard PCR conditions, except that dCTP was replaced by $P^{32}$dCTP. The PCR mixture was then passed through a gel filtration column to separate the probe from free $p^{32}$ dCTP. Each copy of the library was hybridized using phosphate buffer, and radiactive probe at 55° C. overnight using standard hybridization conditions. After hybridization, the filters were washed using 2×SSC, 0.1% SDS at 55° C., followed by exposure of X ray film. Strong hybridization signals were observed corresponding to human TL1. In addition, signals were identified which weakly hybridized to both human TL1 and mouse TL3. DNA corresponding to these clones was purified using standard procedures, then digested with restriction enzymes, and one fragment which hybridized to the original probes was subcloned into a bacterial plasmid and sequenced. The sequence of the fragments contained one exon with homology to both human TL1 and mouse TL3 and other members of the TIE ligand family. Primers specific for these sequences may be used as PCR primers to identify tissues containing transcripts corresponding to TL4.

The complete sequence of human TL4 may be obtained by sequencing the full BAC clone contained in the deposited bacterial cells. Exons may be identified by homology to known members of the TIE-ligand family such as TL1, TL2 and TL3. The full coding sequence of TL4 may then be determined by splicing together the exons from the TL4 genomic clone which, in turn, may be used to produce the TL4 protein. Alternatively, the exons may be used as probes to obtain a full length cDNA clone, which may then be used to produce the TL4 protein. Exons may also be identified from the BAC clone sequence by homology to protein domains such as fibrinogen domains, coiled coil domains, or protein signals such as signal peptide sequences. Missing exons from the BAC clone may be obtained by identification of contiguous BAC clones, for example, by using the ends of the deposited BAC clone as probes to screen a human genomic library such as the one used herein, by using the exon sequence contained in the BAC clone to screen a cDNA library, or by performing either 5' or 3' RACE procedure using oligonucleotide primers based on the TL4 exon sequences.

Identification of Additional TIE Ligand Family Members. The novel TIE ligand-4 sequence may be used in a rational search for additional members of the TIE ligand family using an approach that takes advantage of the existence of conserved segments of strong homology between the known family members.

The highly conserved regions among TL1, TL2 and TL3 may be used in designing degenerate oligonucleotide primers with which to prime PCR reactions using cDNAs. cDNA templates may be generated by reverse transcription of tissue RNAs using oligo d(T) or other appropriate primers. Aliquots of the PCR reactions may then be subjected to electrophoresis on an agarose gel. Resulting amplified DNA fragments may be cloned by insertion into plasmids, sequenced and the DNA sequences compared with those of all known TIE ligands.

Size-selected amplified DNA fragments from these PCR reactions may be cloned into plasmids, introduced into *E. coli* by electroporation, and transformants plated on selective agar. Bacterial colonies from PCR transformation may be analyzed by sequencing of plasmid DNAs that are purified by standard plasmid procedures.

Cloned fragments containing a segment of a novel TIE ligand may be used as hybridization probes to obtain full length cDNA clones from a cDNA library. For example, the human TL4 genomic sequence may be used to obtain a human cDNA clone containing the complete coding sequence of human TL4 by hybridizing a human cDNA library with a probe corresponding to human TL4 as has been described previously.

EXAMPLE 22

Cloning of the Full Coding Sequence of hTL4

Both 5' and 3' coding sequence from the genomic human TL-4 clone encoding human TIE ligand-4 (hTL-4 ATCC Accession No. 98095) was obtained by restriction enzyme digestion, Southern blotting and hybridization of the hTL-4 clone to coding sequences from mouse TL3, followed by subcloning and sequencing the hybridizing fragments. Coding sequences corresponding to the N-terminal and C-terminal amino acids of hTL4 were used to design PCR primers (shown below), which in turn were used for PCR amplification of TL4 from human ovary cDNA. A PCR band was identified as corresponding to human TL4 by DNA sequencing using the ABI 373A DNA sequencer and Taq Dideoxy Terminator Cycle Sequencing Kit (Applied Biosystems, Inc., Foster City, Calif.). The PCR band was then subcloned into vector pCR-script and several plasmid clones were analyzed by sequencing. The complete human TL4 coding sequence was then compiled and is shown in FIG. 23. In another embodiment of the invention, the nucleotide at position 569 is changed from A to G, resulting in an amino acid change from Q to R.

The PCR primers used as described above were designed as follows: hTL4atg 5'-gcatgctatctcgagccaccATGCTCTC-CCAGCTAGCCATGCTGCAG-3'(SEQ ID NO:27); hTL4not 5'-gtgtcgacgcggccgctctagatca-gacTTAGATGTCCAAAGGCCGTATCATCAT-3' (SEQ ID NO:28). Lowercase letters indicate "tail" sequences added to the PCR primers to facilitate cloning of the amplified PCR fragments.

EXAMPLE 23

Construction and Characterization of Modified TIE Ligands

A genetic analysis of TIE-2 ligand-1 and TIE-2 ligand-2 (TL1 and TL2) was undertaken t insight into a number of their observed properties. Although TL1 and TL2 share similar structural homology, they exhibit different physical and biological properties. The most prominent feature that distinguishes the two ligands is that although they both bind to the TIE-2 receptor, TL1 is an agonist while TL2 is an antagonist. Under non-reducing electrophoretic conditions both proteins exhibit covalent, multimeric structures. TL1 is produced as a mixture of disulfide cross-linked multimers, primarily trimers and higher order species, without any dimeric species. But TL2 is produced almost exclusively as a dimeric species. Also, while TL2 is produced well in most expression systems, TL1 is expressed poorly and is difficult to produce in large quantities. Finally, production and purification conditions also appear to predispose TL1 to inactivation by proteolytic cleavage at a site near the amino terminus.

To study these differences, several modified ligands were constructed as follows: Cysteine substitution, Investigations into what factors might be contributing to the different physical and biological properties of the two molecules revealed the presence in TL1 of a cysteine residue (Cys 265 SEQ ID NO:2; Cys 245 SEQ ID NO:8) preceding the fibrinogen-like domain in TL1 but absent in TL2—i.e., there was no corresponding cysteine residue in TL2. The Cys265 residue in TL1 is encoded by TGC and is located at about nucleotides 1102–1104 (SEQ ID NO:1) at the approximate junction between the coiled-coil and fibrinogen-like domains. Because cysteine residues are generally involved in disulfide bond formation, the presence of which can contribute to both the tertiary structure and biological properties of a molecule, it was thought that perhaps the presence of the Cys265 residue in TL1 might be at least partially responsible for the different properties of the two molecules.

To test this hypothesis, an expression plasmid was constructed which contained a mutation in TL1 in which the Cys (residue 265 SEQ ID NO:2; residue 245 SEQ ID NO:8) was replaced with an amino acid (serine) which does not form disulfide bonds. In addition to this TL1/Cys mutant, a second expression plasmid was constructed which mutated the approximately corresponding position in TL2 (Met247 SEQ ID NO:8) so that this residue was now a cysteine. Both non-mutated and mutated expression plasmids of TL1 and TL2 were transiently transfected into COS7 cells, cell supernatants containing the recombinant proteins were harvested, and samples were subjected to both reducing and non-reducing SDS/PAGE electrophoresis and subsequent Western blotting.

Western blots under non-reducing conditions of both non-mutated and mutated TL1 and TL2 proteins reveal that the TL1/CYS$^-$ mutant runs as a dimer much like TL2 and that the TL2/CYS+ mutant is able to form a trimer, as well as higher-order multimers, more like TL1. When the two mutant proteins were tested for their ability to induce phosphorylation in TIE-2 expressing cells, the TL1/CYS$^-$ mutant was able to activate the TIE-2 receptor, whereas the TL2/CYS$^+$ mutant was not.

Thus, when the cysteine residue (residue 265 SEQ ID NO:2; residue 245 SEQ ID NO:8) of TL1 was genetically altered to a serine, it was found that the covalent structure of TL1 became similar to that of TL2, i.e., primarily dimeric. The modified TL1 molecule still behaved as an agonist, thus the trimeric and/or higher order multimeric structure was not the determining factor giving TL1 the ability to activate. Although the removal of the cysteine did make a molecule with more desirable properties, it did not improve the production level of TL1.

Domain deletions. The nucleotide sequences encoding TL1 and TL2 share a genetic structure that can be divided into three domains, based on the amino acid sequences of the mature proteins. The last approximately 215 amino acid residues of each mature protein contains six cysteines and bears strong resemblance to a domain of fibrinogen. This region was thus denoted the "fibrinogen-like" domain or "F-domain." A central region of the mature protein containing approximately 205 residues had a high probability of assuming a "coiled-coil" structure and was denoted the "coiled-coil" domain or "C-domain." The amino-terminal approximately 55 residues of the mature protein contained two cysteines and had a low probability of having a coiled-coil structure. This region was designated the "N-terminal" domain or "N-domain." The modified ligands described herein are designated using a terminology wherein N=N-terminal domain, C=coiled-coil domain, F=fibrinogen-like domain and the numbers 1 and 2 refer to TL1 and TL2 respectively. Thus 1N indicates the N-terminal domain from TL1, 2F indicates the fibrinogen-like domain of TL2, and so forth.

In order to test whether the fibrinogen-like domain (F-domain) of the TIE-2 ligands contained TIE-2 activating activity, expression plasmids were constructed which deleted the coiled-coil and N-terminal domains, leaving only that portion of the DNA sequence encoding the F-domain (for TL1, beginning at about nucleotide 1159, amino acid residue Arg284 (SEQ ID NO:1–2); for TL2, corresponding to about nucleotide 1200, amino acid residue 282) (SEQ ID NO:5–6). This mutant construct was then transiently transfected into COS cells. The supernatant containing the recombinant protein was harvested. The TL1/F-domain mutant was tested for its ability to bind the TIE-2 receptor. The results showed that, as a monomer, the TL1/F-domain mutant was not able to bind TIE-2 at a detectable level.

But when the TL1/F-domain monomer was myc-tagged and subsequently clustered with an antibody directed against the myc tag, it exhibited detectable binding to TIE-2. However, the antibody-clustered TL1/F-domain mutant was not able to induce phosphorylation in a TIE-2 expressing cell line.

Thus it was determined that the F-domain of the TIE-2 ligands is involved in binding the receptor but that a truncation consisting of just the F-domain alone is not sufficient for receptor binding. This raised the possibility that the coiled-coil domain was responsible for holding together several fibrinogen-like domains, which might be essential for receptor binding. In an attempt to confirm this hypothesis, the F-domain was fused with the Fc section of human antibody IgG1. Because Fc sections dimerize upon expression by mammalian cells, these recombinant proteins mimicked the theoretical configuration of the F-domains were the native ligands to dimerize. This F-domain-Fc construct bound but failed to activate the receptor. Apparently, multimerization caused by other regions of the ligands is necessary to enable the ligands to bind the TIE receptor. In addition, some other factor outside of the F-domain must contribute to phosphorylation of the receptor.

Mutants were then constructed which were missing the fibrinogen-like domain, and therefore contained only the N-terminal and coiled-coil domains. They were not capable of binding to the receptor. To assess the role of the N-terminal domain in receptor binding and activation, the ligands were truncated to just their C- and F-domains and tagged with a FLAG tag at the N-terminus, creating constructs termed FLAG-1C1F and FLAG-2C2F. Although these molecules stained robustly in COS7 cells transfected transiently to express the TIE receptor, they failed to respond in a phosphorylation assay. Thus the N-domain does contain an essential factor for receptor activation although, as disclosed infra, the ability of chimeric molecule 2N2C1F to activate the receptor shows that even the N-domain of an inactive ligand can fill that role.

The differences in behavior between the myc-tagged F-domain truncation and the Fc-tagged F-domain truncation described previously suggested that the TIE ligands can only bind in dimeric or higher multimeric forms. Indeed, non-reducing SDS-PAGE showed that the TIE ligands exist naturally in dimeric, trimeric, and multimeric forms. That the FLAG-1C1F and FLAG-2C2F truncations can bind to the TIE-2 receptor without dimerization by a synthetic tag (such as Fc), whereas the F truncations cannot, suggests that the C-region is at least partly responsible for the aggregation of the F-domains.

Swapping constructs (chimeras). Applicants had noted that the level of production of TL1 in COS7 cells was approximately tenfold lower than production of TL2. Therefore, chimeras of TL1 and TL2 were constructed in an attempt to explain this difference and also to further characterize the agonist activity of TL1 as compared to the antagonist activity of TL2.

Four chimeras were constructed in which either the N-terminal domain or the fibrinogen domain was exchanged between TL1 and TL2 and were designated using the terminology described previously such that, for example, 1N1C2F refers to a chimera having the N-terminal and coiled-coil domains of TL1, together with the fibrinogen-like domain from TL2. The four chimeras were constructed as follows: chimera 1-1N1C2F; chimera 2-2N2C1F; chimera 3-1N2C2F; chimera 4-2N1C1F. The nucleotide and amino acid sequences of chimeras 1–4 are shown in SEQ ID NO:19–26.

Each chimera was inserted into a separate expression vector pJFE14. The chimeras were then transfected into COS7 cells, along with the empty pJFE14 vector, native TL1, and native TL2 as controls, and the culture supernatants were collected.

In order to determine how the swapping affected the level of expression of the ligands, a 1:5 dilution and a 1:50 dilution of the COS7 supernatants were dot-blotted onto nitrocellulose. Three ligands that contained the TL1 N-domain (i.e. native TL1, 1N2C2F and 1N1C2F) were then probed with a rabbit antibody specific to the N-terminus of TL1. Three ligands containing the TL2 N-domain, (i.e. native TL2, 2N1C1F and 2N2C1F) were probed with a rabbit antibody specific for the N-terminus of TL2. The results demonstrated that the COS7 cells were expressing any molecule containing the N-domain of TL2 at roughly ten times the level of any molecule containing the TL1 N-domain, regardless of the makeup of the rest of the protein. The conclusion was that the N-domain must principally control the level of expression of the ligand.

The next question addressed was the chimeras' ability or inability to activate the TIE-2 receptor. EAhy926 cells were challenged with the four chimeras, as well as TL1 as a positive control for phosphorylation and TL2 or an empty pJFE14-transfected COS7 cell supernatant as negative controls for phosphorylation. The cells were lysed, and the TIE-2 receptor was immunoprecipitated out of the cell lysate and run on an SDS-PAGE. The samples were Western blotted and probed with an anti-phosphotyrosine antibody to detect any receptors that had been phosphorylated. Surprisingly, only the constructs containing the TL1 fibrinogen-like domain (2N1C1F and 2N2C1F) could phosphorylate the TIE2 receptor. Thus, although the N-terminal region of TL1 is essential for activation, it can be replaced by the N-terminal region of TL2, i.e., the information that determines whether the ligand is an agonist or an antagonist is actually contained in the fibrinogen-like domain. Thus it was determined that the F-domain, in addition to binding the TIE-2 receptor, is responsible for the phosphorylation activity of TL1. Further, when TL2, an otherwise inactive molecule, was altered by replacing its F-domain with the TL1 F-domain, the altered TL2 acted as an agonist.

The 2N1C1F construct was somewhat more potent, however. The signal caused by chimera 2N1C1F appeared slightly stronger than that of chimera 2N2C1F, leading to speculation that the C-domain of TL1, though not crucial for phosphorylation, might enhance the potency of TL1. However, since the samples used for the phosphorylation assay were not normalized in terms of the concentration of ligand, it was possible that a stronger phosphorylation signal only indicated the presence of more ligand. The phosphorylation assay was therefore repeated with varying amounts of ligand to determine whether the active chimeras displayed different potencies. The concentration of ligand in the COS7 supernatants of ligand transfections was determined through BIAcore biosenser technology according to methods previously described (Stitt et al. (1995) Cell 80: 661–670). BIAcore measured the binding activity of a supernatant to the TIE-2 receptor in arbitrary units called resonance units (RU). Fairly good correlation between RU's and ligand concentration has been generally observed, with 400 RU of activity corresponding to about 1 μg of protein per mL of supernatant. Samples were diluted to concentrations of 100 RU, 20 RU, and 5 RU each and the phosphorylation assay was repeated. The results demonstrated that chimera 2N2C1F was clearly more potent than either the native TL1 or chimera 1N1C2F at the same concentrations.

Another interesting aspect of these exchange constructs is in their levels of expression. Each of the four chimeras was tested for its level of production in COS cells, its ability to bind to TIE2, and its ability to phosphorylate TIE2. The results of these experiments showed that chimeras 1 and 3 were produced at levels comparable to TL1, whereas chimeras 2 and 4 were produced at levels comparable to TL2. Thus a high level of protein production was correlated with the TL2 N-terminal domain. Additionally, when tested on endothelial EAhy926 cells, chimeras 2 and 4 were active, whereas 1 and 3 were not. Thus activity (phosphorylation of the receptor) correlates with the TL1 fibrinogen-like domain. Chimeras 2 and 4 therefore each had the desirable properties of high production levels as well as agonist activity.

Proteolytic resistant constructs. Based on the observation that a large fraction of TL1 preparations was often proteolytically cleaved near the N-terminus, it was proposed that an arginine residue located at position 49 of the mature protein (SEQ ID NO:8) was a candidate cleavage site that might be involved in the regulation of the protein's activity in vivo, and that replacing the arginine with a serine (R49→S) might increase the stability of the protein without necessarily affecting its activity. Such a mutant of TL1 was constructed and was found to be about as active as the native TL1 but did not exhibit resistance to proteolytic cleavage.

Combination mutants. The most potent of the chimeric constructs, 2N1C1F, was additionally altered so that the cysteine encoded by nucleotides 784–786 (SEQ ID NO:25) was converted to a serine. This molecule (denoted 2N1C1F (C246S)) was expressed well, potently activated the receptor, was resistant to proteolytic cleavage and was primarily dimeric, rather than higher-order multimeric. Thus the 2N domain appeared to confer protease resistance on the molecule. Finally, this molecule was further altered to eliminate the potentially protease sensitive site encoded by nucleotides 199–201 (SEQ ID NO:25), to give a molecule (denoted 2N1C1F (R51→S, C246→S)) which was expected to be activating, well expressed, dimeric, and protease resistant.

Table 1 summarizes the modified TIE-2 ligand constructs that were made and characterizes each of them in terms of ability to bind the TIE-2 receptor, ability to activate the TIE-2 receptor, the type of structure formed (monomer, dimer, etc.) and their relative production levels. Unmodified TL1 (plain) and TL2 (striped) are shown with the three domains as boxes. Thus striped boxes indicate domains from TL2. The cysteine located at position 245 of the mature TL1 protein is indicated by a "C." An "X" through the "C" indicates that that cysteine residue was substituted for by another amino acid as in, for example, the TL1 CYS⁻ mutant. Similarly, an "X" through the "R" in the last construct indicates the substitution for an Arg residue at position 49 of the mature TL1 protein. The "C" is present in one modified TL2 construct showing the TL2 CYS⁺ mutant. Constructs having Fc tails or flag tagging are also indicated.

Based upon the teachings herein, one of skill in the art can readily see that further constructs may be made in order to create additional modified and chimeric TIE-2 ligands which have altered properties. For example, one may create a construct comprised of the N-terminal domain of TL2 and the F-domain of TL1 fused with the Fc section of human antibody IgG1. This construct would be expected to bind and activate the TIE-2 receptor. Similarly, other constructs may be created using the teachings herein and are therefore considered to be within the scope of this invention.

Construction of Chimeras. Swapping constructs were inserted into a pJFE14 vector in which the XbaI site was changed to an AscI site. This vector was then digested with AscI and NotI yielding an AscI-NotI backbone. DNA fragments for the chimeras were generated by PCR using appropriate oligonucleotides. The FLAG-1C1F and FLAG-2C2F inserts were subcloned into a pMT21 vector backbone that had been digested with EcoRI and NotI. The "CF" truncations were obtained through PCR, and the FLAG tag and a preceding trypsin signalling sequence were constructed by annealing synthetic oligonucleotides.

Transfections. All constructs were transfected transiently into COS7 cells using either DEAE-Dextran or LipofectAMINE according to standard protocols. Cell cultures were harvested 3 days after the transfection and spun down at 1000 rpm for 1 minute, and the supernatants were transferred to fresh tubes and stored at −20° C.

Staining of FLAG-1C1F-Transfected and FLAG-2C2F-Transfected Cells. 6-well dishes of COS7 cells were transfected transiently with the TIE-2 receptor. The COS7 supernatant from various ligand tansfections was incubated on the cells for 30 minutes, followed by two washes with Phosphate Buffered Saline (PBS) without magnesium or calcium. The cells were fixed in −20 C. methanol for 3 minutes, washed once with PBS, and incubated with anti-FLAG M2 antibody (IBI;1:3000 dilution) in PBS/10% Bovine Calf Serum (BCS) for 30 minutes. The cells were washed once with PBS and incubated with goat anti-mouse IgG Alkaline Phosphatase (AP) conjugated antibody (Promega;1:1000) in PBS/10% BCS. The cells were washed twice with PBS and incubated with the phosphate substrate, BCIP/NBT, with 1 mM levamisole.

Phosphorylation Assays. Dilution of COS7 supernatants for the dose response study was done in the supernatants of COS7 cells transfected with the empty vector pJFE14. EA cells that naturally express the TIE-2 receptor were starved for >2 hours in serum-free medium, followed by challenge with the appropriate COS7 supernatant for 10 minutes at 37° C. in an atmosphere of 5% $CO_2$. The cells were then rinsed in ice-cold PBS and lysed with 1% NP40 lysis buffer containing protease inhibitors (10 μg/ml leupeptin, 10 μg/ml aprotinin, 1 mM PMSF) followed by immunoprecipitation with an antibody specific for the TIE-2 receptor. Samples were then subjected to immunoblot analysis, using anti pTyr antibodies.

Dot Blots. Samples were applied to a nitrocellulose membrane, which was blocked and probed with the appropriate antibodies.

DEPOSITS

The following have been deposited with the American Type Culture Collection, 12301 Parklawn Drive, Rockville, Md. 20852 in accordance with the Budapest Treaty. A plasmid clone encoding a TIE-2 ligand was deposited with the ATCC on Oct. 7, 1994 and designated as "pJFE14 encoding TIE-2 ligand" under ATCC Accession No.75910. Recombinant *Autographa californica* baculovirus encoding TIE-2 receptorbody was deposited with the ATCC on Oct. 7, 1994 and designated as "vTIE-2 receptorbody" under ATCC Accession No. VR2484. A lambda phage vector containing human tie-2 ligand DNA was deposited with the ATCC on Oct. 26, 1994 and designated as "lgt10 encoding htie-2 ligand 1" under ATCC Accession No. 75928. A plasmid clone encoding a second TIE-2 ligand was deposited with the ATCC on Dec. 9, 1994 and designated as "pBluescript KS encoding human TIE 2 ligand 2" under ATCC Accession No. 75963. *E. coli* strain DH10B containing plasmid pBeLoBac11 with a human TL-4 gene insert encoding human TIE ligand-4 was deposited with the ATCC on Jul. 2, 1996 and designated as "hTL-4" under ATCC Accession No. 98095.

The invention claimed is:

1. A fusion protein comprising a modified TIE-2 ligand 2 protein and a human immunoglobulin gamma-1 constant region (IgG1 Fc), wherein TIE-2 ligand 2 comprises an N-terminal domain, a coiled-coil domain, and C-terminal fibrinogen-like domain, and the modified TIE-2 ligand 2 protein has the N-terminal and coiled-coil domains deleted and the fibrinogen-like domain comprising amino acids 281–496 of SEQ ID NO:6.

2. A composition comprising the fusion protein of claim 1 and a pharmaceutically acceptable vehicle.

3. The composition of claim 2, wherein the fusion protein has a cytotoxic agent conjugated thereto.

4. The composition of claim 3, wherein the cytotoxic agent is a radioisotope or toxin.

* * * * *

SEQUENCE LISTING

```
<160> NUMBER OF SEQ ID NOS: 30

<210> SEQ ID NO 1
<211> LENGTH: 2149
<212> TYPE: DNA
<213> ORGANISM: Homo sapien

<400> SEQUENCE: 1
cagctgactc aggcaggctc catgctgaac ggtcacacag agaggaaaca ataaatctca      60
gctactatgc aataaatatc tcaagttttta acgaagaaaa acatcattgc agtgaaataa    120
aaaattttaa aattttagaa caaagctaac aaatggctag ttttctatga ttcttcttca    180
aacgctttct ttgaggggga aagagtcaaa caaacaagca gttttacctg aaataaagaa    240
ctagttttag aggtcagaag aaaggagcaa gttttgcgag aggcacggaa ggagtgtgct    300
ggcagtacaa tgcagttttt cctttccttt gctttcctcg ctgccattct gactcacata    360
gggtgcagca atcagcgccg aagtccagaa aacagtggga gaagatataa ccggattcaa    420
```

```
catgggcaat gtgcctacac tttcattctt ccagaacacg atggcaactg tcgtgagagt      480
acgacagacc agtacaacac aaacgctctg cagagagatg ctccacacgt ggaaccggat      540
ttctcttccc agaaacttca acatctggaa catgtgatgg aaaattatac tcagtggctg      600
caaaaacttg agaattacat tgtggaaaac atgaagtcgg agatggccca gatacagcag      660
aatgcagttc agaaccacac ggctaccatg ctggagatag aaccagcct cctctctcag       720 actgcagagc agaccagaaa gctgacagat gttgagaccc aggtactaaa tcaaacttct      780
cgacttgaga tacagctgct ggagaattca ttatccacct acaagctaga gaagcaactt      840
cttcaacaga caaatgaaat cttgaagatc catgaaaaaa acagtttatt agaacataaa      900
atcttagaaa tggaaggaaa acacaaggaa gagttggaca ccttaaagga agagaaagag      960
aaccttcaag gcttggttac tcgtcaaaca tatataatcc aggagctgga aaagcaatta     1020
aacagagcta ccaccaacaa cagtgtcctt cagaagcagc aactggagct gatggacaca     1080
gtccacaacc ttgtcaatct ttgcactaaa gaaggtgttt tactaaaggg aggaaaaaga     1140
gaggaagaga aaccatttag agactgtgca gatgtatatc aagctggttt taataaaagt     1200
ggaatctaca ctatttatat taataatatg ccagaaccca aaaaggtgtt ttgcaatatg     1260
gatgtcaatg ggggaggttg gactgtaata caacatcgtg aagatggaag tctagatttc     1320
caaagaggct ggaaggaata taaaatgggt tttggaaatc cctccggtga atattggctg     1380
gggaatgagt ttattttgc cattaccagt cagaggcagt acatgctaag aattgagtta      1440
atggactggg aagggaaccg agcctattca cagtatgaca gattccacat aggaaatgaa     1500
aagcaaaact ataggttgta tttaaaaggt cacactggga cagcaggaaa acagagcagc     1560
ctgatcttac acggtgctga tttcagcact aaagatgctg ataatgacaa ctgtatgtgc     1620
aaatgtgccc tcatgttaac aggaggatgg tggtttgatg cttgtggccc ctccaatcta     1680 aatgaatgt tctatactgc gggacaaaac catggaaaac tgaatgggat aaagtggcac     1740
tacttcaaag ggcccagtta ctccttacgt tccacaacta tgatgattcg acctttagat     1800
ttttgaaagc gcaatgtcag aagcgattat gaaagcaaca agaaatccg gagaagctgc     1860 caggtgagaa actgtttgaa aacttcagaa gcaaacaata ttgtctccct tccagcaata     1920
agtggtagtt atgtgaagtc accaaggttc ttgaccgtga atctggagcc gtttgagttc     1980
acaagagtct ctacttgggg tgacagtgct cacgtggctc gactatagaa aactccactg     2040
actgtcgggc tttaaaaagg gaagaaactg ctgagcttgc tgtgcttcaa actactactg     2100
gaccttattt tggaactatg gtagccagat gataaatatg gttaatttc                 2149
```

<210> SEQ ID NO 2
<211> LENGTH: 498
<212> TYPE: PRT
<213> ORGANISM: Homo sapien

<400> SEQUENCE: 2

Met Thr Val Phe Leu Ser Phe Ala Phe Leu Ala Ala Ile Leu Thr His
1               5                   10                  15

Ile Gly Cys Ser Asn Gln Arg Arg Ser Pro Glu Asn Ser Gly Arg Arg
            20                  25                  30

Tyr Asn Arg Ile Gln His Gly Gln Cys Ala Tyr Thr Phe Ile Leu Pro
        35                  40                  45

Glu His Asp Gly Asn Cys Arg Glu Ser Thr Thr Asp Gln Tyr Asn Thr
    50                  55                  60

Asn Ala Leu Gln Arg Asp Ala Pro His Val Glu Pro Asp Phe Ser Ser

```
            65                  70                  75                  80
Gln Lys Leu Gln His Leu Glu His Val Met Glu Asn Tyr Thr Gln Trp
                    85                  90                  95
Leu Gln Lys Leu Glu Asn Tyr Ile Val Glu Asn Met Lys Ser Glu Met
                    100                 105                 110
Ala Gln Ile Gln Gln Asn Ala Val Gln Asn His Thr Ala Thr Met Leu
                    115                 120                 125
Glu Ile Gly Thr Ser Leu Leu Ser Gln Thr Ala Glu Gln Thr Arg Lys
            130                 135                 140
Leu Thr Asp Val Glu Thr Gln Val Leu Asn Gln Thr Ser Arg Leu Glu
145                 150                 155                 160
Ile Gln Leu Leu Glu Asn Ser Leu Ser Thr Tyr Lys Leu Glu Lys Gln
                    165                 170                 175
Leu Leu Gln Gln Thr Asn Glu Ile Leu Lys Ile His Glu Lys Asn Ser
                    180                 185                 190
Leu Leu Glu His Lys Ile Leu Glu Met Glu Gly Lys His Lys Glu Glu
                    195                 200                 205
Leu Asp Thr Leu Lys Glu Glu Lys Glu Asn Leu Gln Gly Leu Val Thr
            210                 215                 220
Arg Gln Thr Tyr Ile Ile Gln Glu Leu Glu Lys Gln Leu Asn Arg Ala
225                 230                 235                 240
Thr Thr Asn Asn Ser Val Leu Gln Lys Gln Gln Leu Glu Leu Met Asp
                    245                 250                 255
Thr Val His Asn Leu Val Asn Leu Cys Thr Lys Glu Gly Val Leu Leu
                    260                 265                 270
Lys Gly Gly Lys Arg Glu Glu Lys Pro Phe Arg Asp Cys Ala Asp
                    275                 280                 285
Val Tyr Gln Ala Gly Phe Asn Lys Ser Gly Ile Tyr Thr Ile Tyr Ile
            290                 295                 300
Asn Asn Met Pro Glu Pro Lys Lys Val Phe Cys Asn Met Asp Val Asn
305                 310                 315                 320
Gly Gly Gly Trp Thr Val Ile Gln His Arg Glu Asp Gly Ser Leu Asp
                    325                 330                 335
Phe Gln Arg Gly Trp Lys Glu Tyr Lys Met Gly Phe Gly Asn Pro Ser
                    340                 345                 350
Gly Glu Tyr Trp Leu Gly Asn Glu Phe Ile Phe Ala Ile Thr Ser Gln
                    355                 360                 365
Arg Gln Tyr Met Leu Arg Ile Glu Leu Met Asp Trp Glu Gly Asn Arg
                    370                 375                 380
Ala Tyr Ser Gln Tyr Asp Arg Phe His Ile Gly Asn Glu Lys Gln Asn
385                 390                 395                 400
Tyr Arg Leu Tyr Leu Lys Gly His Thr Gly Thr Ala Gly Lys Gln Ser
                    405                 410                 415
Ser Leu Ile Leu His Gly Ala Asp Phe Ser Thr Lys Asp Ala Asp Asn
                    420                 425                 430
Asp Asn Cys Met Cys Lys Cys Ala Leu Met Leu Thr Gly Gly Trp Trp
                    435                 440                 445
Phe Asp Ala Cys Gly Pro Ser Asn Leu Asn Gly Met Phe Tyr Thr Ala
            450                 455                 460
Gly Gln Asn His Gly Lys Leu Asn Gly Ile Lys Trp His Tyr Phe Lys
465                 470                 475                 480
Gly Pro Ser Tyr Ser Leu Arg Ser Thr Thr Met Met Ile Arg Pro Leu
                    485                 490                 495
```

Asp Phe

<210> SEQ ID NO 3
<211> LENGTH: 2146
<212> TYPE: DNA
<213> ORGANISM: Homo sapien

<400> SEQUENCE: 3

| | | | | | |
|---|---|---|---|---|---|
| cagctgactc | aggcaggctc | catgctgaac | ggtcacacag | agaggaaaca | ataaatctca | 60 |
| gctactatgc | aataaatatc | tcaagtttta | acgaagaaaa | acatcattgc | agtgaaataa | 120 |
| aaaattttaa | aattttagaa | caaagctaac | aaatggctag | ttttctatga | ttcttcttca | 180 |
| aacgctttct | tgaggggga | aagagtcaaa | caaacaagca | gttttacctg | aaataaagaa | 240 |
| ctagttttag | aggtcagaag | aaaggagcaa | gttttgcgag | aggcacggaa | ggagtgtgct | 300 |
| ggcagtacaa | tgacagtttt | cctttccttt | gctttcctcg | ctgccattct | gactcacata | 360 |
| gggtgcagca | atcagcgccg | aagtccagaa | acagtgggaa | gaagatataa | ccggattcaa | 420 |
| catgggcaat | gtgcctacac | tttcattctt | ccagaacacg | atggcaactg | tcgtgagagt | 480 |
| acgacagacc | agtacaacac | aaacgctctg | cagagagatg | ctccacacgt | ggaaccggat | 540 |
| ttctcttccc | agaaacttca | acatctggaa | catgtgatgg | aaaattatac | tcagtggctg | 600 |
| caaaaacttg | agaattacat | tgtggaaaac | atgaagtcgg | agatggccca | gatacagcag | 660 |
| aatgcagttc | agaaccacac | ggctaccatg | ctggagatag | aaccagcct | cctctctcag | 720 |
| actgcagagc | agaccagaaa | gctgacagat | gttgagaccc | aggtactaaa | tcaaacttct | 780 |
| cgacttgaga | tacagctgct | ggagaattca | ttatccacct | acaagctaga | aagcaactt | 840 |
| cttcaacaga | caaatgaaat | cttgaagatc | catgaaaaaa | acagtttatt | agaacataaa | 900 |
| atcttagaaa | tggaaggaaa | acacaaggaa | gagttggaca | ccttaaagga | agagaaagag | 960 |
| aaccttcaag | gcttggttac | tcgtcaaaca | tatataatcc | aggagctgga | aaagcaatta | 1020 |
| aacagagcta | ccaccaacaa | cagtgtcctt | cagaagcagc | aactggagct | gatggacaca | 1080 |
| gtccacaacc | ttgtcaatct | ttgcactaaa | gaagttttac | taaagggagg | aaaaagagag | 1140 |
| gaagagaaac | catttagaga | ctgtgcagat | gtatatcaag | ctggttttaa | taaagtggaa | 1200 |
| atctacacta | tttatattaa | taatatgcca | gaacccaaaa | aggtgttttg | caatatggat | 1260 |
| gtcaatgggg | gaggttggac | tgtaatacaa | catcgtgaag | atggaagtct | agatttccaa | 1320 |
| agaggctgga | aggaatataa | aatgggtttt | ggaaatcct | ccggtgaata | ttggctgggg | 1380 |
| aatgagttta | ttttttgccat | taccagtcag | aggcagtaca | tgctaagaat | tgagttaatg | 1440 |
| gactgggaag | ggaaccgagc | ctattccacag | tatgacagat | tccacatagg | aaatgaaaag | 1500 |
| caaaactata | ggttgtattt | aaaaggtcac | actgggacag | caggaaaaca | gagcagcctg | 1560 |
| atcttcacacg | tgctgatttt | cagcactaaa | gatgctgata | atgacaactg | tatgtgcaaa | 1620 |
| tgtgccctca | tgttaacagg | aggatggtgg | tttgatgctt | gtggcccctc | caatctaaat | 1680 |
| ggaatgttct | atactgcggg | acaaaaccat | cgaaaactga | atgggataaa | gtggcactac | 1740 |
| ttcaaagggc | ccagttactc | cttacgttcc | acaactatga | tgattcgacc | tttagatttt | 1800 |
| tgaaagcgca | atgtcagaag | cgattatgaa | agcaacaaag | aaatccggag | aagctgccag | 1860 |
| gtgagaaact | gtttgaaaac | ttcagaagca | acaatattg | tctcccttcc | accaataagt | 1920 |
| ggtagttatg | tgaagtcacc | aaggttcttg | accgtgaatc | tggagccgtt | tgagttcaca | 1980 |
| agagtctcta | cttggggtga | cagtgctcac | gtggctcgac | tatagaaaac | tccactgact | 2040 |

-continued

```
gtcgggcttt aaaaagggaa gaaactgctg agcttgctgt gcttcaaact actactggac    2100
cttattttgg aactatggta gccagatgat aaatatggtt aatttc                   2146
```

<210> SEQ ID NO 4
<211> LENGTH: 497
<212> TYPE: PRT
<213> ORGANISM: Homo sapien

<400> SEQUENCE: 4

| | | | | | | | | | | | | | | |
|---|---|---|---|---|---|---|---|---|---|---|---|---|---|---|
| Met | Thr | Val | Phe | Leu | Ser | Phe | Ala | Phe | Leu | Ala | Ala | Ile | Leu | Thr | His |
| 1 | | | | 5 | | | | | 10 | | | | | 15 | |
| Ile | Gly | Cys | Ser | Asn | Gln | Arg | Arg | Ser | Pro | Glu | Asn | Ser | Gly | Arg | Arg |
| | | | 20 | | | | | 25 | | | | | 30 | | |
| Tyr | Asn | Arg | Ile | Gln | His | Gly | Gln | Cys | Ala | Tyr | Thr | Phe | Ile | Leu | Pro |
| | | | 35 | | | | | 40 | | | | | 45 | | |
| Glu | His | Asp | Gly | Asn | Cys | Arg | Glu | Ser | Thr | Thr | Asp | Gln | Tyr | Asn | Thr |
| | 50 | | | | | 55 | | | | | 60 | | | | |
| Asn | Ala | Leu | Gln | Arg | Asp | Ala | Pro | His | Val | Glu | Pro | Asp | Phe | Ser | Ser |
| 65 | | | | | 70 | | | | | 75 | | | | | 80 |
| Gln | Lys | Leu | Gln | His | Leu | Glu | His | Val | Met | Glu | Asn | Tyr | Thr | Gln | Trp |
| | | | | 85 | | | | | 90 | | | | | 95 | |
| Leu | Gln | Lys | Leu | Glu | Asn | Tyr | Ile | Val | Glu | Asn | Met | Lys | Ser | Glu | Met |
| | | | 100 | | | | | 105 | | | | | 110 | | |
| Ala | Gln | Ile | Gln | Gln | Asn | Ala | Val | Gln | Asn | His | Thr | Ala | Thr | Met | Leu |
| | | | 115 | | | | | 120 | | | | | 125 | | |
| Glu | Ile | Gly | Thr | Ser | Leu | Leu | Ser | Gln | Thr | Ala | Glu | Gln | Thr | Arg | Lys |
| | 130 | | | | | 135 | | | | | 140 | | | | |
| Leu | Thr | Asp | Val | Glu | Thr | Gln | Val | Leu | Asn | Gln | Thr | Ser | Arg | Leu | Glu |
| 145 | | | | | 150 | | | | | 155 | | | | | 160 |
| Ile | Gln | Leu | Leu | Glu | Asn | Ser | Leu | Ser | Thr | Tyr | Lys | Leu | Glu | Lys | Gln |
| | | | | 165 | | | | | 170 | | | | | 175 | |
| Leu | Leu | Gln | Gln | Thr | Asn | Glu | Ile | Leu | Lys | Ile | His | Glu | Lys | Asn | Ser |
| | | | 180 | | | | | 185 | | | | | 190 | | |
| Leu | Leu | Glu | His | Lys | Ile | Leu | Glu | Met | Glu | Gly | Lys | His | Lys | Glu | Glu |
| | | | 195 | | | | | 200 | | | | | 205 | | |
| Leu | Asp | Thr | Leu | Lys | Glu | Glu | Lys | Glu | Asn | Leu | Gln | Gly | Leu | Val | Thr |
| | 210 | | | | | 215 | | | | | 220 | | | | |
| Arg | Gln | Thr | Tyr | Ile | Ile | Gln | Glu | Leu | Glu | Lys | Gln | Leu | Asn | Arg | Ala |
| 225 | | | | | 230 | | | | | 235 | | | | | 240 |
| Thr | Thr | Asn | Asn | Ser | Val | Leu | Gln | Lys | Gln | Gln | Leu | Glu | Leu | Met | Asp |
| | | | | 245 | | | | | 250 | | | | | 255 | |
| Thr | Val | His | Asn | Leu | Val | Asn | Leu | Cys | Thr | Lys | Glu | Val | Leu | Leu | Lys |
| | | | 260 | | | | | 265 | | | | | 270 | | |
| Gly | Gly | Lys | Arg | Glu | Glu | Glu | Lys | Pro | Phe | Arg | Asp | Cys | Ala | Asp | Val |
| | | | 275 | | | | | 280 | | | | | 285 | | |
| Tyr | Gln | Ala | Gly | Phe | Asn | Lys | Ser | Gly | Ile | Tyr | Thr | Ile | Tyr | Ile | Asn |
| | 290 | | | | | 295 | | | | | 300 | | | | |
| Asn | Met | Pro | Glu | Pro | Lys | Lys | Val | Phe | Cys | Asn | Met | Asp | Val | Asn | Gly |
| 305 | | | | | 310 | | | | | 315 | | | | | 320 |
| Gly | Gly | Trp | Thr | Val | Ile | Gln | His | Arg | Glu | Asp | Gly | Ser | Leu | Asp | Phe |
| | | | | 325 | | | | | 330 | | | | | 335 | |
| Gln | Arg | Gly | Trp | Lys | Glu | Tyr | Lys | Met | Gly | Phe | Gly | Asn | Pro | Ser | Gly |
| | | | 340 | | | | | 345 | | | | | 350 | | |
| Glu | Tyr | Trp | Leu | Gly | Asn | Glu | Phe | Ile | Phe | Ala | Ile | Thr | Ser | Gln | Arg |

-continued

```
              355                 360                 365
Gln Tyr Met Leu Arg Ile Glu Leu Met Asp Trp Glu Gly Asn Arg Ala
    370                 375                 380

Tyr Ser Gln Tyr Asp Arg Phe His Ile Gly Asn Glu Lys Gln Asn Tyr
385                 390                 395                 400

Arg Leu Tyr Leu Lys Gly His Thr Gly Thr Ala Gly Lys Gln Ser Ser
                405                 410                 415

Leu Ile Leu His Gly Ala Asp Phe Ser Thr Lys Asp Ala Asp Asn Asp
                420                 425                 430

Asn Cys Met Cys Lys Cys Ala Leu Met Leu Thr Gly Gly Trp Trp Phe
                435                 440                 445

Asp Ala Cys Gly Pro Ser Asn Leu Asn Gly Met Phe Tyr Thr Ala Gly
    450                 455                 460

Gln Asn His Arg Lys Leu Asn Gly Ile Lys Trp His Tyr Phe Lys Gly
465                 470                 475                 480

Pro Ser Tyr Ser Leu Arg Ser Thr Thr Met Met Ile Arg Pro Leu Asp
                485                 490                 495

Phe
```

<210> SEQ ID NO 5
<211> LENGTH: 2282
<212> TYPE: DNA
<213> ORGANISM: Homo sapien

<400> SEQUENCE: 5

```
gaattcctgg gttggtgttt atctcctccc agccttgagg gagggaacaa cactgtagga      60
tctggggaga gaggaacaaa ggaccgtgaa agctgctctg taaaagctga cacagccctc     120
ccaagtgagc aggactgttc ttcccactgc aatctgacag tttactgcat gcctggagag     180
aacacagcag taaaaccag gtttgctact ggaaaaagag gaaagagaag actttcattg      240
acggacccag ccatggcagc gtagcagccc tgcgtttcag acggcagcag ctcgggactc     300
tggacgtgtg tttgccctca gtttgctaa gctgctggtt tattactgaa gaaagaatgt      360
ggcagattgt tttctttact ctgagctgtg atcttgtctt ggccgcagcc tataacaact     420
ttcggaagag catggacagc ataggaaaga agcaatatca ggtccagcat gggtcctgca     480
gctacacttt cctcctgcca gagatggaca actgccgctc ttcctccagc ccctacgtgt     540
ccaatgctgt gcagagggac gcgccgctcg aatacgatga ctcggtgcag aggctgcaag     600
tgctggagaa catcatggaa acaacactc agtggctaat gaagcttgag aattatatcc      660
aggacaacat gaagaaagaa atggtagaga tacagcagaa tgcagtacag aaccagacgg     720
ctgtgatgat agaaataggg acaaacctgt gaaccaaac agctgagcaa acgcggaagt      780
taactgatgt ggaagcccaa gtattaaatc agaccacgag acttgaactt cagctcttgg     840
aacactccct ctcgacaaac aaattggaaa acagattttt ggaccagacc agtgaaataa     900
acaaattgca agataagaac agtttcctag aaagaaggt gctagctatg aagacaagc      960
acatcatcca actacagtca ataaagaag agaaagatca gctacaggtg ttagtatcca    1020
agcaaaattc catcattgaa gaactagaaa aaaaatagt gactgccacg gtgaataatt    1080
cagttcttca aaagcagcaa catgatctca tggagacagt taataactta ctgactatga    1140
tgtccacatc aaactcagct aaggacccca ctgttgctaa gaagaacaa atcagcttca    1200
gagactgtgc tgaagtattc aaatcaggac acaccacaaa tggcatctac acgttaacat    1260
tcccctaattc tacagaagag atcaaggcct actgtgacat ggaagctgga ggaggcgggt    1320
```

-continued

```
ggacaattat tcagcgacgt gaggatggca gcgttgattt tcagaggact tggaaagaat   1380
ataaagtggg atttggtaac ccttcaggag aatattggct gggaaatgag tttgtttcgc   1440
aactgactaa tcagcaacgc tatgtgctta aaatacacct taaagactgg gaagggaatg   1500

aggcttactc attgtatgaa catttctatc tctcaagtga agaactcaat tataggattc   1560
accttaaagg acttacaggg acagccggca aaataagcag catcagccaa ccaggaaatg   1620
attttagcac aaaggatgga gacaacgaca aatgtatttg caaatgttca caaatgctaa   1680
caggaggctg gtggtttgat gcatgtggtc cttccaactt gaacggaatg tactatccac   1740
agaggcagaa cacaaataag ttcaacggca ttaaatggta ctactggaaa ggctcaggct   1800
attcgctcaa ggccacaacc atgatgatcc gaccagcaga tttctaaaca tcccagtcca   1860
cctgaggaac tgtctcgaac tattttcaaa gacttaagcc cagtgcactg aaagtcacgg   1920
ctgcgcactg tgtcctcttc caccacagag ggcgtgtgct cggtgctgac gggacccaca   1980
tgctccagat tagagcctgt aaactttatc acttaaactt gcatcactta acggaccaaa   2040
gcaagaccct aaacatccat aattgtgatt agacagaaca cctatgcaaa gatgaacccg   2100
aggctgagaa tcagactgac agtttacaga cgctgctgtc acaaccaaga atgttatgtg   2160
caagtttatc agtaaataac tggaaaacag aacacttatg ttatacaata cagatcatct   2220
tggaactgca ttcttctgag cactgtttat acactgtgta aatacccata tgtcctgaat   2280
tc                                                                  2282
```

<210> SEQ ID NO 6
<211> LENGTH: 496
<212> TYPE: PRT
<213> ORGANISM: Homo sapien

<400> SEQUENCE: 6

```
Met Trp Gln Ile Val Phe Phe Thr Leu Ser Cys Asp Leu Val Leu Ala
 1               5                  10                  15

Ala Ala Tyr Asn Asn Phe Arg Lys Ser Met Asp Ser Ile Gly Lys Lys
            20                  25                  30

Gln Tyr Gln Val Gln His Gly Ser Cys Ser Tyr Thr Phe Leu Leu Pro
        35                  40                  45

Glu Met Asp Asn Cys Arg Ser Ser Ser Ser Pro Tyr Val Ser Asn Ala
    50                  55                  60

Val Gln Arg Asp Ala Pro Leu Glu Tyr Asp Asp Ser Val Gln Arg Leu
65                  70                  75                  80

Gln Val Leu Glu Asn Ile Met Glu Asn Asn Thr Gln Trp Leu Met Lys
                85                  90                  95

Leu Glu Asn Tyr Ile Gln Asp Asn Met Lys Lys Glu Met Val Glu Ile
            100                 105                 110

Gln Gln Asn Ala Val Gln Asn Gln Thr Ala Val Met Ile Glu Ile Gly
        115                 120                 125

Thr Asn Leu Leu Asn Gln Thr Ala Glu Gln Thr Arg Lys Leu Thr Asp
    130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
            180                 185                 190
```

```
Lys Lys Val Ala Met Glu Asp Lys His Ile Ile Gln Leu Gln Ser
        195                 200                 205

Ile Lys Glu Lys Asp Gln Leu Gln Val Leu Val Ser Lys Gln Asn
    210                 215                 220

Ser Ile Ile Glu Glu Leu Glu Lys Lys Ile Val Thr Ala Thr Val Asn
225                 230                 235                 240

Asn Ser Val Leu Gln Lys Gln His Asp Leu Met Glu Thr Val Asn
            245                 250                 255

Asn Leu Leu Thr Met Met Ser Thr Ser Asn Ser Ala Lys Asp Pro Thr
            260                 265                 270

Val Ala Lys Glu Glu Gln Ile Ser Phe Arg Asp Cys Ala Glu Val Phe
        275                 280                 285

Lys Ser Gly His Thr Thr Asn Gly Ile Tyr Thr Leu Thr Phe Pro Asn
        290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
        340                 345                 350

Tyr Trp Leu Gly Asn Glu Phe Val Ser Gln Leu Thr Asn Gln Gln Arg
    355                 360                 365

Tyr Val Leu Lys Ile His Leu Lys Asp Trp Glu Gly Asn Glu Ala Tyr
    370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
                405                 410                 415

Ser Gln Pro Gly Asn Asp Phe Ser Thr Lys Asp Gly Asp Asn Asp Lys
        420                 425                 430

Cys Ile Cys Lys Cys Ser Gln Met Leu Thr Gly Gly Trp Trp Phe Asp
        435                 440                 445

Ala Cys Gly Pro Ser Asn Leu Asn Gly Met Tyr Tyr Pro Gln Arg Gln
    450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
                485                 490                 495

<210> SEQ ID NO 7
<211> LENGTH: 478
<212> TYPE: PRT
<213> ORGANISM: Homo sapien

<400> SEQUENCE: 7

Asn Gln Arg Arg Ser Pro Glu Asn Ser Gly Arg Arg Tyr Asn Arg Ile
1               5                   10                  15

Gln His Gly Gln Cys Ala Tyr Thr Phe Ile Leu Pro Glu His Asp Gly
            20                  25                  30

Asn Cys Arg Glu Ser Thr Thr Asp Gln Tyr Asn Thr Asn Ala Leu Gln
        35                  40                  45

Arg Asp Ala Pro His Val Glu Pro Asp Phe Ser Ser Gln Lys Leu Gln
    50                  55                  60

His Leu Glu His Val Met Glu Asn Tyr Thr Gln Trp Leu Gln Lys Leu
65                  70                  75                  80
```

```
Glu Asn Tyr Ile Val Glu Asn Met Lys Ser Glu Met Ala Gln Ile Gln
                85                  90                  95
Gln Asn Ala Val Gln Asn His Thr Ala Thr Met Leu Glu Ile Gly Thr
            100                 105                 110
Ser Leu Leu Ser Gln Thr Ala Glu Gln Thr Arg Lys Leu Thr Asp Val
        115                 120                 125
Glu Thr Gln Val Leu Asn Gln Thr Ser Arg Leu Glu Ile Gln Leu Leu
    130                 135                 140
Glu Asn Ser Leu Ser Thr Tyr Lys Leu Glu Lys Gln Leu Leu Gln Gln
145                 150                 155                 160
Thr Asn Glu Ile Leu Lys Ile His Glu Lys Asn Ser Leu Leu Glu His
                165                 170                 175
Lys Ile Leu Glu Met Glu Gly Lys His Lys Glu Leu Asp Thr Leu
                180                 185                 190
Lys Glu Glu Lys Glu Asn Leu Gln Gly Leu Val Thr Arg Gln Thr Tyr
            195                 200                 205
Ile Ile Gln Glu Leu Glu Lys Gln Leu Asn Arg Ala Thr Thr Asn Asn
        210                 215                 220
Ser Val Leu Gln Lys Gln Gln Leu Glu Leu Met Asp Thr Val His Asn
225                 230                 235                 240
Leu Val Asn Leu Cys Thr Lys Glu Gly Val Leu Leu Lys Gly Gly Lys
                245                 250                 255
Arg Glu Glu Glu Lys Pro Phe Arg Asp Cys Ala Asp Val Tyr Gln Ala
            260                 265                 270
Gly Phe Asn Lys Ser Gly Ile Tyr Thr Ile Tyr Ile Asn Asn Met Pro
        275                 280                 285
Glu Pro Lys Lys Val Phe Cys Asn Met Asp Val Asn Gly Gly Gly Trp
    290                 295                 300
Thr Val Ile Gln His Arg Glu Asp Gly Ser Leu Asp Phe Gln Arg Gly
305                 310                 315                 320
Trp Lys Glu Tyr Lys Met Gly Phe Gly Asn Pro Ser Gly Glu Tyr Trp
                325                 330                 335
Leu Gly Asn Glu Phe Ile Phe Ala Ile Thr Ser Gln Arg Gln Tyr Met
            340                 345                 350
Leu Arg Ile Glu Leu Met Asp Trp Glu Gly Asn Arg Ala Tyr Ser Gln
        355                 360                 365
Tyr Asp Arg Phe His Ile Gly Asn Glu Lys Gln Asn Tyr Arg Leu Tyr
    370                 375                 380
Leu Lys Gly His Thr Gly Thr Ala Gly Lys Gln Ser Ser Leu Ile Leu
385                 390                 395                 400
His Gly Ala Asp Phe Ser Thr Lys Asp Ala Asp Asn Asp Asn Cys Met
                405                 410                 415
Cys Lys Cys Ala Leu Met Leu Thr Gly Gly Trp Trp Phe Asp Ala Cys
            420                 425                 430
Gly Pro Ser Asn Leu Asn Gly Met Phe Tyr Thr Ala Gly Gln Asn His
        435                 440                 445
Gly Lys Leu Asn Gly Ile Lys Trp His Tyr Phe Lys Gly Pro Ser Tyr
    450                 455                 460
Ser Leu Arg Ser Thr Thr Met Met Ile Arg Pro Leu Asp Phe
465                 470                 475

<210> SEQ ID NO 8
<211> LENGTH: 480
```

<210> TYPE: PRT
<213> ORGANISM: Homo sapien

<400> SEQUENCE: 8

```
Ala Ala Tyr Asn Asn Phe Arg Lys Ser Met Asp Ser Ile Gly Lys Lys
 1               5                  10                  15

Gln Tyr Gln Val Gln His Gly Ser Cys Ser Tyr Thr Phe Leu Leu Pro
            20                  25                  30

Glu Met Asp Asn Cys Arg Ser Ser Ser Pro Tyr Val Ser Asn Ala
        35                  40                  45

Val Gln Arg Asp Ala Pro Leu Glu Tyr Asp Ser Val Gln Arg Leu
 50                  55                  60

Gln Val Leu Glu Asn Ile Met Glu Asn Asn Thr Gln Trp Leu Met Lys
 65                  70                  75                  80

Leu Glu Asn Tyr Ile Gln Asp Asn Met Lys Lys Glu Met Val Glu Ile
                85                  90                  95

Gln Gln Asn Ala Val Gln Asn Gln Thr Ala Val Met Ile Glu Ile Gly
            100                 105                 110

Thr Asn Leu Leu Asn Gln Thr Ala Glu Gln Thr Arg Lys Leu Thr Asp
            115                 120                 125

Val Glu Ala Gln Val Leu Asn Gln Thr Thr Arg Leu Glu Leu Gln Leu
 130                 135                 140

Leu Glu His Ser Leu Ser Thr Asn Lys Leu Glu Lys Gln Ile Leu Asp
145                 150                 155                 160

Gln Thr Ser Glu Ile Asn Lys Leu Gln Asp Lys Asn Ser Phe Leu Glu
                165                 170                 175

Lys Lys Val Leu Ala Met Glu Asp Lys His Ile Ile Gln Leu Gln Ser
            180                 185                 190

Ile Lys Glu Glu Lys Asp Gln Leu Gln Val Leu Val Ser Lys Gln Asn
            195                 200                 205

Ser Ile Ile Glu Glu Leu Glu Lys Lys Ile Val Thr Ala Thr Val Asn
            210                 215                 220

Asn Ser Val Leu Gln Lys Gln Gln His Asp Leu Met Glu Thr Val Asn
225                 230                 235                 240

Asn Leu Leu Thr Met Met Ser Thr Ser Asn Ser Ala Lys Asp Pro Thr
                245                 250                 255

Val Ala Lys Glu Glu Gln Ile Ser Phe Arg Asp Cys Ala Glu Val Phe
            260                 265                 270

Lys Ser Gly His Thr Thr Asn Gly Ile Tyr Thr Leu Thr Phe Pro Asn
            275                 280                 285

Ser Thr Glu Glu Ile Lys Ala Tyr Cys Asp Met Glu Ala Gly Gly Gly
        290                 295                 300

Gly Trp Thr Ile Ile Gln Arg Arg Glu Asp Gly Ser Val Asp Phe Gln
305                 310                 315                 320

Arg Thr Trp Lys Glu Tyr Lys Val Gly Phe Gly Asn Pro Ser Gly Glu
                325                 330                 335

Tyr Trp Leu Gly Asn Glu Phe Val Ser Gln Leu Thr Asn Gln Gln Arg
            340                 345                 350

Tyr Val Leu Lys Ile His Leu Lys Asp Trp Glu Gly Asn Glu Ala Tyr
            355                 360                 365

Ser Leu Tyr Glu His Phe Tyr Leu Ser Ser Glu Glu Leu Asn Tyr Arg
        370                 375                 380

Ile His Leu Lys Gly Leu Thr Gly Thr Ala Gly Lys Ile Ser Ser Ile
385                 390                 395                 400
```

| | | | | | | | | | | | |
|---|---|---|---|---|---|---|---|---|---|---|---|
|Ser|Gln|Pro|Gly|Asn|Asp|Phe|Ser|Thr|Lys|Asp|Gly Asn Asp Lys|
| | | |405| | | | |410| | |415|

| | | | | | | | | | | | |
|---|---|---|---|---|---|---|---|---|---|---|---|
|Cys|Ile|Cys|Lys|Cys|Ser|Gln|Met|Leu|Thr|Gly|Gly Trp Trp Phe Asp|
| | | |420| | | | |425| | |430|

| | | | | | | | | | | | |
|---|---|---|---|---|---|---|---|---|---|---|---|
|Ala|Cys|Gly|Pro|Ser|Asn|Leu|Asn|Gly|Met|Tyr|Tyr Pro Gln Arg Gln|
| | | |435| | | | |440| | |445|

| | | | | | | | | | | | |
|---|---|---|---|---|---|---|---|---|---|---|---|
|Asn|Thr|Asn|Lys|Phe|Asn|Gly|Ile|Lys|Trp|Tyr|Tyr Trp Lys Gly Ser|
| | | |450| | | | |455| | |460|

| | | | | | | | | | | | |
|---|---|---|---|---|---|---|---|---|---|---|---|
|Gly|Tyr|Ser|Leu|Lys|Ala|Thr|Thr|Met|Met|Ile|Arg Pro Ala Asp Phe|
|465| | | |470| | | |475| | |480|

<210> SEQ ID NO 9
<211> LENGTH: 1849
<212> TYPE: DNA
<213> ORGANISM: Homo sapien

<400> SEQUENCE: 9

```
ctgtcctggt acctgacaag accacctcac caccacttgg tctcagatgc tctgccagcc      60
agctatgcta ctagatggcc tcctcctgct ggccaccatg ctgcagccca gcacagagg      120
gccagaagcc ggtgggcacc gccagattca ccaggtccgg cgtggccagt gcagctacac     180
ctttgtggtg ccggagcctg atatctgcca gctggcgccg acagcggcgc ctgaggcttt     240
ggggggctcc aatagcctcc agagggactt gcctgcctcg aggctgcacc taacagactg     300
gcgagcccag agggcccagc gggcccagc tgtgagccag ctggagaaga tactagagaa      360
taacactcag tggctgctga agctggagca gtccatcaag gtgaacttga ggtcacacct     420
ggtgcaggcc cagcaggaca caatccagaa ccagacaact accatgctgg cactgggtgc     480
caacctcatg aaccagacca agctcagac ccacaagctg actgctgtgg aggcacaggt      540
cctaaaccag acattgcaca tgaagaccca aatgctggag aactcactgt ccaccaacaa     600
gctggagcgg cagatgctga tgcagagccg agagctgcag cggctgcagg tcgcaacag      660
ggccctggag accaggctgc aggcactgga agcacaacat caggcccagc ttaacagcct     720
ccaagagaag agggaacaac tgcacagtct cctgggccat cagaccggga ccctggctaa     780
cctgaagcac aatctgcacg ctctcagcag caattccagc tccctgcagc agcagcagca     840
gcaactgacg gagtttgtac agcgcctggt acggattgta gcccaggacc agcatccggt     900
ttccttaaag acacctaagc cagtgttcca ggactgtgca gagatcaagc gctccgggt      960
taataccagc ggtgtctata ccatctatga ccaacatg acaaagcctc tcaaggtgtt      1020
ctgtgacatg gagactgatg gaggtggctg gaccctcatc cagcaccggg aggatggaag    1080
cgtaaatttc cagaggacct gggaagaata caaagagggt tttggtaatg tggccagaga    1140
gcactggctg ggcaatgagg ctgtgcaccg cctcaccagc agaacggcct acttgctacg    1200
cgtggaactc atgactgggg aaggccgcca gacctccatc cagtatgaga cttccagct    1260
gggcagcgag aggcagcggt acagcctctc tgtgaatgac agcagcagtt cagcagggcg    1320
caagaacagc ctggctcctc agggcaccaa gttcagcacc aaagacatgg acaatgataa    1380
ctgcatgtgt aaatgtgctc agatgctgtc tggagggtgg tggtttgatg cctgtggcct    1440
ctccaacctc aatggcatct actattcagt tcatcagcac ttgcacaaga tcaatggcat    1500
ccgctggcac tacttccgag gcccagcta ctcactgcac ggcacacgca tgatgctgag    1560
gccaatgggt gcctgacaca cagccctgca gagactgatg ccgtaggagg attctcaacc    1620
caggtgactc tgtgcacgct gggccctgcc cagaaatcag tgcccagggc tcatcttgac    1680
```

-continued

```
attctggaac atcggaacca gcttaccttg cccctgaatt acaagaattc acctgcctcc    1740
ctgttgccct ctaattgtga aattgctggg tgcttgaagg cacctgcctc tgttggaacc    1800
atactctttc cccctcctgc tgcatgcccg ggaatccctg ccatgaact                1849
```

```
<210> SEQ ID NO 10
<211> LENGTH: 509
<212> TYPE: PRT
<213> ORGANISM: Homo sapien

<400> SEQUENCE: 10
```

```
Met Leu Cys Gln Pro Ala Met Leu Leu Asp Gly Leu Leu Leu Leu Ala
 1               5                  10                  15

Thr Met Ala Ala Ala Gln His Arg Gly Pro Glu Ala Gly Gly His Arg
            20                  25                  30

Gln Ile His Gln Val Arg Arg Gly Gln Cys Ser Tyr Thr Phe Val Val
        35                  40                  45

Pro Glu Pro Asp Ile Cys Gln Leu Ala Pro Thr Ala Ala Pro Glu Ala
    50                  55                  60

Leu Gly Gly Ser Asn Ser Leu Gln Arg Asp Leu Pro Ala Ser Arg Leu
65                  70                  75                  80

His Leu Thr Asp Trp Arg Ala Gln Arg Ala Gln Arg Ala Gln Arg Val
                85                  90                  95

Ser Gln Leu Glu Lys Ile Leu Glu Asn Asn Thr Gln Trp Leu Leu Lys
            100                 105                 110

Leu Glu Gln Ser Ile Lys Val Asn Leu Arg Ser His Leu Val Gln Ala
        115                 120                 125

Gln Gln Asp Thr Ile Gln Asn Gln Thr Thr Thr Met Leu Ala Leu Gly
    130                 135                 140

Ala Asn Leu Met Asn Gln Thr Lys Ala Gln Thr His Lys Leu Thr Ala
145                 150                 155                 160

Val Glu Ala Gln Val Leu Asn Gln Thr Leu His Met Lys Thr Gln Met
                165                 170                 175

Leu Glu Asn Ser Leu Ser Thr Asn Lys Leu Glu Arg Gln Met Leu Met
            180                 185                 190

Gln Ser Arg Glu Leu Gln Arg Leu Gln Gly Arg Asn Arg Ala Leu Glu
        195                 200                 205

Thr Arg Leu Gln Ala Leu Glu Ala Gln His Gln Ala Gln Leu Asn Ser
    210                 215                 220

Leu Gln Glu Lys Arg Glu Gln Leu His Ser Leu Leu Gly His Gln Thr
225                 230                 235                 240

Gly Thr Leu Ala Asn Leu Lys His Asn Leu His Ala Leu Ser Ser Asn
                245                 250                 255

Ser Ser Ser Leu Gln Gln Gln Gln Gln Leu Thr Glu Phe Val Gln
            260                 265                 270

Arg Leu Val Arg Ile Val Ala Gln Asp Gln His Pro Val Ser Leu Lys
        275                 280                 285

Thr Pro Lys Pro Val Phe Gln Asp Cys Ala Glu Ile Lys Arg Ser Gly
    290                 295                 300

Val Asn Thr Ser Gly Val Tyr Thr Ile Tyr Glu Thr Asn Met Thr Lys
305                 310                 315                 320

Pro Leu Lys Val Phe Cys Asp Met Glu Thr Asp Gly Gly Gly Trp Thr
                325                 330                 335

Leu Ile Gln His Arg Glu Asp Gly Ser Val Asn Phe Gln Arg Thr Trp
```

```
                    340             345             350
Glu Glu Tyr Lys Glu Gly Phe Gly Asn Val Ala Arg Glu His Trp Leu
            355                 360                 365
Gly Asn Glu Ala Val His Arg Leu Thr Ser Arg Thr Ala Tyr Leu Leu
        370                 375                 380
Arg Val Glu Leu His Asp Trp Glu Gly Arg Gln Thr Ser Ile Gln Tyr
385                 390                 395                 400
Glu Asn Phe Gln Leu Gly Ser Glu Arg Gln Arg Tyr Ser Leu Ser Val
                405                 410                 415
Asn Asp Ser Ser Ser Ala Gly Arg Lys Asn Ser Leu Ala Pro Gln
            420                 425                 430
Gly Thr Lys Phe Ser Thr Lys Asp Met Asp Asn Asp Asn Cys Met Cys
        435                 440                 445
Lys Cys Ala Gln Met Leu Ser Gly Gly Trp Trp Phe Asp Ala Cys Gly
    450                 455                 460
Leu Ser Asn Leu Asn Gly Ile Tyr Tyr Ser Val His Gln His Leu His
465                 470                 475                 480
Lys Ile Asn Gly Ile Arg Trp His Tyr Phe Arg Gly Pro Ser Tyr Ser
                485                 490                 495
Leu His Gly Thr Arg Met Met Leu Arg Pro Met Gly Ala
            500                 505

<210> SEQ ID NO 11
<211> LENGTH: 503
<212> TYPE: PRT
<213> ORGANISM: Homo sapien

<400> SEQUENCE: 11

Met Leu Leu Asp Gly Leu Leu Leu Leu Ala Thr Met Ala Ala Ala Gln
1               5                   10                  15
His Arg Gly Pro Glu Ala Gly Gly His Arg Gln Ile His Gln Val Arg
            20                  25                  30
Arg Gly Gln Cys Ser Tyr Thr Phe Val Val Pro Glu Pro Asp Ile Cys
        35                  40                  45
Gln Leu Ala Pro Thr Ala Ala Pro Glu Ala Leu Gly Gly Ser Asn Ser
    50                  55                  60
Leu Gln Arg Asp Leu Pro Ala Ser Arg Leu His Leu Thr Asp Trp Arg
65                  70                  75                  80
Ala Gln Arg Ala Gln Arg Ala Gln Arg Val Ser Gln Leu Glu Lys Ile
                85                  90                  95
Leu Glu Asn Asn Thr Gln Trp Leu Leu Lys Leu Glu Gln Ser Ile Lys
            100                 105                 110
Val Asn Leu Arg Ser His Leu Val Gln Ala Gln Gln Asp Thr Ile Gln
        115                 120                 125
Asn Gln Thr Thr Thr Met Leu Ala Leu Gly Ala Asn Leu Met Asn Gln
    130                 135                 140
Thr Lys Ala Gln Thr His Lys Leu Thr Ala Val Glu Ala Gln Val Leu
145                 150                 155                 160
Asn Gln Thr Leu His Met Lys Thr Gln Met Leu Glu Asn Ser Leu Ser
                165                 170                 175
Thr Asn Lys Leu Glu Arg Gln Met Leu Met Gln Ser Arg Glu Leu Gln
            180                 185                 190
Arg Leu Gln Gly Arg Asn Arg Ala Leu Glu Thr Arg Leu Gln Ala Leu
        195                 200                 205
```

-continued

Glu Ala Gln His Gln Ala Gln Leu Asn Ser Leu Gln Glu Lys Arg Glu
    210                 215                 220

Gln Leu His Ser Leu Leu Gly His Gln Thr Gly Thr Leu Ala Asn Leu
225                 230                 235                 240

Lys His Asn Leu His Ala Leu Ser Ser Asn Ser Ser Ser Leu Gln Gln
                245                 250                 255

Gln Gln Gln Gln Leu Thr Glu Phe Val Gln Arg Leu Val Arg Ile Val
            260                 265                 270

Ala Gln Asp Gln His Pro Val Ser Leu Lys Thr Pro Lys Pro Val Phe
        275                 280                 285

Gln Asp Cys Ala Glu Ile Lys Arg Ser Gly Val Asn Thr Ser Gly Val
    290                 295                 300

Tyr Thr Ile Tyr Glu Thr Asn Met Thr Lys Pro Leu Lys Val Phe Cys
305                 310                 315                 320

Asp Met Glu Thr Asp Gly Gly Gly Trp Thr Leu Ile Gln His Arg Glu
                325                 330                 335

Asp Gly Ser Val Asn Phe Gln Arg Thr Trp Glu Glu Tyr Lys Glu Gly
            340                 345                 350

Phe Gly Asn Val Ala Arg Glu His Trp Leu Gly Asn Glu Ala Val His
        355                 360                 365

Arg Leu Thr Ser Arg Thr Ala Tyr Leu Leu Arg Val Glu Leu His Asp
    370                 375                 380

Trp Glu Gly Arg Gln Thr Ser Ile Gln Tyr Glu Asn Phe Gln Leu Gly
385                 390                 395                 400

Ser Glu Arg Gln Arg Tyr Ser Leu Ser Val Asn Asp Ser Ser Ser Ser
                405                 410                 415

Ala Gly Arg Lys Asn Ser Leu Ala Pro Gln Gly Thr Lys Phe Ser Thr
            420                 425                 430

Lys Asp Met Asp Asn Asp Asn Cys Met Cys Lys Cys Ala Gln Met Leu
        435                 440                 445

Ser Gly Gly Trp Trp Phe Asp Ala Cys Gly Leu Ser Asn Leu Asn Gly
    450                 455                 460

Ile Tyr Tyr Ser Val His Gln His Leu His Lys Ile Asn Gly Ile Arg
465                 470                 475                 480

Trp His Tyr Phe Arg Gly Pro Ser Tyr Ser Ile His Gly Thr Arg Met
                485                 490                 495

Met Leu Arg Pro Met Gly Ala
            500

<210> SEQ ID NO 12
<211> LENGTH: 490
<212> TYPE: PRT
<213> ORGANISM: Homo sapien

<400> SEQUENCE: 12

Ala Phe Leu Ala Ala Ile Leu Thr His Ile Gly Cys Ser Asn Gln Arg
 1               5                  10                  15

Arg Ser Pro Glu Asn Ser Gly Arg Arg Tyr Asn Arg Ile Gln His Gly
            20                  25                  30

Gln Cys Ala Tyr Thr Phe Ile Leu Pro Glu His Asp Gly Asn Cys Arg
        35                  40                  45

Glu Ser Thr Thr Asp Gln Tyr Asn Thr Asn Ala Leu Gln Arg Asp Ala
    50                  55                  60

Pro His Val Glu Pro Asp Phe Ser Gln Lys Leu Gln His Leu Glu
65                  70                  75                  80

```
His Val Met Glu Asn Tyr Thr Gln Trp Leu Gln Lys Leu Glu Asn Tyr
                85                  90                  95
Ile Val Glu Asn Met Lys Ser Glu Met Ala Gln Ile Gln Gln Asn Ala
               100                 105                 110
Val Gln Asn His Thr Ala Thr Met Leu Glu Ile Gly Thr Ser Leu Leu
               115                 120                 125
Ser Gln Thr Ala Glu Gln Thr Arg Lys Leu Thr Asp Val Glu Thr Gln
130                 135                 140
Val Leu Asn Gln Thr Ser Arg Leu Glu Ile Gln Leu Leu Glu Asn Ser
145                 150                 155                 160
Leu Ser Thr Tyr Lys Leu Glu Lys Gln Leu Leu Gln Gln Thr Asn Glu
                165                 170                 175
Ile Leu Lys Ile His Glu Lys Asn Ser Leu Leu Glu His Lys Ile Leu
                180                 185                 190
Glu Met Glu Gly Lys His Lys Glu Glu Leu Asp Thr Leu Lys Glu Glu
                195                 200                 205
Lys Glu Asn Leu Gln Gly Leu Val Thr Arg Gln Thr Tyr Ile Ile Gln
                210                 215                 220
Glu Leu Glu Lys Gln Leu Asn Arg Ala Thr Thr Asn Asn Ser Val Leu
225                 230                 235                 240
Gln Lys Gln Gln Leu Glu Leu Met Asp Thr Val His Asn Leu Val Asn
                245                 250                 255
Leu Cys Thr Lys Glu Val Leu Leu Lys Gly Gly Lys Arg Glu Glu Glu
                260                 265                 270
Lys Pro Phe Arg Asp Cys Ala Asp Val Tyr Gln Ala Gly Phe Asn Lys
                275                 280                 285
Ser Gly Ile Tyr Thr Ile Tyr Ile Asn Asn Met Pro Glu Pro Lys Lys
                290                 295                 300
Val Phe Cys Asn Met Asp Val Asn Gly Gly Gly Trp Thr Val Ile Gln
305                 310                 315                 320
His Arg Glu Asp Gly Ser Leu Asp Phe Gln Arg Gly Trp Lys Glu Tyr
                325                 330                 335
Lys Met Gly Phe Gly Asn Pro Ser Gly Glu Tyr Trp Leu Gly Asn Glu
                340                 345                 350
Phe Ile Phe Ala Ile Thr Ser Gln Arg Gln Tyr Met Leu Arg Ile Glu
                355                 360                 365
Leu Met Asp Trp Glu Gly Asn Arg Ala Tyr Ser Gln Tyr Asp Arg Phe
                370                 375                 380
His Ile Gly Asn Glu Lys Gln Asn Tyr Arg Leu Tyr Leu Lys Gly His
385                 390                 395                 400
Thr Gly Thr Ala Gly Lys Gln Ser Ser Leu Ile Leu His Gly Ala Asp
                405                 410                 415
Phe Ser Thr Lys Asp Ala Asp Asn Asp Asn Cys Met Cys Lys Cys Ala
                420                 425                 430
Leu Met Leu Thr Gly Gly Trp Trp Phe Asp Ala Cys Gly Pro Ser Asn
                435                 440                 445
Leu Asn Gly Met Phe Tyr Thr Ala Gly Gln Asn His Gly Lys Leu Asn
                450                 455                 460
Gly Ile Lys Trp His Tyr Phe Lys Gly Pro Ser Tyr Ser Ile Arg Ser
465                 470                 475                 480
Thr Thr Met Met Ile Arg Pro Leu Asp Phe
                485                 490
```

<210> SEQ ID NO 13
<211> LENGTH: 491
<212> TYPE: PRT
<213> ORGANISM: Homo sapien

<400> SEQUENCE: 13

```
Ala Phe Leu Ala Ala Ile Leu Ala His Ile Gly Cys Thr Thr Gln Arg
 1               5                  10                  15

Arg Ser Pro Glu Asn Ser Gly Arg Arg Phe Asn Arg Ile Gln His Gly
                20                  25                  30

Gln Cys Thr Tyr Thr Phe Ile Leu Pro Glu Gln Asp Gly Asn Cys Arg
            35                  40                  45

Glu Ser Thr Thr Asp Gln Tyr Asn Thr Asn Ala Leu Gln Arg Asp Ala
        50                  55                  60

Pro His Val Glu Gln Asp Phe Ser Phe Gln Lys Leu Gln His Leu Glu
65                  70                  75                  80

His Val Met Glu Asn Tyr Thr Gln Trp Leu Gln Lys Leu Glu Ser Tyr
                85                  90                  95

Ile Val Glu Asn Met Lys Ser Glu Met Ala Gln Leu Gln Gln Asn Ala
            100                 105                 110

Val Gln Asn His Thr Ala Thr Met Leu Glu Ile Gly Thr Ser Leu Leu
        115                 120                 125

Ser Gln Thr Ala Glu Gln Thr Arg Lys Leu Thr Asp Val Glu Thr Gln
    130                 135                 140

Val Leu Asn Gln Thr Ser Arg Leu Glu Ile Gln Leu Leu Glu Asn Ser
145                 150                 155                 160

Leu Ser Thr Tyr Lys Leu Glu Lys Gln Leu Leu Gln Gln Thr Asn Glu
                165                 170                 175

Ile Leu Lys Ile His Glu Lys Asn Ser Leu Leu Glu His Lys Ile Leu
            180                 185                 190

Glu Met Glu Glu Arg His Lys Glu Met Asp Thr Leu Lys Glu Glu
        195                 200                 205

Lys Glu Asn Leu Gln Gly Leu Val Thr Arg Gln Ser Tyr Ile Ile Gln
    210                 215                 220

Glu Leu Glu Lys Gln Leu Asn Lys Ala Thr Thr Asn Asn Ser Val Leu
225                 230                 235                 240

Gln Lys Gln Gln Leu Glu Leu Met Asp Thr Val His Thr Leu Ile Thr
                245                 250                 255

Leu Cys Ser Lys Glu Gly Val Leu Leu Lys Asn Ala Lys Arg Glu Glu
            260                 265                 270

Glu Lys Pro Phe Arg Asp Cys Ala Asp Val Tyr Gln Ala Gly Phe Asn
        275                 280                 285

Lys Ser Gly Ile Tyr Thr Ile Tyr Ile Asn Asn Val Ser Asp Pro Lys
    290                 295                 300

Lys Val Phe Cys Asn Met Asp Val Asn Gly Gly Gly Trp Thr Val Ile
305                 310                 315                 320

Gln His Arg Glu Asp Gly Ser Leu Asp Phe Gln Lys Gly Trp Lys Glu
                325                 330                 335

Tyr Lys Met Gly Phe Gly Ser Pro Ser Gly Glu Tyr Trp Leu Gly Asn
            340                 345                 350

Glu Phe Ile Phe Ala Ile Thr Ser Gln Arg Gln Tyr Ser Leu Arg Ile
        355                 360                 365

Glu Leu Met Asp Trp Glu Gly Asn Arg Ala Tyr Ser Gln Tyr Asp Arg
    370                 375                 380
```

-continued

```
Phe His Ile Gly Asn Glu Lys Gln Asn Tyr Arg Leu Tyr Leu Lys Gly
385                 390                 395                 400

His Ser Gly Thr Ala Gly Lys Gln Ser Leu Ile Leu His Gly Ala
                405                 410                 415

Glu Phe Ser Thr Lys Asp Ala Asp Asn Asp Asn Cys Met Cys Lys Cys
                420                 425                 430

Ala Leu Met Leu Thr Gly Gly Trp Trp Phe Asp Ala Cys Gly Pro Ser
                435                 440                 445

Asn Leu Asn Gly Met Phe Tyr Thr Ala Gly Gln Asn His Gly Lys Leu
                450                 455                 460

Asn Gly Ile Lys Trp His Tyr Phe Lys Gly Pro Arg Tyr Ser Ile Arg
465                 470                 475                 480

Ser Thr Thr Met Met Ile Arg Pro Leu Asp Phe
                485                 490

<210> SEQ ID NO 14
<211> LENGTH: 497
<212> TYPE: PRT
<213> ORGANISM: Homo sapien

<400> SEQUENCE: 14

Met Thr Val Phe Leu Ser Phe Ala Phe Ala Ala Ile Leu Thr His
1               5                   10                  15

Ile Gly Cys Ser Asn Gln Arg Arg Asn Pro Glu Asn Ser Gly Arg Arg
                20                  25                  30

Tyr Asn Arg Ile Gln His Gly Gln Cys Ala Tyr Thr Phe Ile Leu Pro
                35                  40                  45

Glu His Asp Gly Asn Cys Arg Glu Ser Thr Thr Asp Gln Tyr Asn Thr
                50                  55                  60

Asn Ala Leu Gln Arg Asp Ala Pro His Val Glu Pro Asp Phe Ser Ser
65                  70                  75                  80

Gln Lys Leu Gln His Leu Glu His Val Met Glu Asn Tyr Thr Gln Trp
                85                  90                  95

Leu Gln Lys Leu Glu Asn Tyr Ile Val Glu Asn Met Lys Ser Glu Met
                100                 105                 110

Ala Gln Ile Gln Gln Asn Ala Val Gln Asn His Thr Ala Thr Met Leu
                115                 120                 125

Glu Ile Gly Thr Ser Leu Leu Ser Gln Thr Ala Glu Gln Thr Arg Lys
                130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175

Leu Leu Gln Thr Asn Glu Ile Leu Lys Ile His Glu Lys Asn Ser Leu
                180                 185                 190

Leu Glu His Lys Ile Leu Glu Met Glu Gly Lys His Lys Glu Glu Met
                195                 200                 205

Asp Thr Leu Lys Glu Glu Lys Glu Asn Leu Gln Gly Leu Val Ser Arg
                210                 215                 220

Gln Ser Phe Ile Ile Gln Glu Leu Glu Lys Gln Leu Ser Arg Ala Thr
225                 230                 235                 240

Asn Asn Asn Ser Ile Leu Gln Lys Gln Gln Leu Glu Leu Met Asp Thr
                245                 250                 255

Val His Asn Leu Ile Ser Leu Cys Thr Lys Glu Gly Val Leu Leu Lys
```

-continued

```
            260                 265                 270
Gly Gly Lys Arg Glu Glu Lys Pro Phe Arg Asp Cys Ala Asp Val
        275                 280                 285
Tyr Gln Ala Gly Phe Asn Lys Ser Gly Ile Tyr Thr Ile Tyr Phe Asn
    290                 295                 300
Asn Val Pro Glu Pro Lys Lys Val Phe Cys Asn Met Asp Val Asn Gly
305                 310                 315                 320
Gly Gly Trp Thr Val Ile Gln His Arg Glu Asp Gly Ser Leu Asp Phe
                325                 330                 335
Gln Lys Gly Trp Lys Glu Tyr Lys Met Gly Phe Gly Ser Pro Ser Gly
        340                 345                 350
Glu Tyr Trp Leu Gly Asn Glu Phe Ile Phe Ala Ile Thr Ser Gln Arg
            355                 360                 365
Gln Tyr Met Leu Arg Ile Glu Leu Met Asp Trp Glu Gly Asn Arg Ala
    370                 375                 380
Tyr Ser Gln Tyr Asp Arg Phe His Ile Gly Asn Glu Lys Gln Asn Tyr
385                 390                 395                 400
Arg Leu Tyr Leu Lys Gly His Thr Gly Thr Ala Gly Lys Gln Ser Ser
                405                 410                 415
Leu Ile Leu His Gly Ala Asp Phe Ser Thr Lys Asp Ala Asp Asn Asp
        420                 425                 430
Asn Cys Met Cys Lys Cys Ala Leu Met Leu Thr Gly Gly Trp Trp Phe
            435                 440                 445
Asp Ala Cys Gly Pro Ser Asn Leu Asn Gly Met Phe Tyr Thr Ala Gly
    450                 455                 460
Gln Asn His Gly Lys Leu Asn Gly Ile Lys Trp His Tyr Phe Lys Gly
465                 470                 475                 480
Pro Arg Tyr Ser Ile Arg Ser Thr Thr Met Met Ile Arg Pro Leu Asp
                485                 490                 495
Phe

<210> SEQ ID NO 15
<211> LENGTH: 496
<212> TYPE: PRT
<213> ORGANISM: Homo sapien

<400> SEQUENCE: 15

Met Trp Gln Ile Ile Phe Leu Thr Phe Gly Trp Asp Ala Val Leu Thr
1               5                   10                  15
Ser Ala Tyr Ser Asn Phe Arg Lys Ser Val Asp Ser Thr Gly Arg Arg
                20                  25                  30
Arg Tyr Arg Ile Gln Asn Gly Pro Cys Ala Tyr Thr Phe Leu Leu Pro
            35                  40                  45
Glu Thr Asp Ser Gly Arg Ser Ser Ser Thr Tyr Met Thr Asn Ala
    50                  55                  60
Val Gln Arg Asp Ala Pro Pro Asp Tyr Glu Asp Ser Val Gln Ser Leu
65                  70                  75                  80
Gln Leu Leu Glu Asn Val Met Glu Asn Tyr Thr Gln Trp Leu Met Lys
                85                  90                  95
Leu Glu Asn Tyr Ile Gln Asp Asn Met Lys Lys Glu Met Ala Glu Ile
                100                 105                 110
Gln Gln Asn Val Val Gln Asn His Thr Ala Val Met Ile Glu Ile Gly
            115                 120                 125
Thr Ser Leu Leu Ser Gln Thr Ala Glu Gln Thr Arg Lys Leu Thr Asp
```

```
                130                 135                 140
Val Glu Thr Gln Val Leu Asn Gln Thr Thr Arg Leu Glu Leu Gln Leu
145                 150                 155                 160

Leu Gln His Ser Ile Ser Thr Tyr Lys Leu Glu Lys Gln Ile Leu Asp
            165                 170                 175

Gln Thr Ser Glu Ile Asn Lys Ile His Asn Lys Asn Ser Phe Leu Glu
            180                 185                 190

Gln Lys Val Leu Asp Met Glu Gly Lys His Ser Glu Glu Met Gln Thr
            195                 200                 205

Met Lys Glu Gln Lys Asp Glu Leu Gln Val Leu Val Ser Lys Gln Ser
210                 215                 220

Ser Val Ile Asp Glu Leu Glu Lys Lys Leu Val Thr Ala Thr Val Asn
225                 230                 235                 240

Asn Ser Leu Leu Gln Lys Gln Gln His Asp Leu Met Asp Thr Val Asn
            245                 250                 255

Ser Leu Leu Thr Met Met Ser Ser Pro Asn Ser Lys Ser Ser Leu Ala
            260                 265                 270

Ile Arg Arg Glu Glu Gln Thr Thr Phe Arg Asp Cys Ala Asp Val Phe
            275                 280                 285

Lys Ala Gly Leu Thr Lys Ser Gly Ile Tyr Thr Leu Thr Phe Pro Asn
            290                 295                 300

Ser Pro Glu Glu Ile Lys Ala Tyr Cys Asn Met Asp Val Gly Gly Gly
305                 310                 315                 320

Gly Trp Thr Val Ile Gln His Arg Glu Asp Gly Ser Leu Asp Phe Gln
            325                 330                 335

Lys Gly Trp Lys Glu Tyr Lys Met Gly Phe Gly Asn Pro Leu Gly Glu
            340                 345                 350

Tyr Trp Leu Gly Asn Glu Phe Ile Ser Gln Ile Thr Gly Gln His Arg
            355                 360                 365

Tyr Val Leu Lys Ile Gln Leu Lys Asp Trp Glu Gly Asn Glu Ala His
            370                 375                 380

Ser Leu Tyr Asp His Phe Tyr Ile Ala Gly Glu Glu Ser Asn Tyr Arg
385                 390                 395                 400

Ile His Leu Thr Gly Leu Thr Gly Thr Ala Ala Lys Ile Ser Ser Ile
            405                 410                 415

Ser Gln Pro Gly Ser Asp Phe Ser Thr Lys Asp Ser Asp Asn Asp Lys
            420                 425                 430

Cys Ile Cys Lys Cys Ser Leu Met Leu Thr Gly Gly Trp Trp Phe Asp
            435                 440                 445

Ala Cys Gly Pro Ser Asn Leu Asn Gly Gln Phe Tyr Pro Gln Lys Gln
            450                 455                 460

Asn Thr Asn Lys Phe Asn Gly Ile Lys Trp Tyr Tyr Trp Lys Gly Ser
465                 470                 475                 480

Gly Tyr Ser Ile Lys Ala Thr Thr Met Met Ile Arg Pro Ala Asp Phe
            485                 490                 495

<210> SEQ ID NO 16
<211> LENGTH: 496
<212> TYPE: PRT
<213> ORGANISM: Homo sapien

<400> SEQUENCE: 16

Met Trp Gln Ile Val Phe Phe Thr Leu Ser Cys Asp Ala Val Leu Thr
1               5                   10                  15
```

-continued

```
Ala Ala Tyr Asn Asn Phe Arg Lys Ser Met Asp Ser Ile Gly Lys Lys
        20                  25                  30

Arg Tyr Arg Ile Gln His Gly Ser Cys Ala Tyr Thr Phe Leu Leu Pro
        35                  40                  45

Glu Met Asp Asn Gly Arg Ser Ser Ser Thr Tyr Val Thr Asn Ala
50                      55                      60

Val Gln Arg Asp Ala Pro Pro Glu Tyr Glu Asp Ser Val Gln Ser Leu
65                      70                  75                  80

Gln Leu Leu Glu Asn Val Met Glu Asn Tyr Thr Gln Trp Leu Met Lys
            85                  90                  95

Leu Glu Asn Tyr Ile Gln Asp Asn Met Lys Lys Glu Met Ala Glu Ile
            100                 105                 110

Gln Gln Asn Ala Val Gln Asn His Thr Ala Val Met Ile Glu Ile Gly
            115                 120                 125

Thr Ser Leu Leu Ser Gln Thr Ala Glu Gln Thr Arg Lys Leu Thr Asp
130                 135                 140

Val Glu Thr Gln Val Leu Asn Gln Thr Thr Arg Leu Glu Leu Gln Leu
145                 150                 155                 160

Leu Gln His Ser Ile Ser Thr Tyr Lys Leu Glu Lys Gln Ile Leu Asp
                165                 170                 175

Gln Thr Ser Glu Ile Asn Lys Ile His Asp Lys Asn Ser Phe Leu Glu
            180                 185                 190

Lys Lys Val Leu Asp Met Glu Asp Lys His Ile Ile Glu Met Gln Thr
            195                 200                 205

Ile Lys Glu Glu Lys Asp Glu Leu Gln Val Leu Val Ser Lys Gln Asn
210                 215                 220

Ser Ile Glu Glu Leu Glu Lys Lys Ile Val Thr Ala Thr Val Asn
225                 230                 235                 240

Asn Ser Val Leu Gln Lys Gln Gln His Asp Leu Met Asp Thr Val Asn
            245                 250                 255

Asn Leu Leu Thr Met Met Ser Thr Ser Asn Ser Ala Lys Asp Ser Thr
            260                 265                 270

Val Ala Arg Glu Glu Gln Ile Ser Phe Arg Asp Cys Ala Asp Val Phe
            275                 280                 285

Lys Ala Gly His Thr Lys Asn Gly Ile Tyr Thr Leu Thr Phe Pro Asn
290                 295                 300

Ser Pro Glu Glu Ile Lys Ala Tyr Cys Asn Met Asp Ala Gly Gly Gly
305                 310                 315                 320

Gly Trp Thr Ile Ile Gln Arg Arg Glu Asp Gly Ser Leu Asp Phe Gln
            325                 330                 335

Lys Gly Trp Lys Glu Tyr Lys Val Gly Phe Gly Ser Pro Ser Gly Glu
            340                 345                 350

Tyr Trp Leu Gly Asn Glu Phe Ile Ser Gln Ile Thr Asn Gln Gln Arg
            355                 360                 365

Tyr Val Leu Lys Ile His Leu Lys Asp Trp Glu Gly Asn Glu Ala Tyr
        370                 375                 380

Ser Leu Tyr Asp His Phe Tyr Ile Ser Gly Glu Leu Asn Tyr Arg
385                 390                 395                 400

Ile His Leu Lys Gly Leu Thr Gly Thr Ala Lys Ile Ser Ser Ile
                405                 410                 415

Ser Gln Pro Gly Asn Asp Phe Ser Thr Lys Asp Gly Asp Asn Asp Lys
            420                 425                 430

Cys Ile Cys Lys Cys Ser Leu Met Leu Thr Gly Gly Trp Trp Phe Asp
```

```
          435                 440                 445
Ala Cys Gly Pro Ser Asn Leu Asn Gly Met Phe Tyr Pro Gln Arg Gln
    450                 455                 460

Asn Thr Asn Lys Phe Asn Gly Ile Lys Trp Tyr Tyr Trp Lys Gly Ser
465                 470                 475                 480

Gly Tyr Ser Ile Lys Ala Thr Thr Met Met Ile Arg Pro Ala Asp Phe
                485                 490                 495
```

<210> SEQ ID NO 17
<211> LENGTH: 1512
<212> TYPE: DNA
<213> ORGANISM: Homo sapien

<400> SEQUENCE: 17

```
atgctctccc agctagccat gctgcagggc agcctcctcc ttgtggttgc caccatgtct      60
gtggctcaac agacaaggca ggaggcggat aggggctgcg agacacttgt agtccagcac     120
ggccactgta gctacacctt cttgctgccc aagtctgagc cctgccctcc ggggcctgag     180
gtctccaggg actccaacac cctccagaga gaatcactgg ccaacccact gcacctgggg     240
aagttgccca cccagcaggt gaaacagctg gagcaggcac tgcagaacaa cacgcagtgg     300
ctgaagaagc tagagagggc catcaagacg atcttgaggt cgaagctgga gcaggtccag     360
cagcaaatgg cccagaatca gacggcccc atgctagagc tgggcaccag cctcctgaac      420
cagaccactg cccagatccg caagctgacc gacatggagg ctcagctcct gaaccagaca     480
tcaagaatgg atgcccagat gccagagacc tttctgtcca ccaacaagct ggagaaccag     540
ctgctgctac agaggcagaa gctccagcag cttcagggcc aaaacagcgc gctcgagaag     600
cggttgcagg ccctggagac caagcagcag gaggagctgg ccagcatcct cagcaagaag     660
gcgaagctgc tgaacacgct gagccgccag agcgccgccc tcaccaacat cgagcgcggc     720
ctgcgcggtg tcaggcacaa ctccagcctc tgcaggacc agcagcacag cctgcgccag      780
ctgctggtgt tgttgcggca cctggtgcaa gaaagggcta acgcctcggc cccggccttc     840
ataatgcag gtgagcaggt gttccaggac tgtgcagaga tccagcgctc tggggccagt      900
gccagtggtg tctacaccat ccaggtgtcc aatgcaacga agcccaggaa ggtgttctgt     960
gacctgcaga gcagtggagg caggtggacc ctcatccagc gccgtgagaa tggcaccgtg    1020
aattttcagc ggaactggaa ggattacaaa cagggcttcg agacccagc tggggagcac     1080
tggctgggca atgaagtggt gcaccagctc accagaaggg cagcctactc tctgcgtgtg    1140
gagctgcaag actgggaagg ccacgaggcc tatgcccagt acgaacattt ccacctgggc    1200
agtgagaacc agctatacag gctttctgtg gtcgggtaca gcggctcagc agggcgccag    1260
agcagcctgg tcctgcagaa caccagcttt agcacccttg actcagacaa cgaccactgt    1320
ctctgcaagt gtgcccaggt gatgtctgga gggtggtggt tgacgcctg tggcctgtca     1380
aacctcaacg gcgtctacta ccacgctccc gacaacaagt acaagatgga cggcatccgc    1440
tggcactact tcaagggccc cagctactca ctgcgtgcct tcgcatgat gatacggcct     1500
ttggacatct aa                                                        1512
```

<210> SEQ ID NO 18
<211> LENGTH: 503
<212> TYPE: PRT
<213> ORGANISM: Homo sapien

<400> SEQUENCE: 18

-continued

```
Met Leu Ser Gln Leu Ala Met Leu Gln Gly Ser Leu Leu Val Val
 1               5                  10                  15

Ala Thr Met Ser Val Ala Gln Gln Thr Arg Gln Glu Ala Asp Arg Gly
             20                  25                  30

Cys Glu Thr Leu Val Val Gln His Gly His Cys Ser Tyr Thr Phe Leu
             35                  40                  45

Leu Pro Lys Ser Glu Pro Cys Pro Pro Gly Pro Glu Val Ser Arg Asp
         50                  55                  60

Ser Asn Thr Leu Gln Arg Glu Ser Leu Ala Asn Pro Leu His Leu Gly
 65                  70                  75                  80

Lys Leu Pro Thr Gln Gln Val Lys Gln Leu Glu Gln Ala Leu Gln Asn
                 85                  90                  95

Asn Thr Gln Trp Leu Lys Lys Leu Glu Arg Ala Ile Lys Thr Ile Leu
                100                 105                 110

Arg Ser Lys Leu Glu Gln Val Gln Gln Met Ala Gln Asn Gln Thr
             115                 120                 125

Ala Pro Met Leu Glu Leu Gly Thr Ser Leu Leu Asn Gln Thr Thr Ala
         130                 135                 140

Gln Ile Arg Lys Leu Thr Asp Met Glu Ala Gln Leu Leu Asn Gln Thr
145                 150                 155                 160

Ser Arg Met Asp Ala Gln Met Pro Glu Thr Phe Leu Ser Thr Asn Lys
                165                 170                 175

Leu Glu Asn Gln Leu Leu Leu Gln Arg Gln Lys Leu Gln Gln Leu Gln
             180                 185                 190

Gly Gln Asn Ser Ala Leu Glu Lys Arg Leu Gln Ala Leu Glu Thr Lys
         195                 200                 205

Gln Gln Glu Glu Leu Ala Ser Ile Leu Ser Lys Lys Ala Lys Leu Leu
210                 215                 220

Asn Thr Leu Ser Arg Gln Ser Ala Ala Leu Thr Asn Ile Glu Arg Gly
225                 230                 235                 240

Leu Arg Gly Val Arg His Asn Ser Ser Leu Leu Gln Asp Gln Gln His
                245                 250                 255

Ser Leu Arg Gln Leu Leu Val Leu Leu Arg His Leu Val Gln Glu Arg
             260                 265                 270

Ala Asn Ala Ser Ala Pro Ala Phe Ile Met Ala Gly Glu Gln Val Phe
         275                 280                 285

Gln Asp Cys Ala Glu Ile Gln Arg Ser Gly Ala Ser Ala Ser Gly Val
290                 295                 300

Tyr Thr Ile Gln Val Ser Asn Ala Thr Lys Pro Arg Lys Val Phe Cys
305                 310                 315                 320

Asp Leu Gln Ser Ser Gly Gly Arg Trp Thr Leu Ile Gln Arg Arg Glu
                325                 330                 335

Asn Gly Thr Val Asn Phe Gln Arg Asn Trp Lys Asp Tyr Lys Gln Gly
             340                 345                 350

Phe Gly Asp Pro Ala Gly Glu His Trp Leu Gly Asn Glu Val Val His
         355                 360                 365

Gln Leu Thr Arg Arg Ala Ala Tyr Ser Leu Arg Val Glu Leu Gln Asp
         370                 375                 380

Trp Glu Gly His Glu Ala Tyr Ala Gln Tyr Glu His Phe His Leu Gly
385                 390                 395                 400

Ser Glu Asn Gln Leu Tyr Arg Leu Ser Val Val Gly Tyr Ser Gly Ser
                405                 410                 415

Ala Gly Arg Gln Ser Ser Leu Val Leu Gln Asn Thr Ser Phe Ser Thr
```

```
              420                 425                 430
Leu Asp Ser Asp Asn Asp His Cys Leu Cys Lys Cys Ala Gln Val Met
            435                 440                 445

Ser Gly Gly Trp Trp Phe Asp Ala Cys Gly Leu Ser Asn Leu Asn Gly
        450                 455                 460

Val Tyr Tyr His Ala Pro Asp Asn Lys Tyr Lys Met Asp Gly Ile Arg
465                 470                 475                 480

Trp His Tyr Phe Lys Gly Pro Ser Tyr Ser Leu Arg Ala Ser Arg Met
                485                 490                 495

Met Ile Arg Pro Leu Asp Ile
            500

<210> SEQ ID NO 19
<211> LENGTH: 1497
<212> TYPE: DNA
<213> ORGANISM: Homo sapien

<400> SEQUENCE: 19
atgacagttt tcctttcctt tgctttcctc gctgccattc tgactcacat agggtgcagc      60
aatcagcgcc gaagtccaga aaacagtggg agaagatata accggattca acatgggcaa     120
tgtgcctaca cttcattct tccagaacac gatggcaact gtcgtgagag tacgacagac      180
cagtacaaca caaacgctct gcagagagat gctccacacg tggaaccgga tttctcttcc     240
cagaaacttc aacatctgga acatgtgatg gaaaattata ctcagtggct gcaaaaactt     300
gagaattaca ttgtggaaaa catgaagtcg gagatggccc agatacagca gaatgcagtt     360
cagaaccaca cggctaccat gctggagata ggaaccagcc tcctctctca gactgcagag     420
cagaccagaa agctgacaga tgttgagacc caggtactaa atcaaacttc tcgacttgag     480
atacagctgc tggagaattc attatccacc tacaagctag agaagcaact tcttcaacag     540
acaaatgaaa tcttgaagat ccatgaaaaa acagtttat tagaacataa aatcttagaa       600
atggaaggaa acacaagga gagttggac accttaaagg aagagaaaga gaaccttcaa        660
ggcttggtta ctcgtcaaac atatataatc caggagctgg aaaagcaatt aaacagagct     720
accaccaaca acagtgtcct tcagaagcag caactggagc tgatggacac agtccacaac     780
cttgtcaatc tttgcactaa agaaggtgtt ttactaaagg gaggaaaaag agaggaagag     840
aaaccattta gagactgtgc tgaagtattc aaatcaggac acaccacaaa tggcatctac     900
acgttaacat tccctaattc tacagaagag atcaaggcct actgtgacat ggaagctgga     960
ggaggcgggt ggacaattat tcagcgacgt gaggatggca gcgttgattt tcagaggact    1020
tggaaagaat ataaagtggg atttggtaac ccttcaggag aatattggct gggaaatgag    1080
tttgtttcgc aactgactaa tcagcaacgc tatgtgctta aaatacacct taagactgg     1140 gaagggaatg aggcttactc attgtatgaa catttctatc tctcaagtga agaactcaat    1200
tataggattc accttaaagg acttacaggg acagccggca aaataagcag catcagccaa    1260
ccaggaaatg atttagcac aaaggatgga gacaacgaca atgtatttg caaatgttca       1320 caaatgctaa caggaggctg gtggtttgat gcatgtggtc cttccaactt gaacggaatg    1380
tactatccac agaggcagaa cacaaataag ttcaacggca ttaaatggta ctactggaaa    1440
ggctcaggct attcgctcaa ggccacaacc atgatgatcc gaccagcaga tttctaa       1497

<210> SEQ ID NO 20
<211> LENGTH: 498
<212> TYPE: PRT
```

<213> ORGANISM: Homo sapien

<400> SEQUENCE: 20

```
Met Thr Val Phe Leu Ser Phe Ala Phe Leu Ala Ala Ile Leu Thr His
 1               5                  10                  15

Ile Gly Cys Ser Asn Gln Arg Arg Ser Pro Glu Asn Ser Gly Arg Arg
            20                  25                  30

Tyr Asn Arg Ile Gln His Gly Gln Cys Ala Tyr Thr Phe Ile Leu Pro
        35                  40                  45

Glu His Asp Gly Asn Cys Arg Glu Ser Thr Thr Asp Gln Tyr Asn Thr
 50                  55                  60

Asn Ala Leu Gln Arg Asp Ala Pro His Val Glu Pro Asp Phe Ser Ser
 65                  70                  75                  80

Gln Lys Leu Gln His Leu Glu His Val Met Glu Asn Tyr Thr Gln Trp
                85                  90                  95

Leu Gln Lys Leu Glu Asn Tyr Ile Val Glu Asn Met Lys Ser Glu Met
            100                 105                 110

Ala Gln Ile Gln Gln Asn Ala Val Gln Asn His Thr Ala Thr Met Leu
        115                 120                 125

Glu Ile Gly Thr Ser Leu Leu Ser Gln Thr Ala Glu Gln Thr Arg Lys
130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175

Leu Leu Gln Gln Thr Asn Glu Ile Leu Lys Ile His Glu Lys Asn Ser
            180                 185                 190

Leu Leu Glu His Lys Ile Leu Glu Met Glu Gly Lys His Lys Glu Glu
        195                 200                 205

Leu Asp Thr Leu Lys Glu Glu Lys Glu Asn Leu Gln Gly Leu Val Thr
210                 215                 220

Arg Gln Thr Tyr Ile Ile Gln Glu Leu Glu Lys Gln Leu Asn Arg Ala
225                 230                 235                 240

Thr Thr Asn Asn Ser Val Leu Gln Lys Gln Gln Leu Glu Leu Met Asp
                245                 250                 255

Thr Val His Asn Leu Val Asn Leu Cys Thr Lys Glu Gly Val Leu Leu
            260                 265                 270

Lys Gly Gly Lys Arg Glu Glu Lys Pro Phe Arg Asp Cys Ala Glu
        275                 280                 285

Val Phe Lys Ser Gly His Thr Thr Asn Gly Ile Tyr Thr Leu Thr Phe
290                 295                 300

Pro Asn Ser Thr Glu Glu Ile Lys Ala Tyr Cys Asp Met Glu Ala Gly
305                 310                 315                 320

Gly Gly Gly Trp Thr Ile Ile Gln Arg Arg Glu Asp Gly Ser Val Asp
                325                 330                 335

Phe Gln Arg Thr Trp Lys Glu Tyr Lys Val Gly Phe Gly Asn Pro Ser
            340                 345                 350

Gly Glu Tyr Trp Leu Gly Asn Glu Phe Val Ser Gln Leu Thr Asn Gln
        355                 360                 365

Gln Arg Tyr Val Leu Lys Ile His Leu Lys Asp Trp Glu Gly Asn Glu
370                 375                 380

Ala Tyr Ser Leu Tyr Glu His Phe Tyr Leu Ser Ser Glu Glu Leu Asn
385                 390                 395                 400
```

```
Tyr Arg Ile His Leu Lys Gly Leu Thr Gly Thr Ala Gly Lys Ile Ser
            405                 410                 415

Ser Ile Ser Gln Pro Gly Asn Asp Phe Ser Thr Lys Asp Gly Asp Asn
            420                 425                 430

Asp Lys Cys Ile Cys Lys Cys Ser Gln Met Leu Thr Gly Gly Trp Trp
            435                 440                 445

Phe Asp Ala Cys Gly Pro Ser Asn Leu Asn Gly Met Tyr Tyr Pro Gln
450                 455                 460

Arg Gln Asn Thr Asn Lys Phe Asn Gly Ile Lys Trp Tyr Tyr Trp Lys
465                 470                 475                 480

Gly Ser Gly Tyr Ser Leu Lys Ala Thr Thr Met Met Ile Arg Pro Ala
            485                 490                 495

Asp Phe

<210> SEQ ID NO 21
<211> LENGTH: 1491
<212> TYPE: DNA
<213> ORGANISM: Homo sapien

<400> SEQUENCE: 21
atgtggcaga ttgttttctt tactctgagc tgtgatcttg tcttggccgc agcctataac      60
aactttcgga agagcatgga cagcatagga agaagcaat atcaggtcca gcatgggtcc     120
tgcagctaca ctttcctcct gccagagatg acaactgcc gctcttcctc cagcccctac     180
gtgtccaatg ctgtgcagag ggacgcgccg ctcgaatacg atgactcggt gcagaggctg     240
caagtgctgg agaacatcat ggaaaacaac actcagtggc taatgaagct tgagaattat     300
atccaggaca catgaagaa agaaatggta gagatacagc agaatgcagt acagaaccag     360
acggctgtga tgatagaaat agggacaaac ctgttgaacc aaacagctga gcaaacgcgg     420
aagttaactg atgtggaagc ccaagtatta aatcagacca cgagacttga acttcagctc     480
ttggaacact ccctctcgac aaacaaattg gaaaaacaga ttttggacca gaccagtgaa     540
ataaacaaat gcaagataa gaacagtttc ctagaaaaga aggtgctagc tatggaagac     600
aagcacatca tccaactaca gtcaataaaa gaagagaaag atcagctaca ggtgttagta     660
tccaagcaaa attccatcat gaagaacta gaaaaaaaa tagtgactgc cacggtgaat     720
aattcagttc ttcaaaagca gcaacatgat ctcatggaga cagttaataa cttactgact     780
atgatgtcca catcaaactc agctaaggac cccactgttg ctaaagaaga caaaatcagc     840
ttcagagact gtgcagatgt atatcaagct ggttttaata aaagtggaat ctacactatt     900
tatattaata atatgccaga acccaaaaag gtgttttgca atatggatgt caatgggga      960 ggttggactg taatacaaca tcgtgaagat ggaagtctag atttccaaag aggctggaag    1020
gaatataaaa tgggttttgg aaatccctcc ggtgaatatt ggctgggaa tgagtttatt    1080 tttgccatta ccagtcagag gcagtacatg ctaagaattg agttaatgga ctgggaaggg    1140
aaccgagcct attcacagta tgacagattc acataggaa atgaaaagca aaactatagg    1200
ttgtatttaa aaggtcacac tgggacagca ggaaaacaga gcagcctgat cttacacggt    1260
gctgatttca gcactaaaga tgctgataat gacaactgta tgtgcaaatg tgccctcatg    1320
ttaacaggag gatggtggtt tgatgcttgt ggcccctcca atctaaatgg aatgttctat    1380
actgcgggac aaaaccatgg aaaactgaat gggataaagt ggcactactt caagggccc    1440 agttactcct acgttccac aactatgatg attcgacctt tagatttttg a             1491
```

<210> SEQ ID NO 22
<211> LENGTH: 496
<212> TYPE: PRT
<213> ORGANISM: Homo sapien

<400> SEQUENCE: 22

```
Met Trp Gln Ile Val Phe Phe Thr Leu Ser Cys Asp Leu Val Leu Ala
  1               5                  10                  15

Ala Ala Tyr Asn Asn Phe Arg Lys Ser Met Asp Ser Ile Gly Lys Lys
             20                  25                  30

Gln Tyr Gln Val Gln His Gly Ser Cys Ser Tyr Thr Phe Leu Leu Pro
         35                  40                  45

Glu Met Asp Asn Cys Arg Ser Ser Ser Pro Tyr Val Ser Asn Ala
 50                  55                  60

Val Gln Arg Asp Ala Pro Leu Glu Tyr Asp Ser Val Gln Arg Leu
 65                  70                  75                  80

Gln Val Leu Glu Asn Ile Met Glu Asn Asn Thr Gln Trp Leu Met Lys
             85                  90                  95

Leu Glu Asn Tyr Ile Gln Asp Asn Met Lys Lys Glu Met Val Glu Ile
            100                 105                 110

Gln Gln Asn Ala Val Gln Asn Gln Thr Ala Val Met Ile Glu Ile Gly
        115                 120                 125

Thr Asn Leu Leu Asn Gln Thr Ala Glu Gln Thr Arg Lys Leu Thr Asp
130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
            180                 185                 190

Lys Lys Val Leu Ala Met Glu Asp Lys His Ile Ile Gln Leu Gln Ser
        195                 200                 205

Ile Lys Glu Glu Lys Asp Gln Leu Gln Val Leu Val Ser Lys Gln Asn
    210                 215                 220

Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Glu Thr Val Asn
                245                 250                 255

Asn Leu Leu Thr Met Met Ser Thr Ser Asn Ser Ala Lys Asp Pro Thr
            260                 265                 270

Val Ala Lys Glu Glu Gln Ile Ser Phe Arg Asp Cys Ala Asp Val Tyr
        275                 280                 285

Gln Ala Gly Phe Asn Lys Ser Gly Ile Tyr Thr Ile Tyr Ile Asn Asn
    290                 295                 300

Met Pro Glu Pro Lys Lys Val Phe Cys Asn Met Asp Val Asn Gly Gly
305                 310                 315                 320

Gly Trp Thr Val Ile Gln His Arg Glu Asp Gly Ser Leu Asp Phe Gln
                325                 330                 335

Arg Gly Trp Lys Glu Tyr Lys Met Gly Phe Gly Asn Pro Ser Gly Glu
            340                 345                 350

Tyr Trp Leu Gly Asn Glu Phe Ile Phe Ala Ile Thr Ser Gln Arg Gln
        355                 360                 365

Tyr Met Leu Arg Ile Glu Leu Met Asp Trp Glu Gly Asn Arg Ala Tyr
    370                 375                 380
```

-continued

```
Ser Gln Tyr Asp Arg Phe His Ile Gly Asn Glu Lys Gln Asn Tyr Arg
385                 390                 395                 400

Leu Tyr Leu Lys Gly His Thr Gly Thr Ala Gly Lys Gln Ser Ser Leu
            405                 410                 415

Ile Leu His Gly Ala Asp Phe Ser Thr Lys Asp Ala Asp Asn Asp Asn
        420                 425                 430

Cys Met Cys Lys Cys Ala Leu Met Leu Thr Gly Gly Trp Trp Phe Asp
    435                 440                 445

Ala Cys Gly Pro Ser Asn Leu Asn Gly Met Phe Tyr Thr Ala Gly Gln
    450                 455                 460

Asn His Gly Lys Leu Asn Gly Ile Lys Trp His Tyr Phe Lys Gly Pro
465                 470                 475                 480

Ser Tyr Ser Leu Arg Ser Thr Thr Met Met Ile Arg Pro Leu Asp Phe
                485                 490                 495

<210> SEQ ID NO 23
<211> LENGTH: 1500
<212> TYPE: DNA
<213> ORGANISM: Homo sapien

<400> SEQUENCE: 23
atgacagttt tcctttcctt tgctttcctc gctgccattc tgactcacat agggtgcagc       60
aatcagcgcc gaagtccaga aaacagtggg agaagatata accggattca acatgggcaa      120
tgtgcctaca cttcattct tccagaacac gatggcaact gtcgtgagag tacgacagac       180
cagtacaaca caaacgctct gcagagagat gctccacacg tggaaccgga tgactcggtg      240
cagaggctgc aagtgctgga aacatcatg gaaaacaaca ctcagtggct aatgaagctt       300
gagaattata tccaggacaa catgaagaaa gaatggtag agatacagca gaatgcagta       360
cagaaccaga cggctgtgat gatagaaata gggacaaacc tgttgaacca acagctgag       420 caaacgcgga agttaactga tgtggaagcc caagtattaa atcagaccac gagacttgaa      480
cttcagctct tggaacactc cctctcgaca acaaattgg aaaaacagat tttggaccag       540
accagtgaaa taaacaaatt gcaagataag aacagttttcc tagaaaagaa ggtgctagct     600
atggaagaca agcacatcat ccaactacag tcaataaaag aagagaaaga tcagctacag      660
gtgttagtat ccaagcaaaa ttccatcatt gaagaactag aaaaaaaaat agtgactgcc      720
acggtgaata attcagttct tcaaaagcag caacatgatc tcatggagac agttaataac      780
ttactgacta tgatgtccac atcaaactca gctaaggacc ccactgttgc taaagaagaa      840
caaatcagct tcagagactg tgctgaagta ttcaaatcag acacaccac aaatggcatc       900 tacacgttaa cattccctaa ttctacagaa gagatcaagg cctactgtga catggaagct      960
ggaggaggcg gtggacaat tattcagcga cgtgaggatg gcagcgttga ttttcagagg      1020
acttggaaag aatataaagt gggatttggt aaccctcag gagaatattg gctgggaaat      1080
gagtttgttt cgcaactgac taatcagcaa cgctatgtgc ttaaaataca ccttaaagac      1140
tgggaaggga tgaggctta ctcattgtat gaacattct atctctcaag tgaagaactc       1200
aattatagga ttcaccttaa aggacttaca gggacagccg gcaaaataag cagcatcagc      1260
caaccaggaa atgatttag cacaaaggat ggagacaacg acaaatgtat ttgcaaatgt     1320
tcacaaatgc taacaggagg ctggtggttt gatgcatgtg gtccttccaa cttgaacgga      1380
atgtactatc acagaggca aacacaaat aagttcaacg gcattaaatg gtactactgg      1440
aaaggctcag gctattcgct caaggccaca accatgatga tccgaccagc agatttctaa     1500
```

<210> SEQ ID NO 24
<211> LENGTH: 499
<212> TYPE: PRT
<213> ORGANISM: Homo sapien

<400> SEQUENCE: 24

```
Met Thr Val Phe Leu Ser Phe Ala Phe Leu Ala Ala Ile Leu Thr His
 1               5                  10                  15

Ile Gly Cys Ser Asn Gln Arg Arg Ser Pro Glu Asn Ser Gly Arg Arg
                20                  25                  30

Tyr Asn Arg Ile Gln His Gly Gln Cys Ala Tyr Thr Phe Ile Leu Pro
            35                  40                  45

Glu His Asp Gly Asn Cys Arg Glu Ser Thr Thr Asp Gln Tyr Asn Thr
        50                  55                  60

Asn Ala Leu Gln Arg Asp Ala Pro His Val Glu Pro Asp Asp Ser Val
65                  70                  75                  80

Gln Arg Leu Gln Val Leu Glu Asn Ile Met Glu Asn Asn Thr Gln Trp
                85                  90                  95

Leu Met Lys Leu Glu Asn Tyr Ile Gln Asp Asn Met Lys Lys Glu Met
                100                 105                 110

Val Glu Ile Gln Gln Asn Ala Val Gln Asn Gln Thr Ala Val Met Ile
            115                 120                 125

Glu Ile Gly Thr Asn Leu Leu Asn Gln Thr Ala Glu Gln Thr Arg Lys
        130                 135                 140

Leu Thr Asp Val Glu Ala Gln Val Leu Asn Gln Thr Thr Arg Leu Glu
145                 150                 155                 160

Leu Gln Leu Leu Glu His Ser Leu Ser Thr Asn Lys Leu Glu Lys Gln
                165                 170                 175

Ile Leu Asp Gln Thr Ser Glu Ile Asn Lys Leu Gln Asp Lys Asn Ser
            180                 185                 190

Phe Leu Glu Lys Lys Val Leu Ala Met Glu Asp Lys His Ile Ile Gln
        195                 200                 205

Leu Gln Ser Ile Lys Glu Glu Lys Asp Gln Leu Gln Val Leu Val Ser
    210                 215                 220

Lys Gln Asn Ser Ile Ile Glu Glu Leu Glu Lys Lys Ile Val Thr Ala
225                 230                 235                 240

Thr Val Asn Asn Ser Val Leu Gln Lys Gln Gln His Asp Leu Met Glu
                245                 250                 255

Thr Val Asn Asn Leu Leu Thr Met Met Ser Thr Ser Asn Ser Ala Lys
            260                 265                 270

Asp Pro Thr Val Ala Lys Glu Glu Gln Ile Ser Phe Arg Asp Cys Ala
        275                 280                 285

Glu Val Phe Lys Ser Gly His Thr Thr Asn Gly Ile Tyr Thr Leu Thr
    290                 295                 300

Phe Pro Asn Ser Thr Glu Glu Ile Lys Ala Tyr Cys Asp Met Glu Ala
305                 310                 315                 320

Gly Gly Gly Gly Trp Thr Ile Ile Gln Arg Arg Glu Asp Gly Ser Val
                325                 330                 335

Asp Phe Gln Arg Thr Trp Lys Glu Tyr Lys Val Gly Phe Gly Asn Pro
            340                 345                 350

Ser Gly Glu Tyr Trp Leu Gly Asn Glu Phe Val Ser Gln Leu Thr Asn
        355                 360                 365

Gln Gln Arg Tyr Val Leu Lys Ile His Leu Lys Asp Trp Glu Gly Asn
    370                 375                 380
```

-continued

```
Glu Ala Tyr Ser Leu Tyr Glu His Phe Tyr Leu Ser Ser Glu Glu Leu
385                 390                 395                 400

Asn Tyr Arg Ile His Leu Lys Gly Leu Thr Gly Thr Ala Gly Lys Ile
            405                 410                 415

Ser Ser Ile Ser Gln Pro Gly Asn Asp Phe Ser Thr Lys Asp Gly Asp
            420                 425                 430

Asn Asp Lys Cys Ile Cys Lys Cys Ser Gln Met Leu Thr Gly Gly Trp
        435                 440                 445

Trp Phe Asp Ala Cys Gly Pro Ser Asn Leu Asn Gly Met Tyr Tyr Pro
    450                 455                 460

Gln Arg Gln Asn Thr Asn Lys Phe Asn Gly Ile Lys Trp Tyr Tyr Trp
465                 470                 475                 480

Lys Gly Ser Gly Tyr Ser Leu Lys Ala Thr Thr Met Met Ile Arg Pro
                485                 490                 495

Ala Asp Phe
```

<210> SEQ ID NO 25
<211> LENGTH: 1488
<212> TYPE: DNA
<213> ORGANISM: Homo sapien

<400> SEQUENCE: 25

| | | | | | |
|---|---|---|---|---|---|
| atgtggcaga | ttgttttctt | tactctgagc | tgtgatcttg | tcttggccgc | agcctataac | 60 |
| aactttcgga | gagcatgga | cagcatagga | agaagcaat | atcaggtcca | gcatgggtcc | 120 |
| tgcagctaca | ctttcctcct | gccagagatg | gacaactgcc | gctcttcctc | cagcccctac | 180 |
| gtgtccaatg | ctgtgcagag | ggacgcgccg | ctcgaatacg | atttctcttc | ccagaaactt | 240 |
| caacatctgg | aacatgtgat | ggaaaattat | actcagtggc | tgcaaaaact | tgagaattac | 300 |
| attgtggaaa | acatgaagtc | ggagatggcc | cagatacagc | agaatgcagt | tcagaaccac | 360 |
| acggctacca | tgctggagat | aggaaccagc | ctcctctctc | agactgcaga | gcagaccaga | 420 |
| aagctgacag | atgttgagac | ccaggtacta | aatcaaactt | ctcgacttga | gatacagctg | 480 |
| ctggagaatt | cattatccac | ctacaagcta | gagaagcaac | ttcttcaaca | gacaaatgaa | 540 |
| atcttgaaga | tccatgaaaa | aaacagttta | ttagaacata | aaatcttaga | aatggaagga | 600 |
| aaacacaagg | aagagttgga | caccttaaag | gaagagaaag | agaaccttca | aggcttggtt | 660 |
| actcgtcaaa | catatataat | ccaggagctg | gaaaagcaat | aaacagagc | taccaccaac | 720 |
| aacagtgtcc | ttcagaagca | gcaactggag | ctgatggaca | cagtccacaa | ccttgtcaat | 780 |
| ctttgcacta | agaaggtgt | tttactaaag | ggaggaaaaa | gagaggaaga | gaaaccattt | 840 |
| agagactgtg | cagatgtata | tcaagctggt | tttaataaaa | gtggaatcta | cactatttat | 900 |
| attaataata | tgccagaacc | caaaaaggtg | ttttgcaata | tggatgtcaa | tggggaggt | 960 |
| tggactgtaa | tacaacatcg | tgaagatgga | agtctagatt | ccaaagagg | ctggaaggaa | 1020 |
| tataaaatgg | gttttggaaa | tccctccggt | gaatattggc | tggggaatga | gtttattttt | 1080 |
| gccattacca | gtcagaggca | gtacatgcta | agaattgagt | taatgactg | ggaagggaac | 1140 |
| cgagcctatt | cacagtatga | cagattccac | ataggaaatg | aaaagcaaaa | ctataggttg | 1200 |
| tatttaaaag | gtcacactgg | gacagcagga | aaacagagca | gcctgatctt | acacggtgct | 1260 |
| gatttcagca | ctaaagatgc | tgataatgac | aactgtatgt | gcaaatgtgc | cctcatgtta | 1320 |
| acaggaggat | ggtggtttga | tgcttgtggc | ccctccaatc | taaatggaat | gttctatact | 1380 |
| gcgggacaaa | accatggaaa | actgaatggg | ataaagtggc | actacttcaa | agggcccagt | 1440 |

-continued tactccttac gttccacaac tatgatgatt cgacctttag atttttga       1488

<210> SEQ ID NO 26
<211> LENGTH: 495
<212> TYPE: PRT
<213> ORGANISM: Homo sapien

<400> SEQUENCE: 26

```
Met Trp Gln Ile Val Phe Phe Thr Leu Ser Cys Asp Leu Val Leu Ala
 1               5                  10                  15

Ala Ala Tyr Asn Asn Phe Arg Lys Ser Met Asp Ser Ile Gly Lys Lys
            20                  25                  30

Gln Tyr Gln Val Gln His Gly Ser Cys Ser Tyr Thr Phe Leu Leu Pro
        35                  40                  45

Glu Met Asp Asn Cys Arg Ser Ser Ser Pro Tyr Val Ser Asn Ala
 50                  55                  60

Val Gln Arg Asp Ala Pro Leu Glu Tyr Asp Phe Ser Ser Gln Lys Leu
 65                  70                  75                  80

Gln His Leu Glu His Val Met Glu Asn Tyr Thr Gln Trp Leu Gln Lys
                85                  90                  95

Leu Glu Asn Tyr Ile Val Glu Asn Met Lys Ser Glu Met Ala Gln Ile
            100                 105                 110

Gln Gln Asn Ala Val Gln Asn His Thr Ala Thr Met Leu Glu Ile Gly
        115                 120                 125

Thr Ser Leu Leu Ser Gln Thr Ala Glu Gln Thr Arg Lys Leu Thr Asp
130                 135                 140

Val Glu Thr Gln Val Leu Asn Gln Thr Ser Arg Leu Glu Ile Gln Leu
145                 150                 155                 160

Leu Glu Asn Ser Leu Ser Thr Tyr Lys Leu Glu Lys Gln Leu Leu Gln
                165                 170                 175

Gln Thr Asn Glu Ile Leu Lys Ile His Glu Lys Asn Ser Leu Leu Glu
            180                 185                 190

His Lys Ile Leu Glu Met Glu Gly Lys His Lys Glu Glu Leu Asp Thr
        195                 200                 205

Leu Lys Glu Glu Lys Glu Asn Leu Gln Gly Leu Val Thr Arg Gln Thr
210                 215                 220

Tyr Ile Ile Gln Glu Leu Glu Lys Gln Leu Asn Arg Ala Thr Thr Asn
225                 230                 235                 240

Asn Ser Val Leu Gln Lys Gln Gln Leu Glu Leu Met Asp Thr Val His
                245                 250                 255

Asn Leu Val Asn Leu Cys Thr Lys Glu Gly Val Leu Leu Lys Gly Gly
            260                 265                 270

Lys Arg Glu Glu Glu Lys Pro Phe Arg Asp Cys Ala Asp Val Tyr Gln
        275                 280                 285

Ala Gly Phe Asn Lys Ser Gly Ile Tyr Thr Ile Tyr Ile Asn Asn Met
        290                 295                 300

Pro Glu Pro Lys Lys Val Phe Cys Asn Met Asp Val Asn Gly Gly Gly
305                 310                 315                 320

Trp Thr Val Ile Gln His Arg Glu Asp Gly Ser Leu Asp Phe Gln Arg
                325                 330                 335

Gly Trp Lys Glu Tyr Lys Met Gly Phe Gly Asn Pro Ser Gly Glu Tyr
            340                 345                 350

Trp Leu Gly Asn Glu Phe Ile Phe Ala Ile Thr Ser Gln Arg Gln Tyr
        355                 360                 365
```

```
Met Leu Arg Ile Glu Leu Met Asp Trp Glu Gly Asn Arg Ala Tyr Ser
    370             375                 380
Gln Tyr Asp Arg Phe His Ile Gly Asn Glu Lys Gln Asn Tyr Arg Leu
385             390                 395                 400
Tyr Leu Lys Gly His Thr Gly Thr Ala Gly Lys Gln Ser Ser Leu Ile
                405             410                 415
Leu His Gly Ala Asp Phe Ser Thr Lys Asp Ala Asp Asn Asp Asn Cys
                420             425                 430
Met Cys Lys Cys Ala Leu Met Leu Thr Gly Gly Trp Trp Phe Asp Ala
            435             440                 445
Cys Gly Pro Ser Asn Leu Asn Gly Met Phe Tyr Thr Ala Gly Gln Asn
            450             455                 460
His Gly Lys Leu Asn Gly Ile Lys Trp His Tyr Phe Lys Gly Pro Ser
465             470                 475                 480
Tyr Ser Leu Arg Ser Thr Thr Met Met Ile Arg Pro Leu Asp Phe
                485             490                 495

<210> SEQ ID NO 27
<211> LENGTH: 47
<212> TYPE: DNA
<213> ORGANISM: Homo sapien

<400> SEQUENCE: 27
gcatgctatc tcgagccacc atgctctccc agctagccat gctgcag                47

<210> SEQ ID NO 28
<211> LENGTH: 55
<212> TYPE: DNA
<213> ORGANISM: Homo sapien

<400> SEQUENCE: 28
gtgtcgacgc ggccgctcta gatcagactt agatgtccaa aggccgtatc atcat      55

<210> SEQ ID NO 29
<211> LENGTH: 25
<212> TYPE: DNA
<213> ORGANISM: Homo sapien

<400> SEQUENCE: 29
cctctgggct cgccagtttg ttagg                                       25

<210> SEQ ID NO 30
<211> LENGTH: 19
<212> TYPE: DNA
<213> ORGANISM: Homo sapien

<400> SEQUENCE: 30
ccagctggca gatatcagg                                              19
```